US008809395B2

(12) United States Patent
Mulzer et al.

(10) Patent No.: US 8,809,395 B2
(45) Date of Patent: Aug. 19, 2014

(54) METHODS FOR MAKING VALERENIC ACID DERIVATIVES AND THEIR USE

(75) Inventors: Johann Mulzer, Vienna (AT); Jürgen Ramharter, Vienna (AT); Steffen Hering, Vienna (AT); Sophia Khom, Vienna (AT)

(73) Assignee: Valericon GmbH, Vienna (AT)

( * ) Notice: Subject to any disclaimer, the term of this patent is extended or adjusted under 35 U.S.C. 154(b) by 238 days.

(21) Appl. No.: 13/138,227

(22) PCT Filed: Jan. 22, 2010

(86) PCT No.: PCT/EP2010/050750
§ 371 (c)(1),
(2), (4) Date: Oct. 4, 2011

(87) PCT Pub. No.: WO2010/084182
PCT Pub. Date: Jul. 29, 2010

(65) Prior Publication Data
US 2012/0022283 A1  Jan. 26, 2012

(30) Foreign Application Priority Data
Jan. 23, 2009 (EP) .................................... 09151278

(51) Int. Cl.
*A61K 31/16*   (2006.01)
*C07C 233/02*  (2006.01)
*C07C 233/10*  (2006.01)
*C07C 233/16*  (2006.01)
*C07C 243/32*  (2006.01)
*C07C 231/02*  (2006.01)

(52) U.S. Cl.
CPC .............. *C07C 233/02* (2013.01); *A61K 31/16* (2013.01); *C07C 233/10* (2013.01); *C07C 233/16* (2013.01); *C07C 243/32* (2013.01); *C07C 231/02* (2013.01)
USPC ........... 514/613; 514/614; 514/627; 564/148; 564/134; 564/189; 564/191; 560/119

(58) Field of Classification Search
CPC .. C07C 233/02; C07C 233/10; C07C 233/16; C07C 233/32; C07C 231/02; A61K 31/16
USPC ........... 514/613, 614; 564/148, 189, 191, 134
See application file for complete search history.

(56) References Cited

U.S. PATENT DOCUMENTS

2003/0012824 A1*  1/2003  Ott et al. ...................... 424/602

OTHER PUBLICATIONS

Bos et al. Phytochemistry (1986), 25(1), p. 133 (STN search report).*
Zizovic et al. J. of Supercritical Fluids 43, (2007), p. 249-258.*
International Search Report dated Jun. 23, 2010 for PCT Application No. PCT/EP2010/050750.
International Preliminary Report on Patentability dated Jul. 6, 2011 for PCT Application No. PCT/EP2010/050750.
Khom et al. "Valerenic acid potentiates and inhibits GABAA receptors: Molecular mechanism and subunit specificity." Neuropharmacology 53 (2007) 178-187.

* cited by examiner

*Primary Examiner* — Yong Chu
(74) *Attorney, Agent, or Firm* — Amster, Rothstein & Ebenstein LLP

(57) ABSTRACT

The present invention is directed to compounds, intermediates and methods for making valerenic acid and its derivatives as well as the use of such compounds as $GABA_A$ receptor ligands.

11 Claims, 3 Drawing Sheets

METHODS FOR MAKING VALERENIC ACID DERIVATIVES AND THEIR USE

This is a U.S. national phase of PCT Application No. PCT/EP2010/050750, filed Jan. 22, 2010, which claims priority to European Patent Application No. 09151278.0, filed Jan. 23, 2009.

FIELD OF THE INVENTION

The present invention relates to valerenic acid derivatives being suitable for pharmaceutical compositions and methods for making them. Furthermore, the present invention relates to pharmaceutical compositions comprising said compounds, which exhibit $GABA_A$ receptor binding activity. Said compositions may particularly be used for the treatment of anxiety and insomnia.

BACKGROUND OF THE INVENTION

Insomnia and anxiety are two conditions, which have substantial negative impact on day-to-day quality of life. Insomnia is often described as subjective complaint of poor sleep quality or quantity despite adequate time for sleep. Insomnia results in daytime fatigue, irritability and decreased concentration and is often associated with other diseases such as psychiatric disorders (e.g. anxiety conditions), medical disorders or substance abuse. Anxiety also leads to fatigue, irritability and decreased concentration. Several forms of anxiety are known, such as generalized anxiety disorder, panic disorder, social anxiety disorder and post-traumatic stress disorder. Effective treatment of said conditions thus positively influences day-to-day life of patients suffering from such conditions.

Current pharmaceuticals used for the treatment of insomnia and anxiety comprise benzodiazepines, benzodiazepine-receptor agonists, melatonin-receptor agonists as well as anti-depressants. However, most of said drugs exhibit strong adverse effects such as addiction and substance abuse. Naturally-occurring and traditionally used pharmaceuticals comprise herbal substances such as valerenic acid. However, many patients describe their action as too weak to result in satisfying relief of the conditions outlined above.

$GABA_A$ receptors thus represent promising molecular targets for the treatment of inter alia insomnia and anxiety.

On a molecular level, it seems that herbal substances such as valerian extracts comprising valerenic acid target inter alia $GABA_A$ receptors. The pharmacological properties of $GABA_A$ receptors as well as their sensitivity to γ-aminobutyric acid (GABA) seem to be determined by the subunit composition. The completely assembled receptor is comprised of five subunits. Up to now, 19 isoforms of mammalian $GABA_A$ receptor subunits could be identified: α1-6, β1-3, γ1-3, δ, ε, π, ρ1-3 and θ, and it seems that most of the endogenous as well as exogenous ligands bind to interfaces between two of the subunits. $GABA_A$ receptors seem to be implicated in signaling processes involved in diseases such as insomnia and anxiety as already mentioned above, but also processes involved in pain, mood and panic disorders, epilepsy, schizophrenia and symptoms connected to alcohol and/or substance withdrawal/abuse. Therefore, compounds affecting $GABA_A$ receptors may not only be used for treating insomnia and anxiety disorders but possibly also for treating pain, mood and panic disorders, epilepsy, schizophrenia and symptoms connected to alcohol and/or substance withdrawal/abuse.

Furthermore, such compounds may be used for the diagnosis and treatment of anxiety, Down Syndrome, sleep, cognitive and seizure disorders, depression, overdose with benzodiazepine drugs, enhancement of memory and alertness, Huntington's Chorea, muscular spasms and rigidity, sleep and seizure disorders, and withdrawal symptoms. Antagonists may be used, for example, to diagnose and treat Alzheimer's disease, Parkinson's disease and for enhancing cognition and reversing sedation after application of general anesthesia during surgery. Modulators can be useful in the prevention of anxiety disorders, such as panic disorder with or without agoraphobia, agoraphobia without history of panic disorder, phobias including social phobias, obsessive-compulsive disorder, stress disorders including post-traumatic and acute stress disorder, and generalized or substance-induced anxiety disorder; depression or bipolar disorders such as single-episode or recurrent major depressive disorder, dysthymic disorder, bipolar I and bipolar II manic disorders; schizophrenia; attention deficit hyperactivity disorder and disorders of circadian rhythm, e.g. in subjects suffering from the effects of jet lag or shift work; convulsive or seizure disorders such as epilepsy and pain.

Modulators can be also used as general anaesthetics.

So far, no complete synthesis for making the natural compound valerenic acid or any derivatives thereof has been described. However, there have been attempts towards such a method as disclosed in Krishna, Rao G. S. Tetrahedron 1967, 23, 3215. However, the synthesis described therein does only provide for an epimere with the wrong configuration compared to natural valerenic acid (said structure is shown below in the detailed description of the invention). Further publications such as Bohlmann, F. and Lonitz, M. Chem. Ber. 1980, 113, 2410 and Baudouy, R. and Sartorette, J. Tetrahydron 1983, 39, 3293, are concerned with the synthesis of valerenal, but not with the synthesis of valerenic acid.

There is a need for alternative or improved compounds, which act as $GABA_A$ receptor ligands and thus may be used for the treatment of e.g. insomnia and anxiety. Furthermore, there is a need to provide a method or synthesis route which allows for making valerenic acid and valerenic acid derivatives and preferably is stereoselective.

OBJECTS AND SUMMARY OF THE INVENTION

Accordingly, it is an object of the present invention to provide new compounds which exhibit affinity for the $GABA_A$ receptor.

It is another object of certain embodiments of the present invention to provide pharmaceutical compositions comprising new compounds exhibiting affinity for the $GABA_A$ receptor. In certain embodiments, said new compounds are used for the manufacture of a medicament for treatment of anxiety and/or insomnia. In certain embodiments, said new compounds are used for the manufacture of a medicament for modulating a pharmacological response from the $GABA_A$ receptor.

It is an object of certain embodiments of the present invention to provide new compounds which exhibit greater affinity for the $GABA_A$ receptor than valerenic acid or other compounds currently available and/or which produce less side effects than other compounds currently available.

Furthermore, it is an object of the present invention to provide methods for making valerenic acid and derivatives thereof. Said method should preferably be stereoselective.

These and other objectives of the present invention, as they will become apparent from the ensuing description, are solved by the subject matter of the independent claims. The dependent claims relate to some of the preferred embodiments of the invention.

The present invention in certain embodiments refers to compounds of the general formula (I):

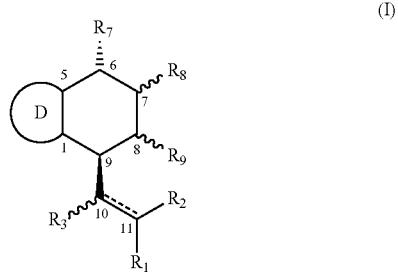

wherein
the dotted line between $C_{10}$ and $C_{11}$ represents an optional double bond;
D is selected from the group of 5-membered rings consisting of the following structures:

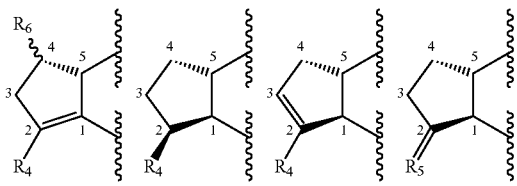

$R_1$ is selected from the group consisting of substituted or unsubstituted C1-C10 alkyl, substituted or unsubstituted C3-C8cycloalkyl, substituted or unsubstituted C2-C10alkenyl, substituted or unsubstituted C4-C8cycloalkenyl, substituted or unsubstituted aryl, substituted or unsubstituted heteroaryl, —(C0-C10)C(O)$R_{10}$, —(C0-C10)C(O)O$R_{10}$, —(C0-C10)OC(O)$R_{10}$, —(C1-C10)S$R_{10}$, —(C0-C10)C(O)NR$_{11}R_{12}$, —(C0-C10)C(O)NHNR$_{11}R_{12}$ and —(C1-C10)O$R_{10}$;
wherein $R_{10}$, $R_{11}$ and $R_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;
$R_2$, $R_3$, $R_4$, $R_7$, $R_8$ and $R_9$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl, substituted or unsubstituted heteroaryl, —CN, —(C1-C10)OH, —NR$_{11}R_{12}$, —(C0-C10)C(O)$R_{10}$, —(C0-C10)C(O)O$R_{10}$, —(C0-C10)OC(O)$R_{10}$, —(C1-C10)S$R_{10}$, —(C0-C10)C(O)NR$_{11}R_{12}$, —C(O)NHNR$_{11}R_{12}$ and —(C0-C10)O$R_{10}$;
wherein $R_{10}$, $R_{11}$ and $R_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;

$R_5$ is selected from the group consisting of O and CHR$_{13}$;
wherein $R_{13}$ is selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;

$R_6$ is selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl, substituted or unsubstituted heteroaryl, —CN, —(C1-C10)OH, —NR$_{11}R_{12}$, —(C0-C10)C(O)$R_{10}$, —(C0-C10)C(O)O$R_{10}$, —(C1-C10)OC(O)$R_{10}$, —(C1-C10)S$R_{10}$, —(C0-C10)C(O)NR$_{11}R_{12}$, —C(O)NHNR$_{11}R_{12}$, —(C1-C10)O$R_{10}$, —O$R_{14}$ and —OC(O)$R_{14}$;
wherein $R_{10}$, $R_{11}$, $R_{12}$ and $R_{14}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;

or a pharmaceutically salt thereof or solvate thereof;
excluding the following compounds:

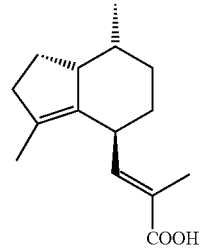

(E1)

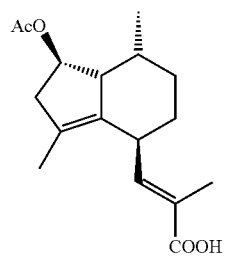

(E2)

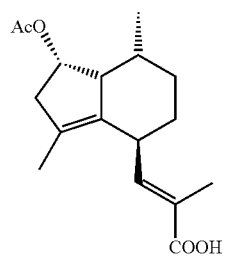

(E3)

-continued (E4)

(E5)

(E6)

(E7)

(E8)

(E9)

(E10)

(E11)

(E12)

(E13)

(E14)

(E15)

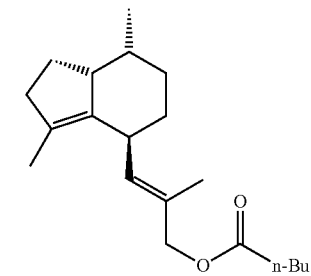

(E16)

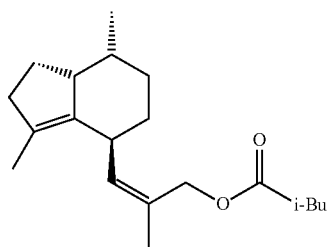

(E17)

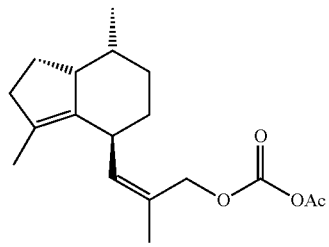

(E18)

According to one aspect of the present invention, the inventive compounds of the general formula (I) do not include the cis- and trans-isomers (also called Z- and E-isomers) of compounds (E1), (E1), (E2), (E3), (E4), (E5), (E6), (E7), (E8), (E9), (E10), (E11), (E12), (E13), (E14), (E15), (E16), (E17) and (E18) having a double bond between $C_{10}$ and $C_{11}$. Additionally or alternatively, the inventive compounds of the general formula (I) do not include those inventive compounds of the general formula (I) which have a bicyclic ring structure where the ring structure does not comprise a carbon-carbon double bond and where $R_7$, $R_8$ and $R_9$ are hydrogen and especially do not include those inventive compounds of the general formula (I) which have a bicyclic ring structure where the ring structure does not comprise a carbon-carbon double bond and where $R_7$, $R_8$ and $R_9$ are hydrogen and where $R_4$ is a methyl-group, a OH-group or H, or $R_5$ is O. Additionally or alternatively, the inventive compounds of the general formula (I) do not include those inventive compounds of the general formula (I) where $R_1$ and $R_2$ are both methyl-groups and especially do not include those inventive compounds of the general formula (I) where $R_1$ and $R_2$ are both methyl-groups and $R_6$ or $R_7$ is a methyl-group.

In certain preferred embodiments of the compounds according to formula (I), the bond between $C_{10}$ and $C_{11}$ is a double bond.

In certain preferred embodiments of the compounds according to formula (I), D is selected from the group of 5-membered rings consisting of the following structures:

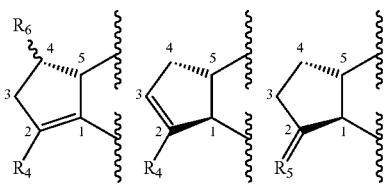

In certain preferred embodiments of the compounds according to formula (I), $R_3$ is H.

In certain preferred embodiments of the compounds according to formula (I), $R_6$ is in the following configuration corresponding to a cis-configuration with respect to $R_7$:

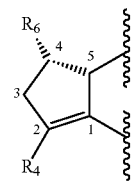

In certain preferred embodiments of the compounds according to formula (I), $R_8$ is H.

In certain preferred embodiments of the compounds according to formula (I), $R_7$ is selected from the group consisting of substituted or unsubstituted C6-C10alkyl, substituted or unsubstituted C5-C8cycloalkyl, substituted or unsubstituted C6-C10alkenyl, substituted or unsubstituted C4-C8cycloalkenyl, substituted or unsubstituted aryl, substituted or unsubstituted heteroaryl, —(C6-C10)OH, —$NR_{11}R_{12}$, —(C6-C10)C(O)$R_{10}$, —(C6-C10)C(O)O$R_{10}$, —(C0-C10)OC(O)$R_{10}$, —(C6-C10)S$R_{10}$, —(C6-C10)C(O)N$R_{11}R_{12}$, —C(O)NHN$R_{11}R_{12}$ and —(C6-C10)O$R_{10}$;

wherein $R_{10}$, $R_{11}$ and $R_{12}$ independently from each other are selected from the group consisting of substituted or unsubstituted C6-C10alkyl, substituted or unsubstituted C5-C8cycloalkyl, substituted or unsubstituted C6-C10alkenyl, substituted or unsubstituted C4-C8cycloalkenyl, substituted or unsubstituted aryl and substituted or unsubstituted heteroaryl.

In certain preferred embodiments of the compounds according to formula (I), the bond between $C_{10}$ and $C_{11}$ is a double bond, $R_2$ is unsubstituted C1-C3alkyl, $R_3$ is H, $R_4$ is unsubstituted C1-C3alkyl, $R_6$ is H, $R_7$ is unsubstituted C1-C3alkyl, $R_8$ is H and $R_9$ is unsubstituted C1-C3alkyl. In certain even more preferred embodiments of the compounds according to formula (I), the bond between $C_{10}$ and $C_{11}$ is a double bond, $R_2$ is unsubstituted C1-C3alkyl, $R_3$ is H, $R_6$ is H, $R_8$ is H, $R_9$ is unsubstituted C1-C3alkyl and $R_4$ and $R_7$ are methyl.

In certain preferred embodiments of the compounds according to formula (I), the bond between $C_{10}$ and $C_{11}$ is a double bond, $R_2$ is unsubstituted C1-C3alkyl, $R_3$ is H, $R_6$ is H, $R_7$ is unsubstituted C1-C3alkyl, $R_8$ is H and $R_9$ is unsubstituted C1-C3alkyl.

The present invention in certain embodiments comprises compounds of the general formula (IA1):

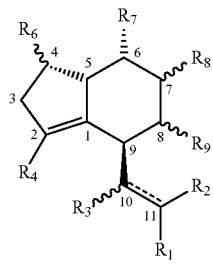

(IA1)

wherein
the dotted line between $C_{10}$ and $C_{11}$ represents an optional double bond;
$R_1$ is selected from the group consisting of substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl, substituted or unsubstituted heteroaryl, —(C0-C10)C(O)$R_{10}$, —(C0-C10)C(O)O$R_{10}$, —(C0-C10)OC(O)$R_{10}$, —(C1-C10)S$R_{10}$, —(C0-C10)C(O)N$R_{11}R_{12}$, —(C0-C10)C(O)NHN$R_{11}R_{12}$ and —(C1-C10)O$R_{10}$;
  wherein $R_{10}$, $R_{11}$ and $R_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;
$R_2$, $R_3$, $R_4$, $R_7$, $R_8$ and $R_9$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl, substituted or unsubstituted heteroaryl, —CN, —(C1-C10)OH, —N$R_{11}R_{12}$, —(C0-C10)C(O)$R_{10}$, —(C0-C10)C(O)O$R_{10}$, —(C0-C10)OC(O)$R_{10}$, —(C1-C10)S$R_{10}$, —(C0-C10)C(O)N$R_{11}R_{12}$, —C(O)NHN$R_{11}R_{12}$ and —(C0-C10)O$R_{10}$;
  wherein $R_{10}$, $R_{11}$ and $R_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;
$R_6$ is selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl, substituted or unsubstituted heteroaryl, —CN, —(C1-C10)OH, —N$R_{11}R_{12}$, —(C0-C10)C(O)$R_{10}$, —(C0-C10)C(O)O$R_{10}$, —(C1-C10)OC(O)$R_{10}$, —(C1-C10)S$R_{10}$, —(C0-C10)C(O)N$R_{11}R_{12}$, —C(O)NHN$R_{11}R_{12}$, —(C1-C10)O$R_{10}$, —O$R_{14}$ and —OC(O)$R_{14}$;
  wherein $R_{10}$, $R_{11}$, $R_{12}$ and $R_{14}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;
or a pharmaceutically salt thereof or solvate thereof.

In certain preferred embodiments of formula (IA1), the bond between $C_{10}$ and $C_{11}$ is a double bond.

In certain preferred embodiments of formula (IA1), $R_3$ is H.

In certain preferred embodiments of the compounds according to formula (IA1), $R_6$ is in the following configuration corresponding to a cis-configuration with respect to $R_7$:

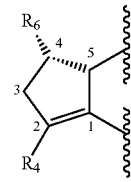

In certain preferred embodiments of the compounds according to formula (IA1), $R_8$ is H.
In certain preferred embodiments of formula (IA1), $R_8$ is H.
In certain preferred embodiments of formula (IA1), $R_7$ is selected from the group consisting of substituted or unsubstituted C6-C10 alkyl, substituted or unsubstituted C5-C8cycloalkyl, substituted or unsubstituted C6-C10alkenyl, substituted or unsubstituted C4-C8cycloalkenyl, substituted or unsubstituted aryl, substituted or unsubstituted heteroaryl, —(C6-C10)OH, —N$R_{11}R_{12}$, —(C6-C10)C(O)$R_{10}$, —(C6-C10)C(O)O$R_{10}$, —(C0-C10)OC(O)$R_{10}$, —C6-C10)S$R_{10}$, —(C6-C10)C(O)N$R_{11}R_{12}$, —C(O)NHN$R_{11}R_{12}$ and —(C6-C10)O$R_{10}$;
  wherein $R_{10}$, $R_{11}$ and $R_{12}$ independently from each other are selected from the group consisting of substituted or unsubstituted C6-C10alkyl, substituted or unsubstituted C5-C8cycloalkyl, substituted or unsubstituted C6-C10alkenyl, substituted or unsubstituted C4-C8cycloalkenyl, substituted or unsubstituted aryl and substituted or unsubstituted heteroaryl.

In certain preferred embodiments of formula (IA1), $R_6$ is H.

In certain preferred embodiments of formula (IA1), the bond between $C_{10}$ and $C_{11}$ is a double bond, $R_2$ is unsubstituted C1-C3alkyl, $R_3$ is H, $R_4$ is unsubstituted C1-C3alkyl, $R_6$ is H, $R_7$ is unsubstituted C1-C3alkyl, $R_8$ is H and $R_9$ is unsubstituted C1-C3alkyl. In certain even more preferred embodiments of formula (IA1), the bond between $C_{10}$ and $C_{11}$ is a double bond, $R_2$ is unsubstituted C1-C3alkyl, $R_3$ is H, $R_6$ is H, $R_8$ is H, $R_9$ is unsubstituted C1-C3alkyl and $R_4$ and $R_7$ is methyl.

In certain preferred embodiments of formula (IA1), the bond between $C_{10}$ and $C_{11}$ is a double bond, $R_2$ is unsubstituted C1-C3alkyl, $R_3$ is H, $R_6$ is H, $R_7$ is unsubstituted C1-C3alkyl, $R_8$ is H and $R_9$ is unsubstituted C1-C3alkyl.

The present invention in certain embodiments comprises compounds of the general formula (IA2):

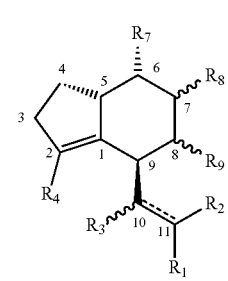

(IA2)

wherein
the dotted line between $C_{10}$ and $C_{11}$ represents an optional double bond;
$R_1$ is selected from the group consisting of substituted or unsubstituted $C_1$-C10alkyl, substituted or unsubstituted C3-C8cycloalkyl, substituted or unsubstituted C2-C10alkenyl, substituted or unsubstituted C4-C8cycloalkenyl, substituted or unsubstituted aryl, substituted or unsubstituted heteroaryl, —(C0-C10)C(O)R$_{10}$, —(C0-C10)C(O)OR$_{10}$, —(C0-C10)OC(O)R$_{10}$, —(C1-C10)SR$_{10}$, —(C0-C10)C(O)NR$_{11}$R$_{12}$, —(C0-C10)C(O)NHNR$_{11}$R$_{12}$ and —(C1-C10)OR$_{10}$;

wherein R$_{10}$, R$_{11}$ and R$_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;

R$_2$, R$_3$, R$_4$, R$_7$, R$_8$ and R$_9$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl, substituted or unsubstituted heteroaryl, —CN, —(C1-C10)OH, —NR$_{11}$R$_{12}$, —(C0-C10)C(O)R$_{10}$, —(C0-C10)C(O)OR$_{10}$, —(C0-C10)OC(O)R$_{10}$, —(C1-C10)SR$_{10}$, —(C0-C10)C(O)NR$_{11}$R$_{12}$, —C(O)NHNR$_{11}$R$_{12}$ and —(C0-C10)OR$_{10}$;

wherein R$_{10}$, R$_{11}$ and R$_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;

or a pharmaceutically salt thereof or solvate thereof.

In certain preferred embodiments of formula (IA2), the bond between C$_{10}$ and C$_{11}$ is a double bond.

In certain preferred embodiments of formula (IA2), R$_3$ is H.

In certain preferred embodiments of the compounds according to formula (IA2), R$_8$ is H.

In certain preferred embodiments of formula (IA2), R$_8$ is H.

In certain preferred embodiments of formula (IA2), R$_7$ is selected from the group consisting of substituted or unsubstituted C6-C10 alkyl, substituted or unsubstituted C5-C8cycloalkyl, substituted or unsubstituted C6-C10alkenyl, substituted or unsubstituted C4-C8cycloalkenyl, substituted or unsubstituted aryl, substituted or unsubstituted heteroaryl, —(C6-C10)OH, —NR$_{11}$R$_{12}$, —(C6-C10)C(O)R$_{10}$, —(C6-C10)C(O)OR$_{10}$, —(C0-C10)OC(O)R$_{10}$, —C6-C10)SR$_{10}$, —(C6-C10)C(O)NR$_{11}$R$_{12}$, —C(O)NHNR$_{11}$R$_{12}$ and —(C6-C10)OR$_{10}$;

wherein R$_{10}$, R$_{11}$ and R$_{12}$ independently from each other are selected from the group consisting of substituted or unsubstituted C6-C10alkyl, substituted or unsubstituted C5-C8cycloalkyl, substituted or unsubstituted C6-C10alkenyl, substituted or unsubstituted C4-C8cycloalkenyl, substituted or unsubstituted aryl and substituted or unsubstituted heteroaryl.

In certain preferred embodiments of formula (IA2), R$_6$ is H.

In certain preferred embodiments of formula (IA2), the bond between C$_{10}$ and C$_{11}$ is a double bond, R$_2$ is unsubstituted C1-C3alkyl, R$_3$ is H, R$_4$ is unsubstituted C1-C3alkyl, R$_6$ is H, R$_7$ is unsubstituted C1-C3alkyl, R$_8$ is H and R$_9$ is unsubstituted C1-C3alkyl. In certain even more preferred embodiments of formula (IA2), the bond between C$_{10}$ and C$_{11}$ is a double bond, R$_2$ is unsubstituted C1-C3alkyl, R$_3$ is H, R$_6$ is H, R$_8$ is H, R$_9$ is unsubstituted C1-C3alkyl and R$_4$ and/or R$_7$ is methyl.

In certain preferred embodiments of formula (IA2), the bond between C$_{10}$ and C$_{11}$ is a double bond, R$_2$ is unsubstituted C1-C3alkyl, R$_3$ is H, R$_6$ is H, R$_7$ is unsubstituted C1-C3alkyl, R$_8$ is H and R$_9$ is unsubstituted C1-C3alkyl.

The present invention in certain embodiments comprises compounds of the general formula (IB):

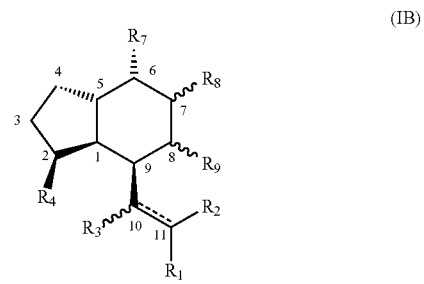

(IB)

wherein
the dotted line between C$_{10}$ and C$_{11}$ represents an optional double bond;

R$_1$ is selected from the group consisting of substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl, substituted or unsubstituted heteroaryl, —(C0-C10)C(O)R$_{10}$, —(C0-C10)C(O)OR$_{10}$, —(C0-C10)OC(O)R$_{10}$, —(C1-C10)SR$_{10}$, —(C0-C10)C(O)NR$_{11}$R$_{12}$, —(C0-C10)C(O)NHNR$_{11}$R$_{12}$ and —(C1-C10)OR$_{10}$;

wherein R$_{10}$, R$_{11}$ and R$_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;

R$_2$, R$_3$, R$_4$, R$_7$, R$_8$ and R$_9$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl, substituted or unsubstituted heteroaryl, —CN, —(C1-C10)OH, —NR$_{11}$R$_{12}$, —(C0-C10)C(O)R$_{10}$, —(C0-C10)C(O)OR$_{10}$, —(C0-C10)OC(O)R$_{10}$, —(C1-C10)SR$_{10}$, —(C0-C10)C(O)NR$_{11}$R$_{12}$, —C(O)NHNR$_{11}$R$_{12}$ and —(C0-C10)OR$_{10}$;

wherein R$_{10}$, R$_{11}$ and R$_{12}$ independently from each other are selected from the group consisting of H, substituted or unsubstituted C$_1$-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;

or a pharmaceutically salt thereof or solvate thereof.

In certain preferred embodiments of formula (IB), the bond between C$_{10}$ and C$_{11}$ is a double bond.

In certain preferred embodiments of formula (IB), R$_3$ is H.

In certain preferred embodiments of formula (IB), R$_8$ is H.

In certain preferred embodiments of formula (IB), R$_7$ is selected from the group consisting of substituted or unsubstituted C6-C10 alkyl, substituted or unsubstituted C5-C8cycloalkyl, substituted or unsubstituted C6-C10alkenyl, substituted or unsubstituted C4-C8cycloalkenyl, substituted or unsubstituted aryl, substituted or unsubstituted heteroaryl, —(C6-C10)OH, —NR$_{11}$R$_{12}$, —(C6-C10)C(O)R$_{10}$, —(C6-C10)C(O)OR$_{10}$, —(C0-C10)OC(O)R$_{10}$, —(C6-C10)SR$_{10}$, —(C6-C10)C(O)NR$_{11}$R$_{12}$, —C(O)NHNR$_{11}$R$_{12}$ and —(C6-C10)OR$_{10}$;

wherein R$_{10}$, R$_{11}$ and R$_{12}$ independently from each other are selected from the group consisting of substituted or unsubstituted C6-C10alkyl, substituted or unsubstituted C5-C8cycloalkyl, substituted or unsubstituted C6-C10alkenyl, substituted or unsubstituted C4-C8cycloalkenyl, substituted or unsubstituted aryl and substituted or unsubstituted heteroaryl.

In certain preferred embodiments of formula (IB), the bond between C$_{10}$ and C$_{11}$ is a double bond, R$_2$ is unsubstituted C1-C3alkyl, R$_3$ is H, R$_4$ is unsubstituted C1-C3alkyl, R$_7$ is unsubstituted C1-C3alkyl, R$_8$ is H and R$_9$ is unsubstituted C1-C3alkyl. In certain even more preferred embodiments of formula (IB), the bond between C$_{10}$ and C$_{11}$ is a double bond, R$_2$ is unsubstituted C1-C3alkyl, R$_3$ is H, R$_8$ is H, R$_9$ is unsubstituted C1-C3alkyl and R$_4$ and/or R$_7$ is methyl.

In certain preferred embodiments of formula (IB), the bond between C$_{10}$ and C$_{11}$ is a double bond, R$_2$ is unsubstituted C1-C3alkyl, R$_3$ is H, R$_7$ is unsubstituted C1-C3alkyl, R$_8$ is H and R$_9$ is unsubstituted C1-C3alkyl.

The present invention in certain embodiments comprises compounds of the general formula (IC):

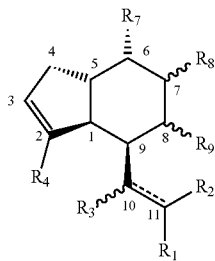

(IC)

wherein
the dotted line between C$_{10}$ and C$_{11}$ represents an optional double bond;
R$_1$ is selected from the group consisting of substituted or unsubstituted C1-C10 alkyl, substituted or unsubstituted C3-C8cycloalkyl, substituted or unsubstituted C2-C10alkenyl, substituted or unsubstituted C4-C8cycloalkenyl, substituted or unsubstituted aryl, substituted or unsubstituted heteroaryl, —(C0-C10)C(O)R$_{10}$, —(C0-C10)C(O)OR$_{10}$, —(C0-C10)OC(O)R$_{10}$, —(C1-C10)SR$_{10}$, —(C0-C10)C(O)NR$_{11}$R$_{12}$, —(C0-C10)C(O)NHNR$_{11}$R$_{12}$ and —(C1-C10)OR$_{10}$;

wherein R$_{10}$, R$_{11}$ and R$_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;

R$_2$, R$_3$, R$_4$, R$_7$, R$_8$ and R$_9$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl, substituted or unsubstituted heteroaryl, —CN, —(C1-C10)OH, —NR$_{11}$R$_{12}$, —(C0-C10)C(O)R$_{10}$, —(C0-C10)C(O)OR$_{10}$, —(C0-C10)OC(O)R$_{10}$, —(C1-C10)SR$_{10}$, —(C0-C10)C(O)NR$_{11}$R$_{12}$, —C(O)NHNR$_{11}$R$_{12}$ and —(C0-C10)OR$_{10}$;

wherein R$_{10}$, R$_{11}$ and R$_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;
or a pharmaceutically salt thereof or solvate thereof.

In certain preferred embodiments of the compounds according to formula (IC), the bond between C$_{10}$ and C$_{11}$ is a double bond.

In certain preferred embodiments of the compounds according to formula (IC), R$_3$ is H.

In certain preferred embodiments of the compounds according to formula (IC), R$_8$ is H.

In certain preferred embodiments of the compounds according to formula (IC), R$_7$ is selected from the group consisting of substituted or unsubstituted C6-C10alkyl, substituted or unsubstituted C5-C8cycloalkyl, substituted or unsubstituted C6-C10alkenyl, substituted or unsubstituted C4-C8cycloalkenyl, substituted or unsubstituted aryl, substituted or unsubstituted heteroaryl, —(C6-C10)OH, —NR$_{11}$R$_{12}$, —(C6-C10)C(O)R$_{10}$, —(C6-C10)C(O)OR$_{10}$, —(C0-C10)OC(O)R$_{10}$, —(C6-C10)SR$_{10}$, —(C6-C10)C(O)NR$_{11}$R$_{12}$, —C(O)NHNR$_{11}$R$_{12}$ and —(C6-C10)OR$_{10}$;

wherein R$_{10}$, R$_{11}$ and R$_{12}$ independently from each other are selected from the group consisting of substituted or unsubstituted C$_6$-C10alkyl, substituted or unsubstituted C5-C8cycloalkyl, substituted or unsubstituted C6-C10alkenyl, substituted or unsubstituted C4-C8cycloalkenyl, substituted or unsubstituted aryl and substituted or unsubstituted heteroaryl.

In certain preferred embodiments of the compounds according to formula (IC), the bond between C$_{10}$ and C$_{11}$ is a double bond, R$_2$ is unsubstituted C1-C3alkyl, R$_3$ is H, R$_4$ is unsubstituted C1-C3alkyl, R$_7$ is unsubstituted C1-C3alkyl, R$_8$ is H and R$_9$ is unsubstituted C1-C3alkyl. In certain even more preferred embodiments of the compounds according to formula (IC), the bond between C$_{10}$ and C$_{11}$ is a double bond, R$_2$ is unsubstituted C1-C3alkyl, R$_3$ is H, R$_8$ is H, R$_9$ is unsubstituted C1-C3alkyl and R$_4$ and/or R$_7$ is methyl.

In certain preferred embodiments of the compounds according to formula (IC), the bond between C$_{10}$ and C$_{11}$ is a double bond, R$_2$ is unsubstituted C1-C3alkyl, R$_3$ is H, R$_7$ is unsubstituted C1-C3alkyl, R$_8$ is H and R$_9$ is unsubstituted C1-C3alkyl. The present invention in certain embodiments comprises compounds of the general formula (ID):

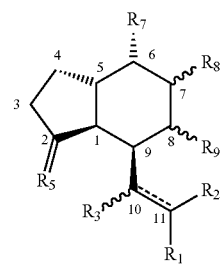

(ID)

wherein
the dotted line between C$_{10}$ and C$_{11}$ represents an optional double bond;

$R_1$ is selected from the group consisting of substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl, substituted or unsubstituted heteroaryl, —(C0-C10)C(O)$R_{10}$, —(C0-C10)C(O)O$R_{10}$, —(C0-C10)OC(O)$R_{10}$, —(C1-C10)S$R_{10}$, —(C0-C10)C(O)N$R_{11}R_{12}$, —(C0-C10)C(O)NHN$R_{11}R_{12}$ and —(C1-C10)O$R_{10}$;
  wherein $R_{10}$, $R_{11}$ and $R_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;
$R_2$, $R_3$, $R_7$, $R_8$ and $R_9$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl, substituted or unsubstituted heteroaryl, —CN, —(C1-C10)OH, —N$R_{11}R_{12}$, —(C0-C10)C(O)$R_{10}$, —(C0-C10)C(O)O$R_{10}$, —(C0-C10)OC(O)$R_{10}$, —(C1-C10)S$R_{10}$, —(C0-C10)C(O)N$R_{11}R_{12}$, —C(O)NHN$R_{11}R_{12}$ and —(C0-C10)O$R_{10}$;
  wherein $R_{10}$, $R_{11}$ and $R_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;
$R_5$ is selected from the group consisting of O and CH$R_{13}$;
  wherein $R_{13}$ is selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;
or a pharmaceutically salt thereof or solvate thereof.

In certain preferred embodiments of the compounds according to formula (ID), the bond between $C_{10}$ and $C_{11}$ is a double bond.

In certain preferred embodiments of the compounds according to formula (ID), $R_3$ is H.

In certain preferred embodiments of the compounds according to formula (ID), $R_8$ is H.

In certain preferred embodiments of the compounds according to formula (ID), $R_7$ is selected from the group consisting of substituted or unsubstituted C6-C10alkyl, substituted or unsubstituted C5-C8cycloalkyl, substituted or unsubstituted C6-C10alkenyl, substituted or unsubstituted C4-C8cycloalkenyl, substituted or unsubstituted aryl, substituted or unsubstituted heteroaryl, —(C6-C10)OH, —N$R_{11}R_{12}$, —(C6-C10)C(O)$R_{10}$, —(C6-C10)C(O)O$R_{10}$, —(C0-C10)OC(O)$R_{10}$, —(C6-C10)S$R_{10}$, —(C6-C10)C(O)N$R_{11}R_{12}$, —C(O)NHN$R_{11}R_{12}$ and —(C6-C10)O$R_{10}$;
  wherein $R_{10}$, $R_{11}$ and $R_{12}$ independently from each other are selected from the group consisting of substituted or unsubstituted C6-C10alkyl, substituted or unsubstituted C5-C8cycloalkyl, substituted or unsubstituted C6-C10alkenyl, substituted or unsubstituted C4-C8cycloalkenyl, substituted or unsubstituted aryl and substituted or unsubstituted heteroaryl.

In certain preferred embodiments of the compounds according to formula (ID), the bond between $C_{10}$ and $C_{11}$ is a double bond, $R_2$ is unsubstituted C1-C3alkyl, $R_3$ is H, $R_7$ is unsubstituted C1-C3alkyl, $R_8$ is H and $R_9$ is unsubstituted C1-C3alkyl. In certain even more preferred embodiments of the compounds according to formula (ID), the bond between $C_{10}$ and $C_{11}$ is a double bond, $R_2$ is unsubstituted C1-C3alkyl, $R_3$ is H, $R_8$ is H, $R_9$ is unsubstituted C1-C3alkyl and $R_4$ and/or $R_7$ is methyl.

In certain preferred embodiments of the compounds according to formula (ID), the bond between $C_{10}$ and $C_{11}$ is a double bond, $R_2$ is unsubstituted C1-C3alkyl, $R_3$ is H, $R_7$ is unsubstituted C1-C3alkyl, $R_8$ is H and $R_9$ is unsubstituted C1-C3alkyl.

In certain preferred embodiments of formula (I), (IA1), (IA2), (IB), (IC) and/or (ID) (and especially of formula (IA1)) $R_3$, $R_8$ and $R_9$ are hydrogen, $R_2$, $R_4$ and $R_7$ are methyl, the C10-C11 carbon-carbon bond is a double bond and $R_1$ is selected from substituted or unsubstituted alkyl, —C(O)$R_{10}$, —C(O)O$R_{10}$, —(Cl)S$R_{10}$, —C(O)N$R_{11}R_{12}$, —C(O)NHN$R_{11}R_{12}$ and —(Cl)O$R_{10}$, wherein $R_{10}$, $R_{11}$ and $R_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl; preferably $R_3$, $R_8$ and $R_9$ are hydrogen, $R_2$, $R_4$ and $R_7$ are methyl, the C10-C11 carbon-carbon bond is a double bond and $R_1$ is selected from —C(O)$R_{10}$, —C(O)O$R_{10}$, —C(O)N$R_{11}R_{12}$ and —C(O)NHN$R_{11}R_{12}$, wherein $R_{10}$, $R_{11}$ and $R_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl; more preferred $R_3$, $R_8$ and $R_9$ are hydrogen, $R_2$, $R_4$ and $R_7$ are methyl, the C10-C11 carbon-carbon bond is a double bond and $R_1$ is selected from —C(O)O$R_{10}$ and —C(O)N$R_{11}R_{12}$, wherein $R_{10}$, $R_{11}$ and $R_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl; even more preferred $R_3$, $R_8$ and $R_9$ are hydrogen, $R_2$, $R_4$ and $R_7$ are methyl, the C10-C11 carbon-carbon bond is a double bond and $R_1$ is selected from —C(O)N$R_{11}R_{12}$, wherein $R_{11}$ and $R_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl. In specific preferred embodiments of the aforementioned compounds according to formula (I), (IA1), (IA2), (IB), (IC) and/or (ID) $R_6$ is hydrogen. Examples of compounds falling under the scope of the aforementioned compounds are the carboxamides of the valerenic acid, wherein valerenic acid amide (VA-A) is one specific example of these carboxamides.

In certain preferred embodiments the compounds are selected from compounds according to formula (I), (IA1), (IA2), (IB), (IC) and/or (ID), wherein the compounds comprise at least one heteroatom beside oxygen. In certain more preferred embodiments the compounds are selected from compounds according to formula (I), (IA1), (IA2), (IB), (IC) and/or (ID), wherein $R_1$ or $R_2$ of the compounds comprise at least one functional group comprising nitrogen, especially an amine, an amide, a nitro, an imine, an imide, an azide, an azo, a cyanate, an isocyanate, a cyano, a nitrile, a nitrite, a nitroso or a N-heterocyclic group, especially an amine, an amide or an N-heterocyclic group. In specific preferred embodiments the at least one functional group comprising nitrogen is an amide group, preferably a carboxamide group.

In certain preferred embodiments, the compounds according to formula (I) are selected from the group of compounds comprising (E)-3-((4S,7R,7aR)-3,7-dimethyl-2,4,5,6,7,7a-hexahydro-1H-inden-4-yl)-2-methylacrylamide (VA-A), (E)-3-((4S,7R,7aR)-3,7-dimethyl-2,4,5,6,7,7a-hexahydro-1H-inden-4-yl)-2-methylacrylohydrazide (VA-HY), (E)-3-((4S,7R,7aR)-3,7-dimethyl-2,4,5,6,7,7a-hexahydro-1H-inden-4-yl)-N,2-dimethylacrylamide (VA-MA), (E)-3-((4S,7R,7aR)-3,7-dimethyl-2,4,5,6,7,7a-hexahydro-1H-inden-4-yl)-N,N,2-trimethylacrylamide (VA-DMA), (E)-3-((4S,7R,7aR)-3,7-dimethyl-2,4,5,6,7,7a-hexahydro-1H-inden-4-yl)-N,N-diethyl-2-methylacrylamide (VA-DEA), (E)-3-((4S,7R,7aR)-3,7-dimethyl-2,4,5,6,7,7a-hexahydro-1H-inden-4-yl)-N-isopropyl-2-methylacrylamide (VA-IPA), (E)-N-butyl-3-((4S,7R,7aR)-3,7-dimethyl-2,4,5,6,7,7a-hexahydro-1H-inden-4-yl)-2-methylacrylamide (VA-BA), (E)-3-((4S,7R,7aR)-3,7-dimethyl-2,4,5,6,7,7a-hexahydro-1H-inden-4-yl)-2-methyl-1-morpholinoprop-2-en-1-one (VA-MO), (E)-3-((4S,7R,7aR)-3,7-dimethyl-2,4,5,6,7,7a-hexahydro-1H-inden-4-yl)-2-methyl-1-(piperidin-1-yl)prop-2-en-1-one (VA-PIP). In certain more preferred embodiments, the compounds according to formula (I) are selected from the group of compounds comprising (E)-3-[(4S,7R,7aR)-3,7-dimethyl-2,4,5,6,7,7a-hexahydro-1H-inden-4-yl]-2-methylprop-2-enamide (VA-A) and (E)-3-[(4S,7R,7aR)-3,7-dimethyl-2,4,5,6,7,7a-hexahydro-1H-inden-4-yl]-2-methylprop-2-en hydrazide (VA-HY):

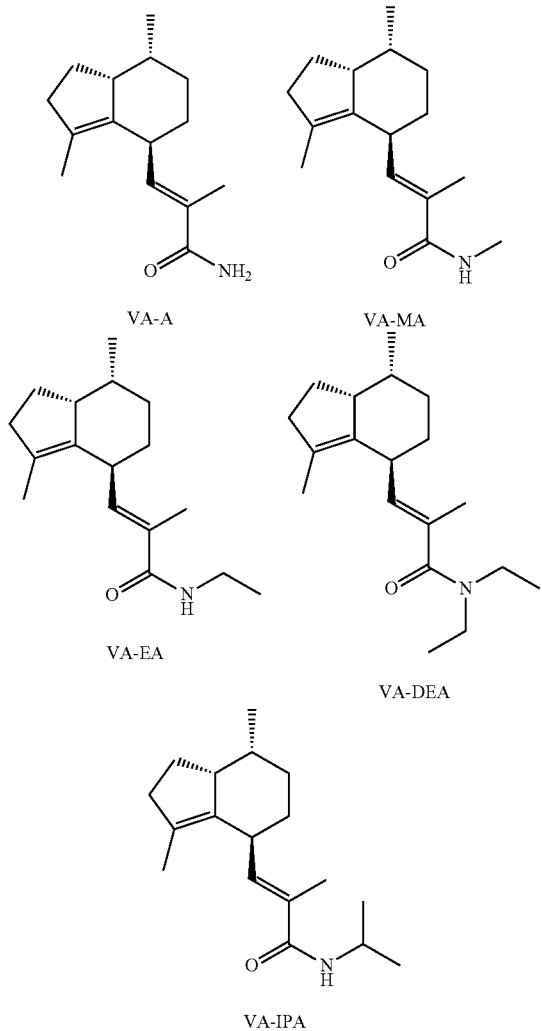

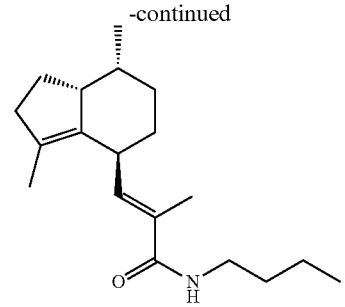

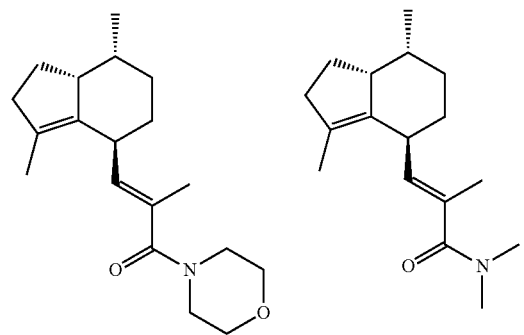

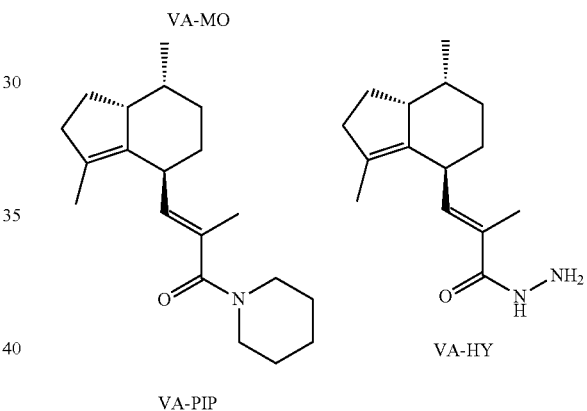

The compounds of the present invention can be comprised in a pharmaceutical composition in a pharmaceutically effective amount.

The compounds of the present invention can be used for the manufacture of a medicament for the treatment of anxiety and/or insomnia.

Furthermore, the compounds of the present invention can be used for the manufacture of a medicament for modulating a pharmacological response from the $GABA_A$-receptor.

In order to avoid potential undesirable properties, such as bitter taste, poor absorption, poor solubility, and especially in order to enhance oral delivery or membrane permeability of the inventive compounds, the compounds or drugs according to the present invention may be administered or used as prodrugs or in form of prodrugs, especially ester prodrugs such as lipophilic ester prodrugs. It is to be noted that the inventive compounds may represent a prodrug of the actually active agent or that the inventive compounds may represent the active agent and are transformed into prodrugs, e.g. by adding an ester group. Thus, in certain preferred embodiments of the present invention, the inventive compounds are prodrugs or in the form of prodrugs, wherein the prodrugs preferably are ester prodrugs. For example, such prodrugs or inventive compounds in the form of prodrugs may be selected from compounds according to formula (I), wherein $R_1$ is —COOR$_{16}$ and $R_{16}$ is selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl or represents another group known to the skilled person for the use as prodrug. The inventive compounds according to preferred embodiments of the invention are comprised in the form of an ester prodrug in a pharmaceutical composition in a pharmaceutically effective amount and may be used in the form of an ester prodrug for the manufacture of a medicament for the treatment of anxiety and/or insomnia and/or may be used in the form of an ester prodrug for the manufacture of a medicament for modulating a pharmacological response from the GABA$_A$-receptor. In certain preferred embodiments the prodrugs are double ester prodrugs, comprising a double ester group such as —COO—Z—OOC—R$_{15}$, wherein R$_{15}$ is selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted C1-C10 alkoxy, substituted or unsubstituted aryl and substituted or unsubstituted heteroaryl, and Z is selected from substituted or unsubstituted C1-C10alkylen. Preferably, R$_{15}$ is a substituted or unsubstituted C1-C10 alkyl and Z is a substituted or unsubstituted C1alkylen. A preferred prodrug is selected from compounds according to formula (I), wherein $R_1$ is —COO—CH$_2$—OOC$^t$Bu. The skilled person may use such ester prodrugs, especially double ester prodrugs, inter alia to enhance the lipophilicity and increase penetration of the blood-brain barrier. After penetration of the blood-brain barrier the ester group is cleaved off by esterase to expose the drug in the central nervous system (brain).

The use or manufacture of corresponding prodrugs inter alia aims at providing hydrophilicity or lipophilicity, providing site-directed delivery, increasing absorption, relieving pain of the injection site, decreasing toxicity, decreasing metabolic inactivation, increasing chemical stability, modifying the time of action, masking groups, such as hydrogen bonding groups of the inventive active compounds by the addition of an ester-moiety, and/or increasing permeability of the blood-brain barrier. The methods for achieving such effects and synthesizing corresponding prodrug esters starting from the inventive compounds or drugs are well known to the skilled person.

A specific group of compounds according to the present invention that may be comprised in a pharmaceutical composition in a pharmaceutically effective amount and/or may be used for the manufacture of a medicament for the treatment of anxiety and/or insomnia and/or may be used for the manufacture of a medicament for modulating a pharmacological response from the GABA$_A$-receptor are compounds according to formula (IA1); preferably compounds according to formula (IA1) wherein $R_3$, $R_8$ and $R_9$ are hydrogen, $R_2$, $R_4$ and $R_7$ are methyl, the C10-C11 carbon-carbon bond is a double bond and $R_1$ is selected from substituted or unsubstituted alkyl, —C(O)R$_{10}$, —C(O)OR$_{10}$, —(Cl)SR$_{10}$, —C(O)NR$_{11}$R$_{12}$, —C(O)NHNR$_{11}$R$_{12}$ and —(Cl)OR$_{10}$, wherein R$_{10}$, R$_{11}$ and R$_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl; more preferred compounds according to formula (IA1) wherein R$_3$, R$_8$ and R$_9$ are hydrogen, R$_2$, R$_4$ and R$_7$ are methyl, the C10-C11 carbon-carbon bond is a double bond and $R_1$ is selected from —C(O)R$_{10}$, —C(O)OR$_{10}$, —C(O)NR$_{11}$R$_{12}$ and —C(O)NHNR$_{11}$R$_{12}$, wherein R$_{10}$, R$_{11}$ and R$_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl; even more preferred compounds according to formula (IA1) wherein R$_3$, R$_8$ and R$_9$ are hydrogen, R$_2$, R$_4$ and R$_7$ are methyl, the C10-C11 carbon-carbon bond is a double bond and $R_1$ is selected from —C(O)OR$_{10}$ and —C(O)NR$_{11}$R$_{12}$, wherein R$_{10}$, R$_{11}$ and R$_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl; most preferred compounds according to formula (IA1) wherein R$_3$, R$_8$ and R$_9$ are hydrogen, R$_2$, R$_4$ and R$_7$ are methyl, the C10-C11 carbon-carbon bond is a double bond and $R_1$ is selected from —C(O)NR$_{11}$R$_{12}$, wherein R$_{11}$ and R$_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl. More specific groups of compounds refer to the aforementioned compounds according to formula (IA1) that are additionally specified by R$_6$ is hydrogen. An example of a group of aforementioned compounds that may be used in this context are the carboxamides of the valerenic acid, wherein valerenic acid amide is one specific compound that may be used in this context.

According to another aspect of the present invention a process for the preparation of compound (9) having the following structure is provided:

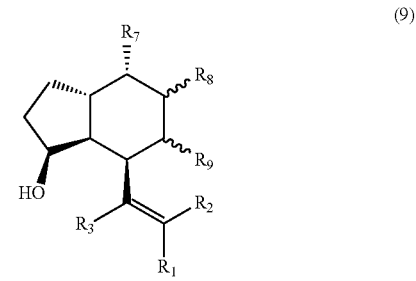

(9)

In certain preferred embodiments the process comprises the following steps:

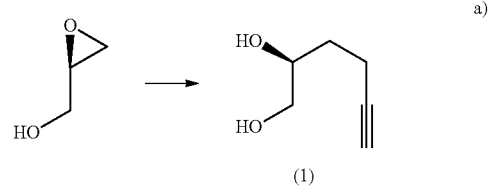

a)

(1)

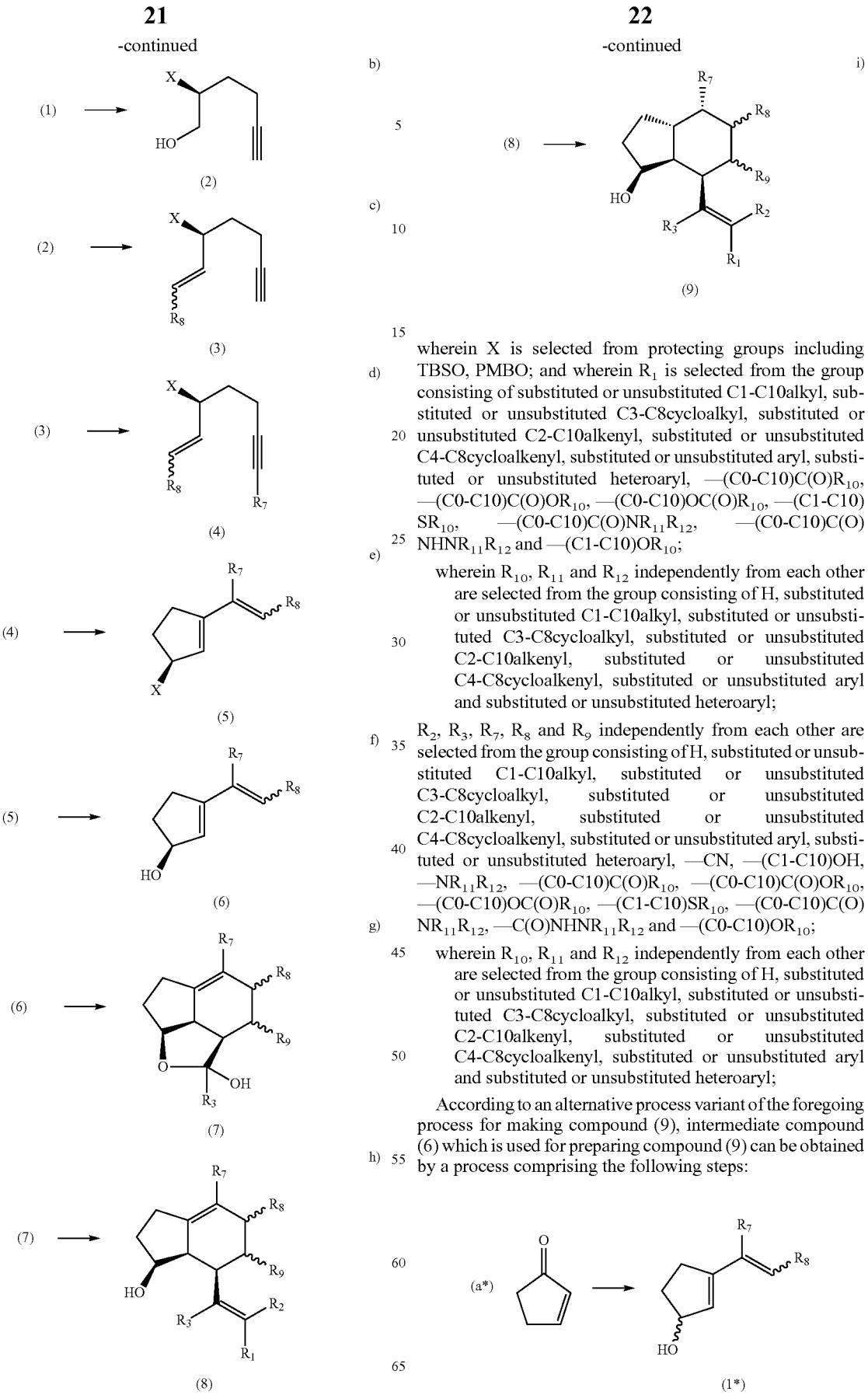

wherein X is selected from protecting groups including TBSO, PMBO; and wherein $R_1$ is selected from the group consisting of substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl, substituted or unsubstituted heteroaryl, —(C0-C10)C(O)$R_{10}$, —(C0-C10)C(O)O$R_{10}$, —(C0-C10)OC(O)$R_{10}$, —(C1-C10)S$R_{10}$, —(C0-C10)C(O)N$R_{11}R_{12}$, —(C0-C10)C(O)NHN$R_{11}R_{12}$ and —(C1-C10)O$R_{10}$;

wherein $R_{10}$, $R_{11}$ and $R_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;

$R_2$, $R_3$, $R_7$, $R_8$ and $R_9$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl, substituted or unsubstituted heteroaryl, —CN, —(C1-C10)OH, —N$R_{11}R_{12}$, —(C0-C10)C(O)$R_{10}$, —(C0-C10)C(O)O$R_{10}$, —(C0-C10)OC(O)$R_{10}$, —(C1-C10)S$R_{10}$, —(C0-C10)C(O)N$R_{11}R_{12}$, —C(O)NHN$R_{11}R_{12}$ and —(C0-C10)O$R_{10}$;

wherein $R_{10}$, $R_{11}$ and $R_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;

According to an alternative process variant of the foregoing process for making compound (9), intermediate compound (6) which is used for preparing compound (9) can be obtained by a process comprising the following steps:

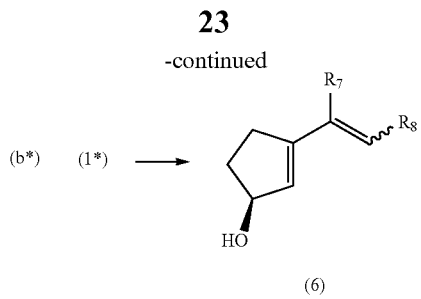

The substituents $R_7$ and $R_8$ correspond to substituents $R_7$ and $R_8$ mentioned above in the context with the inventive process for making compound (9).

Compound (9) may then be used as starting compound in order to prepare some of the compounds of the present invention.

Thus, the present invention in certain embodiments comprises a process starting from compound (9) for the preparation of compound (IA2) having the following structure:

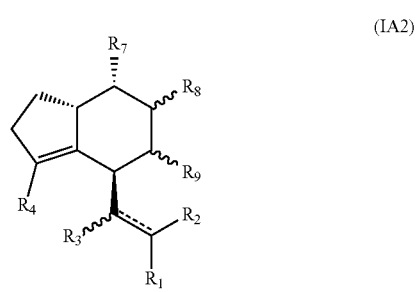

Said process comprises in certain preferred embodiments the following steps:

wherein X' is selected from protecting groups including TfO, AcO.

Also, the present invention in certain embodiments comprises a process starting from compound (9) for the preparation of compound (IB) having the following structure:

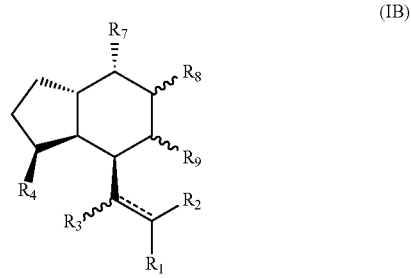

Said process comprises in certain preferred embodiments the following steps:

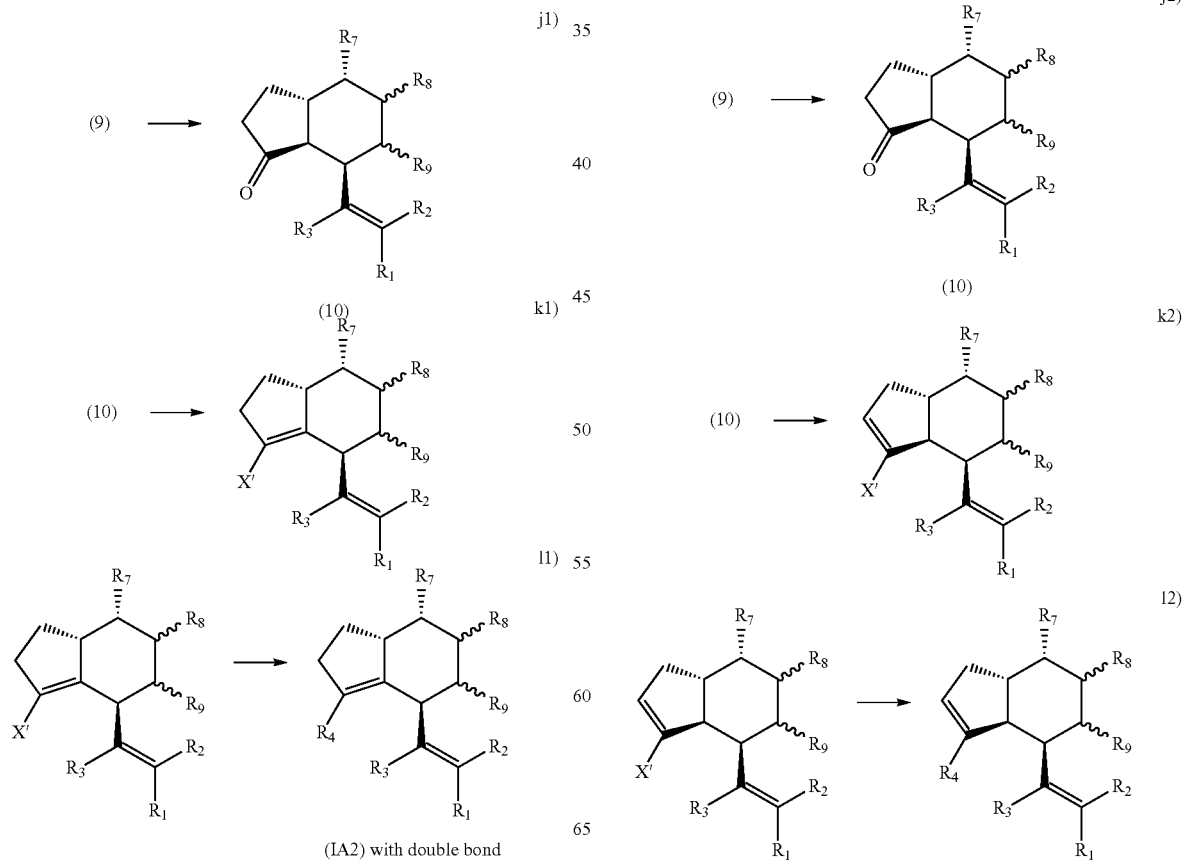

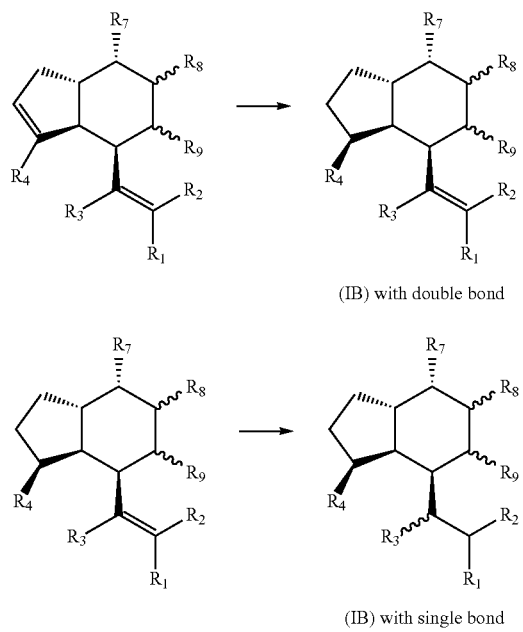

(IB) with double bond

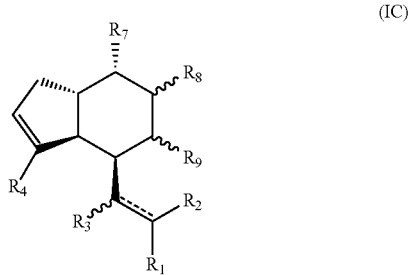

(IB) with single bond wherein X' is selected from protecting groups including TfO, AcO.

Further, the present invention in certain embodiments comprises a process starting from compound (9) for the preparation of compound (IC) having the following structure:

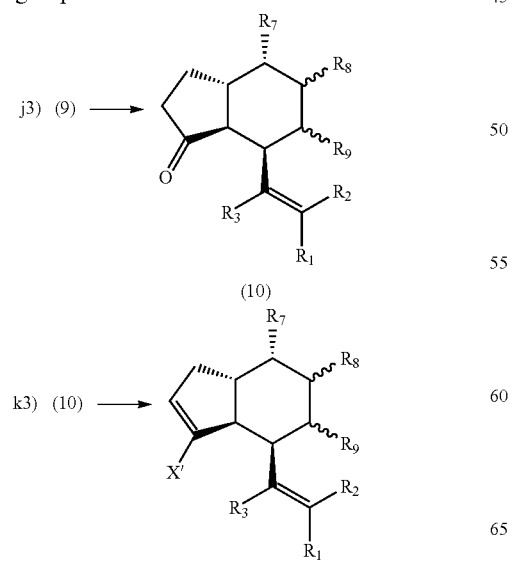

Said process comprises in certain preferred embodiments the following steps:

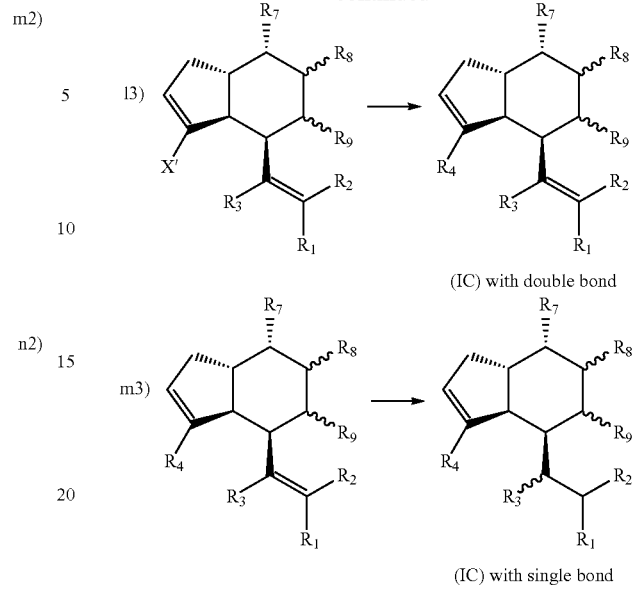

(IC) with double bond

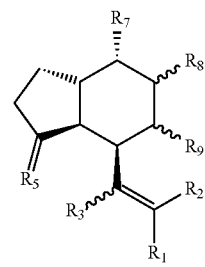

(IC) with single bond wherein X' is selected from protecting groups including TfO, AcO.

Furthermore, the present invention in certain embodiments comprises a process starting from compound (9) for the preparation of compound (ID) having the following structure:

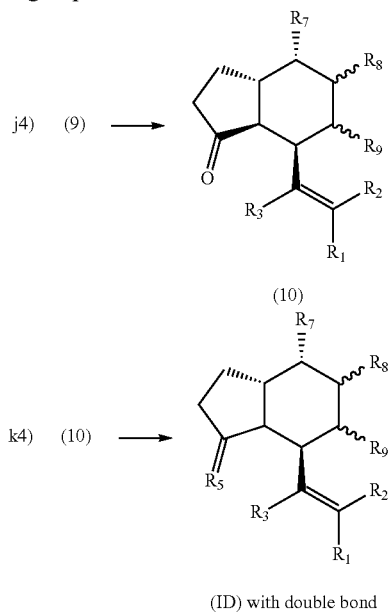

Said process comprises in certain preferred embodiments the following steps:

-continued
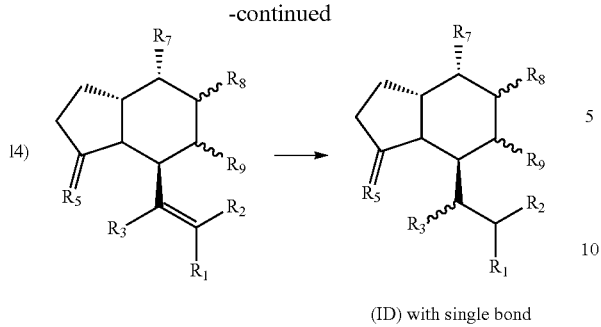
(ID) with single bond
According to another aspect, the present invention also refers to a process for the preparation of valerenic acid having the following structure:
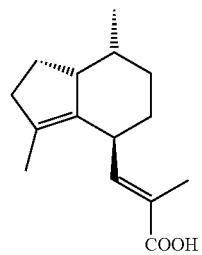
Said process comprises in certain preferred embodiments the following steps:
a') 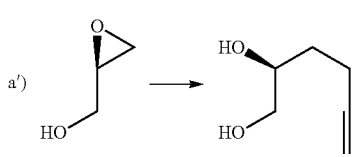
(1)
b') (1) ⟶ 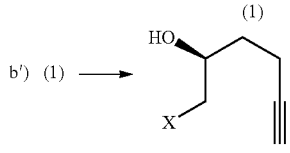
(2a)
c') (2a) ⟶ 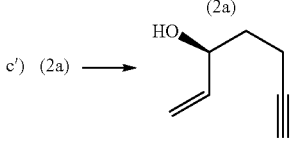
(3a)
d') (3a) ⟶ 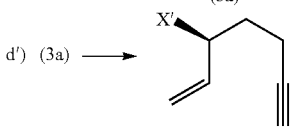
(4a)
e') (4a) ⟶ 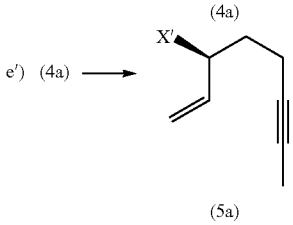
(5a)
f') (5a) ⟶ 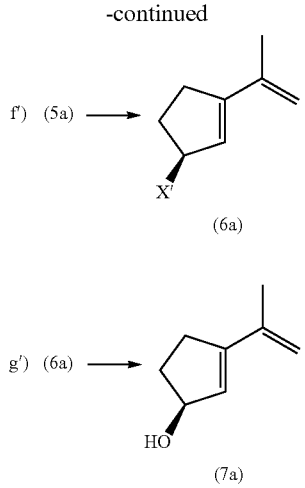
(6a)
g') (6a) ⟶ 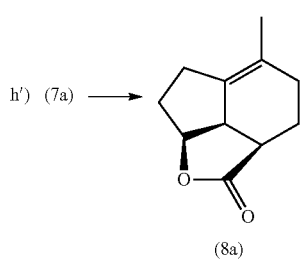
(7a)
h') (7a) ⟶ 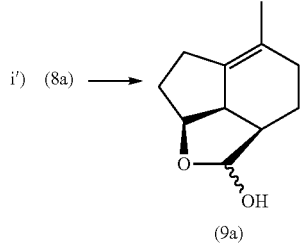
(8a)
i') (8a) ⟶ 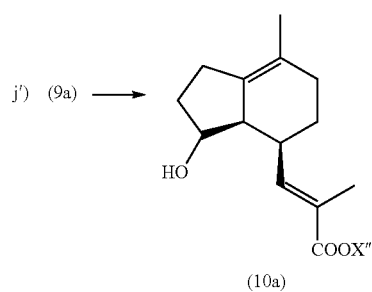
(9a)
j') (9a) ⟶ 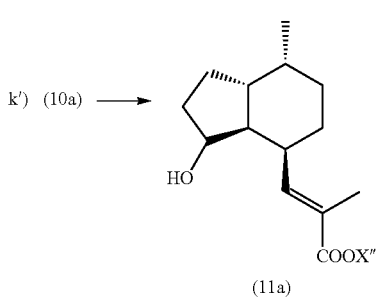
(10a)
k') (10a) ⟶
(11a)

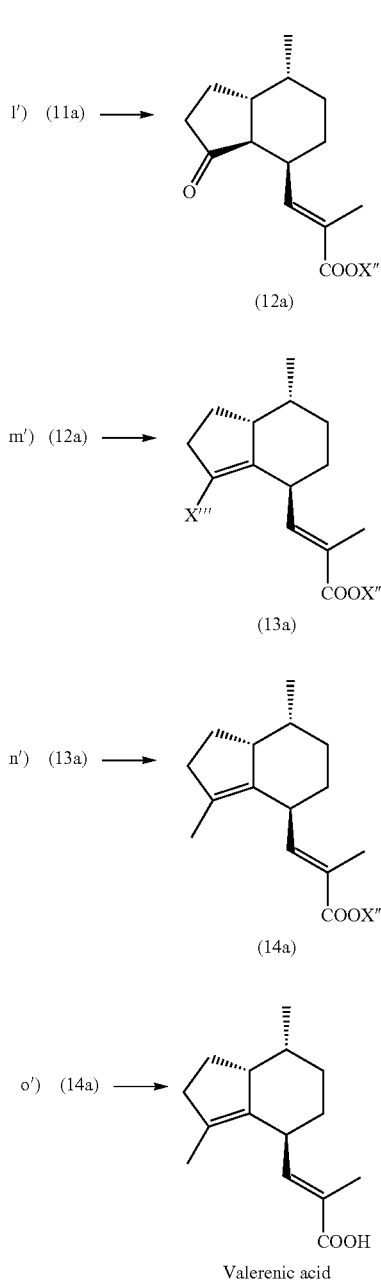

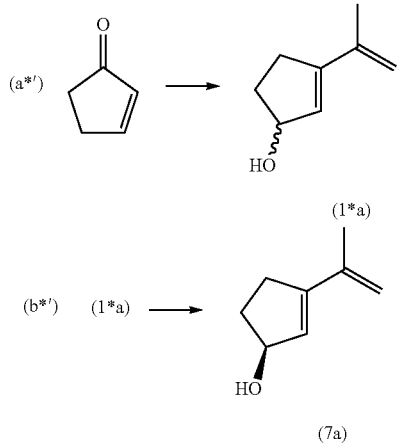

DETAILED DESCRIPTION OF THE PRESENT INVENTION

1. Definitions

Figure 1:
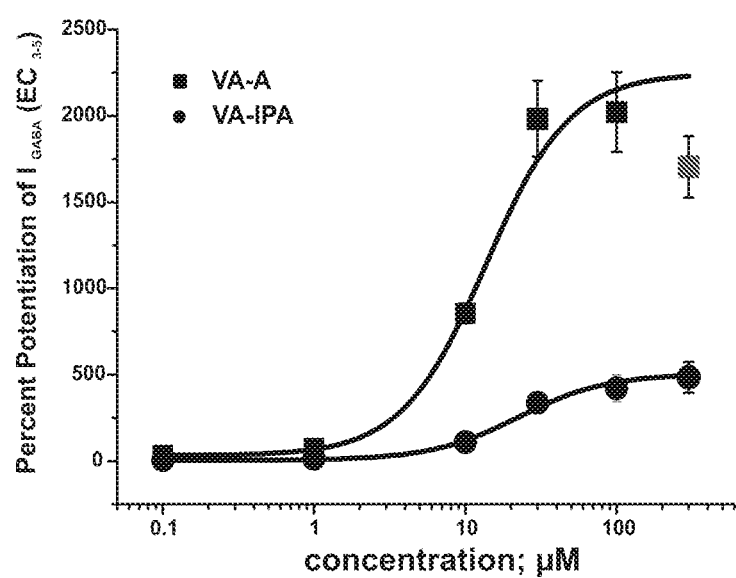
FIG. 1: Concentration-response curves for the indicated compounds VA-IPA and VA-A on $\alpha_1\beta_3$ receptors using a GABA $EC_{3-5}$. Data points represent means±S.E. from at least 4 oocytes from ≥2 batches.

The following definitions are used in connection with the present invention and especially the valerenic acid derivatives unless the context indicates otherwise:

The term "valerenic acid" as used herein corresponds to the natural compound and refers to a compound that has the following structure:

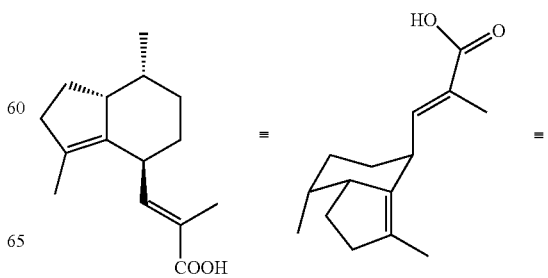

wherein X is selected from protecting groups including TsO, MsO;

wherein X' is selected from protecting groups including TBSO, PMBO;

wherein X" is e.g. selected from C1-C10alkyl, C2-C10alkenyl, substituted or unsubstituted aryl;

wherein X''' is selected from protecting groups including TfO and AcO.

According to an alternative process variant of the foregoing process for making valerenic acid (9a), intermediate compound (7a) which is used for preparing valerenic acid (9a) can be obtained by a process comprising the following steps:

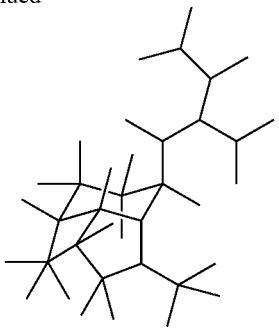

The IUPAC name of valerenic acid is (E)-3-[(4S,7R,7aR)-3,7-dimethyl-2,4,5,6,7,7a-hexahydro-1H-inden-4-yl]-2-methylprop-2-enoic acid.

Regarding the compounds of the present application, the bond between $C_{10}$ and $C_{11}$ is an optional double bond. Said bond is referred to with the term "the dotted line between $C_{10}$ and $C_{11}$ represents an optional double bond" with the following structural element depicted in the formulas:

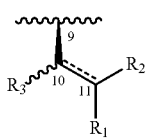

The bond between $C_{10}$ and $C_{11}$ can thus either be a single bond as depicted in the following:

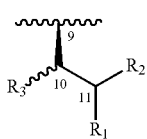

Alternatively, the bond between $C_{10}$ and $C_{11}$ can be a double bond as depicted in the following:

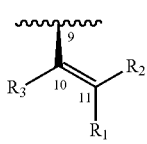

In general, the number of carbon atoms present in a given group is designated "Cx-Cy" where x and y are the lower and upper limits, respectively. For example, a group designated as "C1-C6" contains from 1 to 6 carbon atoms. The carbon number as used in the definitions herein refers to carbon backbone and carbon branching, but does not include carbon atoms of the substituents. General examples of alkyl groups include methyl, propyl, isopropyl, butyl, n-butyl, isobutyl, sec-butyl, tert-butyl, and pentyl.

"Carbon branching" or "branched alkyl" means that one or more alkyl groups such as methyl, ethyl or propyl, replace one or both hydrogens in a —CH$_2$— group of a linear alkyl chain.

The term "alkyl" refers to a hydrocarbon chain that may be a straight chain or branched chain, containing the indicated number of carbon atoms. For example, C1-C10 indicates that the group may have from 1 to 10 (inclusive) carbon atoms in it.

For example, the term "C1-C3 alkyl" refers to a straight or branched chain saturated hydrocarbon containing 1-3 carbon atoms. Examples of a C1-C3 alkyl group include, but are not limited to, methyl, ethyl, propyl and isopropyl. C1-C3 alkyl groups can be referred to as "lower alkyls".

For example, the term "C6-C10 alkyl" refers to a straight or branched chain saturated hydrocarbon containing 6-10 carbon atoms. Examples of a C6-C10 alkyl group include, but are not limited to hexyl, octyl and decyl.

The term "cycloalkyl" refers to a saturated cycloalkyl group. The term "C3-C8 cycloalkyl", for example, refers to a non-aromatic mono- or multicyclic hydrocarbon ring system having a single radical and 3-8 carbon atoms. Exemplary monocyclic cycloalkyl rings include cyclopropyl, cyclopentyl, and cyclohexyl.

The term "alkenyl" refers to a straight or branched chain unsaturated hydrocarbon. The term "C2-C10 alkenyl" refers to a straight or branched chain unsaturated hydrocarbon containing 2-10 carbon atoms and at least one double bond. Examples of a C2-C10 alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, 1-octene, 2-octene, 3-octene, 4-octene, 1-nonene, 2-nonene, 3-nonene, 4-nonene, 1-decene, 2-decene, 3-decene, 4-decene and 5-decene.

The term "cycloalkenyl" refers to an unsaturated cycloalkyl group. The term "C3-C8 cycloalkenyl" means a non-aromatic monocyclic or multicyclic hydrocarbon ring system containing a carbon-carbon double bond having a single radical and 3 to 8 carbon atoms. Exemplary monocyclic cycloalkenyl rings include cyclopropenyl, cyclopentenyl, cyclohexenyl or cycloheptenyl.

The term "aryl" refers to an aromatic hydrocarbon group. If not otherwise specified, in this specification the term aryl refers to a C6-C14 aryl group. Examples of an C6-C14 aryl group include, but are not limited to, phenyl, 1-naphthyl, 2-naphthyl, 3-biphen-1-yl, anthryl, tetrahydronaphthyl, fluorenyl, indanyl, biphenylenyl, and acenaphthenyl, groups.

The term "heteroaryl" refers to mono, bicyclic, and tricyclic aromatic groups of 5 to 13 atoms containing at least one heteroatom and at least one aromatic ring, if not specified otherwise. Heteroatom as used in the term heteroaryl refers to oxygen, sulfur and nitrogen. Examples of monocyclic heteroaryls include, but are not limited to pyrrolyl, oxazinyl, thiazinyl, pyridinyl, diazinyl, triazinyl, tetrazinyl, imidazolyl, tetrazolyl, isoxazolyl, furanyl, furazanyl, oxazolyl, thiazolyl, thiophenyl, pyrazolyl, triazolyl, and pyrimidinyl. Examples of bicyclic heteroaryls include but are not limited to, benzimidazolyl, indolyl, indolinyl, isoquinolinyl, quinolinyl, quinazolinyl, benzothiophenyl, benzodioxolyl, benzo[1,2,5]oxadiazolyl, purinyl, benzisoxazolyl, benzoxazolyl, benzthiazolyl, benzodiazolyl, benzotriazolyl, isoindolyl and indazolyl. Examples of tricyclic heteroaryls include but are not limited to, dibenzofuran, dibenzothiophenyl, phenanthridinyl, and benzoquinolinyl.

The term "substituted" as used herein refers to substituted moieties (including substituted C1-C10alkyl or substituted C6-C10alkyl, substituted C3-C8cycloalkyl or substituted C5-C8cycloalkyl, substituted C2-C10alkenyl or substituted C6-C10alkenyl, substituted C4-C8cycloalkenyl, substituted aryl and substituted heteroaryl) bearing one or more of the following groups or substituents: halogen, —C1-C6alkyl, —C1-C6alkenyl, -hydroxyl, —NH$_2$, —NH(C1-C6alkyl), —N(C1-C6alkyl)(C1-C6alkyl), —N(C1-C3alkyl)C(O)(C1-C6alkyl), —NHC(O)(C1-C6alkyl), —NHC(O)H, —C(O)NH$_2$, —C(O)NH(C1-C6alkyl), —C(O)N(C1-C6alkyl)(C1-

C6alkyl), —CN, CHN(C1-C6alkyl), —O(C1-C6alkyl), —C(O)OH, —C(O)O(C1-C6alkyl), —(C1-C6alkyl)C(O)O (C1-C6alkyl), —C(O)(C1-C6alkyl), —C6-C14aryl, —C5-C9heteroaryl, —C3-C8cycloalkyl, -haloalkyl, -aminoalkyl, —OC(O)(C1-C6alkyl), —C1-C6carboxyamidoalkyl and/or —NO$_2$. Preferably, the substituted moieties solely comprise groups or substituents selected from the aforementioned groups or substituents and hydrogen.

The term "halogen" includes fluoride, bromide, chloride or iodide.

The term "halo" means —F, —Cl, —Br or —I. An exemplary haloalkyl includes trifluoromethyl.

The invention disclosed herein is meant to encompass all pharmaceutically acceptable salts of the disclosed compounds. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, fumarate, tartrate and the like; sulfonates such as methanesulfonate, benzenesulfonate, p-toluenesulfonate, and the like; amino acid salts such as arginate, asparginate, glutamate and the like.

The term "prodrug" as used herein refers to a substance that is in vivo transformed into an active agent or an agent having a higher activity than the prodrug.

Some of the compounds disclosed herein may contain one or more asymmetric centers and may thus lead to enantiomers, diastereomers, and other stereoisomeric forms.

The present invention is also meant to encompass all such possible forms as well as their racemic and resolved forms and mixtures thereof, unless specified otherwise. When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule.

In the context of the present invention, the terms "about" and "approximately" denote an interval of accuracy that a person skilled in the art will understand to still ensure the technical effect of the feature in question. The term typically indicates a deviation from the indicated numerical value of +/−10% and preferably +/−5%.

The compounds of the present invention are useful for modulating a pharmacodynamic response from GABA$_A$ receptors. The response can be attributed to the compound stimulating (agonist) or inhibiting (antagonist) the GABA$_A$ receptors. This can depend on the subunit composition of the GABA$_A$ receptors.

The term "modulate" as used herein with respect to the GABA$_A$ receptors means the mediation of a pharmacodynamic response (e.g. a sedative effect) in a subject from (i) inhibiting or activating the receptor, or (ii) directly or indirectly affecting the normal regulation of the receptor activity. Compounds which mediate a pharmacodynamic response as explained above include agonists, antagonists, mixed agonists/antagonists and compounds which directly or indirectly affect regulation of the receptor activity.

2. Methods for Making Valerenic Acid and Valerenic Acid Derivatives

The present invention is also directed to methods for making valerenic acid and valerenic acid derivatives.

In the following paragraphs, general schemes for making valerenic acid and its derivatives will be outlined. It is important to note that obvious alternative routes may be used when making the compounds. Thus, before describing said general schemes, standard alternative routes known and applied by the person skilled in the art will be briefly discussed.

Whenever reference is made to a solvent and/or a preferred solvent, this does not exclude that further components are present in said solvent. Thus, a solvent may be comprised of a preferred solvent and optionally further components, such as e.g. water. When e.g. reference is made to a polar aprotic solvent, said polar aprotic solvent is comprised in the solvent which is used. Examples of suitable polar aprotic solvents include, but are not limited to N-methylpyrrolidone, dimethyl formamide, dimethyl acetamide, and dimethyl sulfoxide.

When a preferred reaction temperature is mentioned, this does not exclude the reaction to also occur at a different temperature, but preferably in a temperature range varying within 50%, preferably within 25% and most preferably within 15% of said preferred reaction temperature.

When a reaction mixture is cooled, this is preferably done by using an icebath. The reaction mixture is then cooled to a temperature below the actual temperature and preferably to a temperature as indicated in the schemes below. However, this does not exclude that the reaction mixture may be cooled to a temperature range above or below the preferred temperature, preferably varying within 50%, more preferably within 25% and most preferably within 15% of said preferred temperature.

When a reaction mixture is warmed, this is preferably done by using a heater. The reaction mixture is then heated to a temperature above the actual temperature and preferably to a temperature as indicated in the schemes below. However, this does not exclude that the reaction mixture may be warmed to a temperature range above or below the preferred temperature, preferably varying within 50%, more preferably within 25% and most preferably within 15% of said preferred temperature.

When the compounds used in the reaction scheme below comprise "bromide" or "chloride" or "iodine", the person skilled in the art knows that these compounds are interchangeable; the same applies to "bromo" or "chloro" or "iodo" and the reaction conditions may easily be adapted accordingly when interchanged.

Any steps as mentioned below referring to the extraction of a solution, washes of the extract(s), drying of the extract(s), concentration and/or chromatography purification are routine steps for the skilled person. They may be done as mentioned in the example section 4. below; however, alternative ways may also be used and/or steps omitted according to the desired yield and final product of each single reaction step.

Certain terms used in the reaction schemes below describe protecting groups and are abbreviated as follows: "TBS" for tert-butyldimethylsilyl, "PMB" for p-methoxybenzyl, "Tf" for triflate, "Ac" for acetate, "Ts" for tosylate and "Ms" for mesylate. In this respect it should be mentioned that a selection from a group of protecting groups is not meant to be exclusive, i.e. that further protecting groups known to the skilled person may also be used and such groups are also meant to fall within the scope in reactions schemes of the present invention.

Progress of any reaction as outlined in the schemes below can be monitored using conventional analytical techniques, including but not limited to liquid chromatography in conjunction with mass spectroscopy ("LC/MS"), thin-layer chromatography ("TLC"), high-performance liquid chromatography ("HPLC"), gas chromatography ("GC"), gas-liquid chromatography ("GLC"), and/or nuclear magnetic resonance spectroscopy ("NMR"), such as $^1$H and $^{13}$C NMR.

2.1. Methods for Making Valerenic Acid

The general reaction schemes for the synthesis of valerenic acid follow the steps as depicted in Scheme 1 or Scheme 2 below. The inventive synthesis routes allow for the stereoselective preparation of valerenic acid.

General descriptions of how to synthesize the individual compounds of said schemes are described below.

Finally, detailed descriptions of embodiments of the invention for making valerenic acid are described below and in the example-section of the present description.

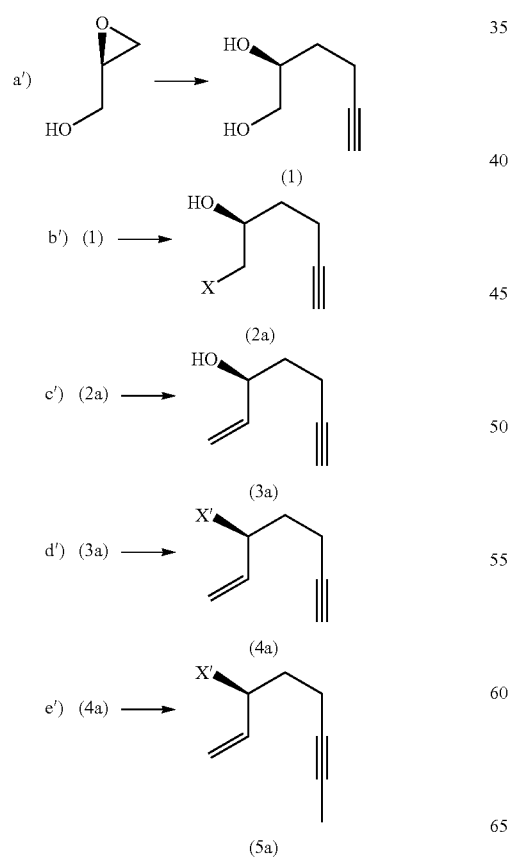

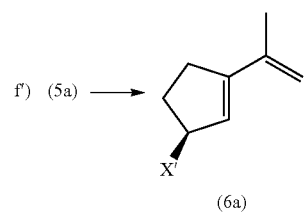

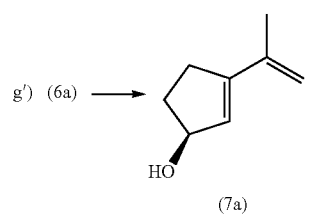

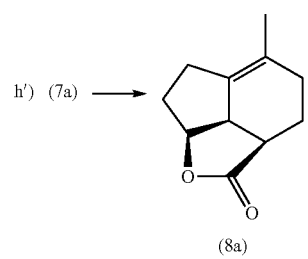

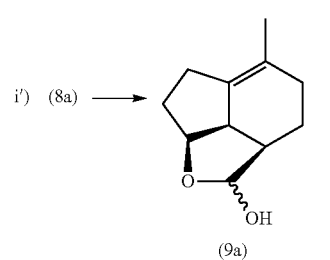

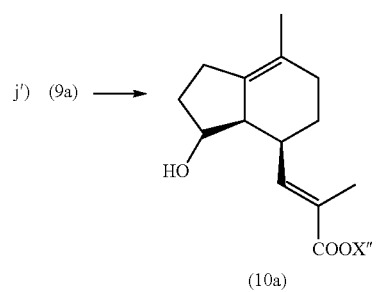

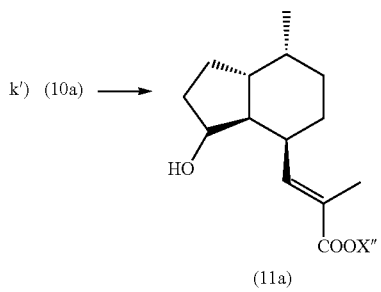

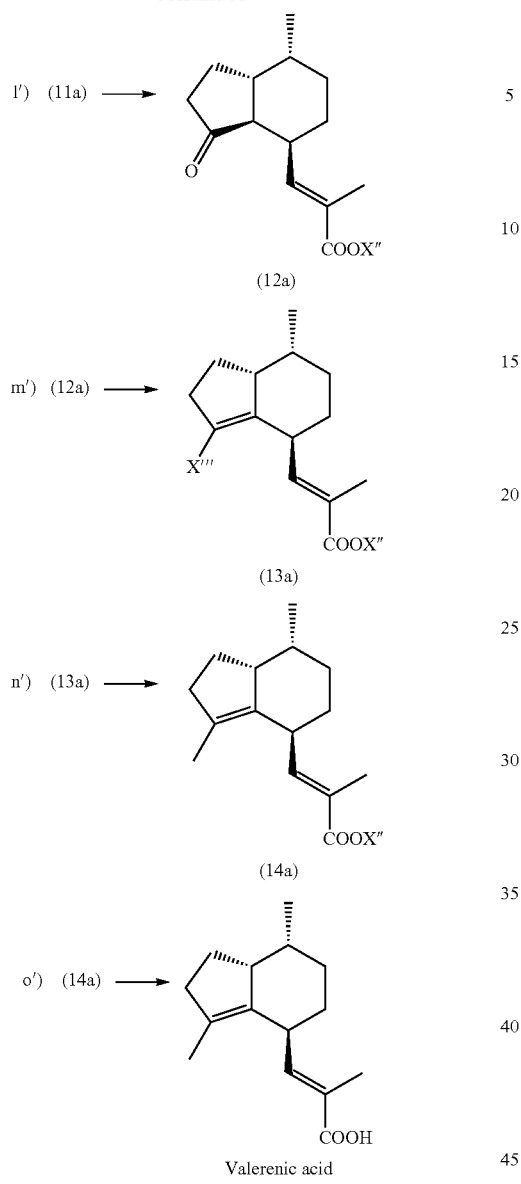
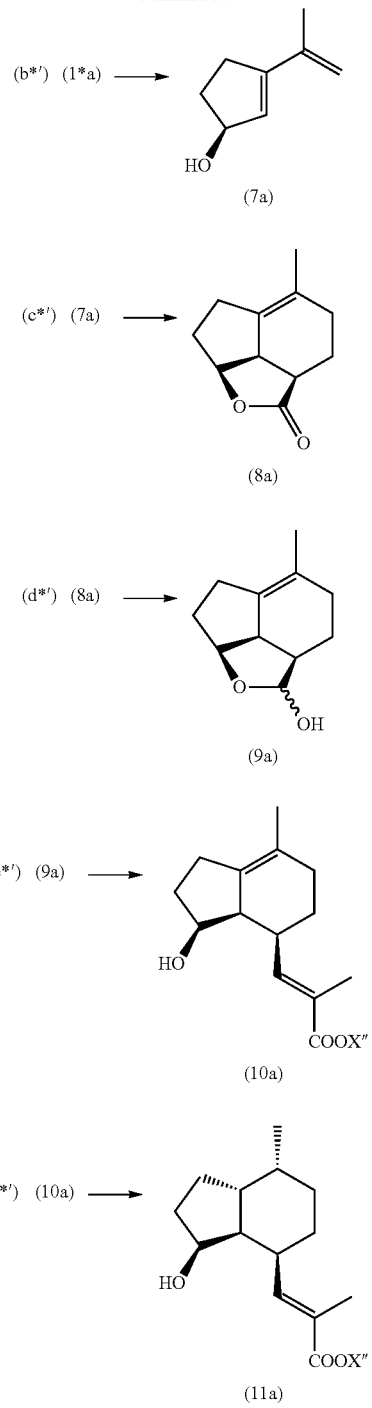
wherein X is selected from protecting groups including TsO, MsO; wherein X' is selected from protecting groups including TBSO, PMBO; wherein X'' is e.g. selected from C1-C10alkyl, C2-C10alkenyl, substituted or unsubstituted aryl; and wherein X''' is selected from protecting groups including TfO and AcO.
Scheme 1: Synthesis of valerenic acid comprising steps a*') to o*').
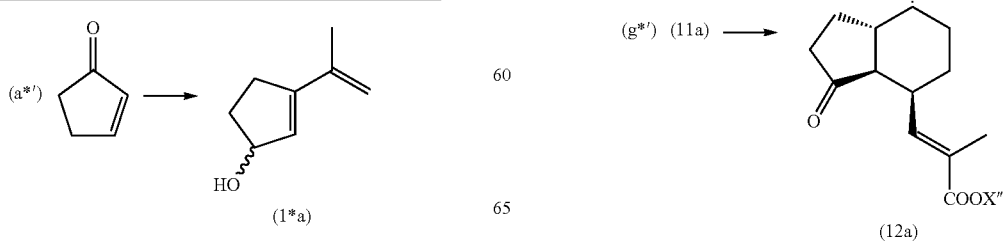

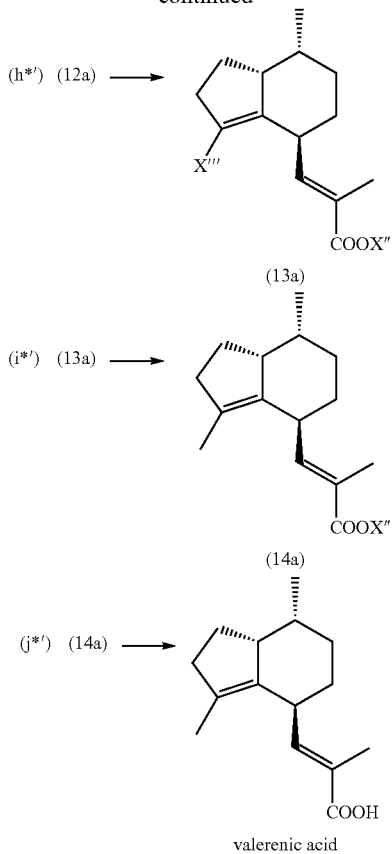

(h*') (12a) →

(i*') (13a) →

(j*') (14a) → valerenic acid wherein X" is e.g. selected from C1-C10alkyl, C2-C10alkenyl, substituted or unsubstituted aryl; and wherein X''' is selected from protecting groups including TfO and AcO.

Scheme 2: Synthesis of Valerenic Acid Comprising Steps a*) to j*).

In the following, the steps of scheme 1 will be outlined in detail.

(S)-Hex-5-yne-1,2-diol (1)

Compound (1) according to the present invention can be obtained by nucleophilic addition of a propargyl-fragment to (R)-Glycidol. A suitable agent for carrying out the nucleophilic reaction e.g. as a Grignard reaction is propargylmagnesium bromide. The corresponding reaction may be carried out as follows:

A mixture (prepared e.g. in freshly distilled ether) of magnesium turnings, mercury-(II)-chloride and iodide (preferably in trace amounts only) is treated with propargyl bromide (dissolved in an appropriate solvent such as, e.g., in freshly distilled ether). After the reaction has started, the mixture is cooled, preferably to about 0° C., and the rest of the propargyl bromide solution is added. After incubation at preferably about 0° C., the reaction mixture is warmed, preferably to about room temperature, and optionally further stirred. The reaction of magnesium turning (A), mercury-(II)-chloride (B) and propargyl bromide (C) is preferably carried out with equivalents, on a molar basis, of A:B:C in the ratio of about 200:1:100.

(R)-Glycidol is dissolved in an appropriate solvent (preferably in freshly distilled ether) and cooled, preferably to about −78° C. Under stirring, this solution is treated with propargylmagnesium bromide (which is preferably freshly prepared). The mixture is then warmed (preferably slowly and preferably to about room temperature) and quenched, e.g. with saturated aqueous $NH_4Cl$. Optionally, potassium sodium tartrate is then added, and the solution is extracted several times, using e.g. ether and ethyl acetate. The combined extracts are dried (e.g. using $Na_2SO_4$) and concentrated, preferably in vacuo. Finally, a chromatography purification (using e.g. a polar solvent gradient) is employed to yield compound (I). The reaction of (R)-Glycidol (A) and propargylmagnesium bromide (B) is preferably carried out with equivalents, on a molar basis, of A:B in the ratio of about 1:5.

(S)-2-Tosyl-hex-5-yne-1,2-diol (2a)

In order to obtain compound (2a), the terminal hydroxyl-group of compound (I) may be tosylated. In the corresponding reaction e.g. dibutyltinoxide may be used. The use of dibutyltinoxide ($Bu_2SnO$) is well known for the regioselective derivatization of vicinal diols. The corresponding reaction steps may be carried out as follows:

Diol (1) is dissolved in an appropriate solvent such as, e.g., dichloromethane and cooled, preferably to about 0° C. Dibutyltin oxide, triethylamine and toluenesulfonyl chloride are then added. After an incubation period of up to several hours, the icebath is removed and the reaction mixture is stirred, preferably for several hours. The mixture is then filtrated and the filtrate is concentrated, preferably in vacuo. Finally, a chromatography purification (using e.g. a polar solvent) is employed to yield compound (2). The reaction of Diol (1) (A), Dibutyltin oxide (B), triethylamine (C) and toluenesulfonyl chloride (D) is preferably carried out with equivalents, on a molar basis, of A:B:C:D in the ratio of about 75:1:75:75.

(S)-3-(tent-Butyldimethylsilyloxy)-hept-1-en-6-yne (4a)

In order to obtain compound (4a), tosylate (2a) may be treated with a base in order to form an epoxide, which may then react with sulfur glide. The resulting alcohol (3a) may then be protected. The corresponding reaction steps may be carried out as follows:

A suspension of trimethylsulfonium iodide, e.g. in tetrahydrofuran, is treated with n-BuLi, preferably at about −15° C. After stirring for several minutes up to several hours, tosylate (2a), dissolved in an appropriate solvent such as, e.g., tetrahydrofuran, is added. The resulting reaction mixture is stirred, preferably at the same temperature and for several hours, warmed, preferably to about room temperature, and quenched, e.g. by the addition of water. The solution is extracted, e.g. with ether for several times, and the combined organic phases are washed, e.g. with brine, dried (using e.g. $Na_2SO_4$) and concentrated, preferably in reduced vacuo. The reaction of trimethylsulfonium iodide (A), n-BuLi (B) and tosylate (2a) (C) is preferably carried out with equivalents, on a molar basis, of A:B:C in the ratio of about 53:10:50.

The crude (S)-hept-1-en-6-yne-3-ol (3a) is dissolved in a polar aprotic solvent, preferably in dichloromethane and cooled, preferably to about 0° C. Triethylamin and tert-butyldimethylsilyl triflate are added and the solution is warmed, preferably to about room temperature. After stirring for up to several hours, water is added and the solution is extracted, e.g. with dichloromethane for several times. The combined organic phases are washed, e.g. with brine, dried (using e.g. $Na_2SO_4$) and concentrated, preferably in vacuo. Finally, a chromatography purification (using e.g. a polar solvent) is employed to yield compound (4a). The reaction of (3a) (A), triethylamin (B) and tert-butyldimethylsilyl triflate (C) is preferably carried out with equivalents, on a molar basis, of A:B:C in the ratio of about 10:25:30.

(S)-3-(tent-Butyldimethylsilyloxy)-oct-1-en-6-yne (5a)

In order to obtain compound (5a), the terminal alkyne can be methylated. The corresponding reaction steps may be carried out as follows:

Compound (4a) is dissolved in an appropriate solvent, e.g. in tetrahydrofuran, and cooled, preferably to about −78° C., before treated with n-BuLi. The resulting solution is stirred for several minutes up to several hours, preferably at the same temperature, and then methyl iodide is added. The mixture is warmed (preferably slowly and to room temperature) and the reaction is quenched, e.g. with water. The solution is extracted, preferably with ether for several times, the combined extracts are washed, e.g. with brine, dried (using e.g. $Na_2SO_4$) and concentrated, preferably in vacuo. A chromatography purification (using e.g. a polar solvent) is employed to yield compound (5a). The reaction of Compound (4a) (A), n-BuLi (B) and methyl iodide (C) is preferably carried out with equivalents, on a molar basis, of A:B:C in the ratio of about 1:2:5.

(S)-1-(tert-Butyldimethylsilyloxy)-3-(prop-1'-en-2'-yl)cyclopent-2-en (6a)

In order to obtain compound (6a), compound (5a) can be rearranged in an ene yne metathesis. The corresponding reaction steps may be carried out as follows:

A solution of compound (6a) in an appropriate solvent, such as preferably degassed dichloromethane, is cooled, preferably to about 0° C. The flask is preferably flushed with ethylene gas over a period of several minutes before ethylene gas is bubbled through the solution itself for one to several additional minutes. Grubbs I catalyst is added and, optionally, once again ethylene gas is bubbled through the resulting mixture for one to several minutes. The icebath is removed and the mixture is stirred, preferably for several hours. The flask is preferably flushed with argon and the solvent is evaporated. Chromatography (using e.g. a polar solvent) of the residue results in compound (6a). The reaction of Compound (5a) (A) and Grubbs I catalyst (B) is preferably carried out with equivalents on a molar basis, of A:B in the ratio of about 100:15.

(S)-3-(Prop-1-en-2-yl)cyclopent-2-enol (7a)

In order to obtain compound (7a), the protecting group may be cleaved. The corresponding reaction steps may be carried out as follows:

A solution of compound (6a) in an appropriate solvent such as e.g. tetrahydrofuran is cooled, preferably to about 0° C., and treated with tert-Butylammonium floride. The reaction mixture is stirred (preferably for several hours and preferably at room temperature) and then quenched, e.g. with saturated aqueous $NH_4Cl$. The resulting solution is extracted, preferably with dichloromethane for several times and with AcOEt for several times, dried (using e.g. $Na_2SO_4$) and concentrated, preferably in vacuo. Chromatography purification (using e.g. a polar solvent gradient) is employed to yield compound (7a). The reaction of Compound (6a) (A) and tert-Butylammonium floride (B) is preferably carried out with equivalents, on a molar basis, of A:B in the ratio of about 10:15.

(2aR,7aS,7bR)-5-Methyl-3,4,6,7,7a,7b-hexahydro-2aH-indeno[1,7-bc]furan-2-one (8a)

In order to obtain compound (8a), a metal coordinated Diels Alder reaction can be performed. The corresponding reaction steps may be carried out as follows:

Anhydrous $MgBr_2.Et_2O$ is suspended in an appropriate solvent, such as e.g. dichloromethane, treated with diisopropyl-ethylamin and stirred until the suspension turns magenta. Then compound (7a) dissolved in an appropriate solvent, such as, e.g., dichloromethane, is added (preferably slowly and within several minutes). After stirring, methylacrylate is added. The resulting mixture is stirred, preferably for several hours, before it is quenched, e.g. with saturated aqueous $NH_4Cl$. Optionally, potassium sodium tartrate is added, and the solution is extracted, e.g. with dichloromethane for several times. The combined extracts are dried (using e.g. $Na_2SO_4$) and concentrated, preferably in vacuo. Chromatography (using e.g. a polar solvent) of the residue results in compound (8a). The reaction of $MgBr_2.Et_2O$ (A), diisopropyl-ethylamin (B), compound (7a) (C) and methylacrylate (D) is preferably carried out with equivalents, on a molar basis, of A:B:C:D in the ratio of about 2:4:1:2.

(E)-3-((3S,3aR,4S)-3-Hydroxy-7-methyl-2,3,3a,4,5,6-hexahydro-1H-inden-4-yl)-2-methyl-acrylic acid ethyl ester (10a)

In order to obtain compound (10a), the lacton can be reduced to the corresponding lactol followed by a Wittig olefination. The corresponding reaction steps may be carried out as follows:

A solution of compound (8a) in an appropriate solvent, such as, e.g., dichloromethane is cooled, preferably to about −78° C. and diisobutyl-ammoniumhydride is added. After stirring the mixture (preferably for several hours), the reaction is quenched, e.g. by the addition of AcOEt, and stirred. Potassium sodium tartrate, preferably as saturated aqueous solution, is then added and the mixture is warmed, preferably to about room temperature. The aqueous layer is separated and extracted, e.g. with dichloromethane for several times. The combined organic phases are dried (using e.g. $Na_2SO_4$) and concentrated, preferably in vacuo. Filtration (e.g. through a short pad of silica gel) results in a mixture of the two isomers. The reaction of compound (8a) (A) and diisobutyl-ammoniumhydride (B) is preferably carried out with equivalents, on a molar basis, of A:B in the ratio of about 10:15.

The mixture of isomers is dissolved in an appropriate solvent such as, e.g., benzene. (1-Ethoxycarbonylethyliden)-triphenylphosphoran is added and heated, preferably for several hours and under reflux. A quencher, such as $NH_4Cl$, preferably as saturated aqueous solution, is added and the solution is extracted, e.g. with dichloromethane for several times. The combined extracts are dried (using e.g. $Na_2SO_4$) and concentrated, preferably in vacuo. Chromatography purification (using e.g. a polar solvent gradient) is employed to yield compound (10a). The reaction of the isomer-mixture (A) and (1-Ethoxycarbonylethyliden)-triphenylphosphoran (B) is preferably carried out with equivalents, on a molar basis, of A:B in the ratio of about 1:3.

(E)-3-((3S,3aS,4S,7R,7aR)-3-Hydroxy-7-methyl-octahydro-inden-4-yl)-2-methyl-acrylic acid ethyl ester (11a)

In order to obtain compound (11a), an alcohol directed catalytic hydrogenation can be performed. The corresponding reaction steps may be carried out as follows:

A solution of compound (10a) and an appropriate solvent such as dichloromethane (preferably degassed) is cooled, preferably to about 0° C. Preferably, the flask is flushed with hydrogen over a period of several minutes before hydrogen is bubbled through the solution itself for one to several additional minutes. After adding Crabtree catalyst, the flask is preferably once again flashed with hydrogen for several minutes before hydrogen is bubbled through the solution for several minutes until it becomes colorless. The icebath is removed and the mixture is stirred, preferably for several hours. Preferably, argon is then bubbled through the reaction mixture and the solvent is evaporated. Chromatography (using e.g. a polar solvent gradient) of the residue results in compound (11a). The reaction of compound (10a) (A) and Crabtree catalyst (B) is preferably carried out with equivalents, on a molar basis, of A:B in the ratio of about 10:1.

(E)-2-Methyl-3-((3aS,4S,7R,7aR)-7-methyl-3-oxo-octahydro-inden-4-yl)-acrylic acid ethyl ester (12a)

In order to obtain compound (12a), the alcohol can be oxidized to the corresponding ketone. The corresponding reaction steps may be carried out as follows:

Compound (11a) is dissolved in an appropriate solvent, preferably in dimethylsulfoxide, and treated with a solution of IBX, preferably in dimethylsulfoxide. After stirring for up to several hours, water is added and the white precipitate is removed by filtration. The precipitate is washed, preferably with dimethylsulfoxide/water and a small amount of AcOEt. The filtrate is extracted, preferably with dichloromethane for several times, the combined organic phases are dried (using e.g. $Na_2SO_4$) and concentrated, preferably in vacuo. Chromatography purification (using e.g. a polar solvent gradient) is employed to yield compound (12a). The reaction of compound (11a) (A) and IBX (B) is preferably carried out with equivalents, on a molar basis, of A:B in the ratio of about 1:2.

Valerenic Acid Ethyl Ester (14a)

In order to obtain compound (14a), the thermodynamically more stable enol triflate is preferably formed, which may then be alkylated in a Negishi coupling. The corresponding reaction steps may be carried out as follows:

A solution of compound (12a) and an appropriate solvent, such as, e.g., dichloromethane, is cooled, preferably to about 0° C., and treated with triflic anhydride (preferably freshly distilled) and pyridine, preferably under vigorous stirring. The icebath is removed and the mixture is stirred for up to several hours. The reaction mixture is cooled, preferably to about 0° C., and washed, e.g. by consecutive washes with e.g. saturated aqueous $CuSO_4$ and saturated aqueous $NaHCO_3$. Both aqueous layers are extracted, e.g. with dichloromethane for several times. The combined organic phases are washed, e.g. with brine, dried (using e.g. $Na_2SO_4$) and concentrated, preferably in vacuo. Filtration (e.g. through a short pad of silica gel) results in a mixture of the two isomers. The reaction of compound (12a) (A), triflic anhydride (B) and pyridine (C) is preferably carried out with equivalents, on a molar basis, of A:B:C in the ratio of about 1:10:10.

The mixture of isomers is dissolved in an appropriate solvent, such as, e.g., tetrahydrofuran, and cooled, preferably to about 0° C., before palladiumtetrakis is added. After stirring (preferably for several minutes), the resulting brown solution is treated with dimethylzinc and incubated. The mixture is allowed to warm, preferably to about room temperature, and stirred (preferably for several hours), followed by quenching, e.g. by the addition of water and saturated aqueous $NH_4Cl$. The solution is extracted, e.g. with ether for several times. The combined extracts are washed, e.g. with brine, dried (using e.g. $Na_2SO_4$) and concentrated, preferably in vacuo. Chromatography purification (using e.g. a polar solvent gradient) is employed using $AgNO_3$ treated silica gel (preferably treated with 10% $AgNO_3$) to yield compound (14a). The reaction of the isomer-mixture (A), palladiumtetrakis (B) and dimethylzinc (C) is preferably carried out with equivalents, on a molar basis, of A:B:C in the ratio of about 10:1:40.

Valerenic Acid (VA)

In order to obtain Valerenic acid, the ester (14a) may be saponified. The corresponding reaction steps may be carried out as follows:

A solution of compound (14a) in appropriate solvents such as, e.g., methanol and tetrahydrofuran is treated with 1.0 molar aqueous LiOH. After stirring for up to several hours, the resulting mixture is cooled, preferably to about 0° C., acidified, e.g. by the use of 10% citric acid, and extracted, preferably with EtOAc for several times. The combined organic phases are washed, e.g. with brine, dried (using e.g. $Na_2SO_4$) and concentrated, preferably in vacuo. Purification by chromatography (using e.g. a polar solvent gradient) is employed to yield valerenic acid. The reaction of compound (14a) (A) and LiOH (B) is preferably carried out with equivalents, on a molar basis, of A:B in the ratio of about 1:7.

In the following, the steps (a*') and (b*') of scheme 2 will be outlined in more detail. The steps (c*') to (j*') are carried out analogous to the steps (h') to (o') of scheme 1.

Compound (1a*)

Compound (1a*) according to the present invention can be obtained by nucleophilic addition of a propen-2-yl-fragment to cyclopentenone followed by a rearrangement reaction. A suitable agent for carrying out the nucleophilic reaction e.g. as a organometallic reaction is propen-2-yl lithium and a suitable agent for carrying out the rearrangement reaction is e.g. trifluoro acetic acid (TfOH). The corresponding reaction may be carried out as follows:

A solution of 2-bromopropene in an appropriate solvent as e.g. diethylether is cooled, preferably to about –78° C. The 2-brompropene is metallated using, e.g. tert-butyllithium, wherein the resulting yellow solution is stirred, preferably for several hours at the same temperature. A solution of cyclopentenone in an appropriate solvent as e.g. diethylether is cooled, preferably to about –78° C. Then the propen-2-yl lithium is added and the resulting solution is stirred, preferably up to several hours, before the solution is warmed, preferably to about 0° C. One or more suitable solvents as e.g. water and tetrahydrofuran are added and the biphasic mixture is stirred, preferably up to several hours at room temperature. After the mixture is cooled, preferably to about 0° C., an acid such as e.g. trifluoroacetic acid is added. The colourless biphasic solution is stirred, preferably up to several hours, and is then quenched with e.g. $NaHCO_3$, preferably using an aqueous solution, more preferred using a saturated aqueous solution. The aqueous phase is extracted with an appropriate solvent as e.g. dichloromethane, preferably for several times, and the combined organic extracts are dried (using e.g. $Na_2SO_4$) and concentrated e.g. using vacuo. Chromatography (using e.g. a polar solvent gradient) of the residue results in compound (Ia*).

Compound (6a)

In order to obtain compound (6a), one of the enantiomers of the racemic dienol (1a*) may be selectively reacted, e.g. acetylated employing a catalyst or enzyme and a acetyl source such as lipase PS and vinyl acetate, before the enantiomers are separated, e.g. using chromatography. The corresponding reaction steps may be carried out as follows:

The racemic dienol (1*) is dissolved in an appropriate solvent, preferably MTBE. A suitable catalyst/enzyme such as lipase PS and a suitable acetyl source such as vinyl acetate are added. The resulting mixture is reacted for several hours, preferably at elevated temperature, even more preferred at about 40° C. Solids are removed, e.g. by filtration, and the filtrate is concentrated e.g. using vacuo. Finally, chromatography (using e.g. a polar solvent gradient) is employed to yield compound (6a).

2.2. Methods for Making Valerenic Acid Derivatives

Based on the reaction scheme for preparing valerenic acid set out above and by modifying certain steps of the reaction scheme as outlined below, the skilled person is able to prepare valerenic acid derivatives as claimed and described herein. The inventive method for preparing valerenic acid allows for the selective introduction of substituents in order to provide the compounds defined in formulae (I), (IA1), (IA2), (IB), (IC) and (ID). By using suitable reactants bearing the corresponding substituents in the inventive reaction scheme set out above, it is possible to prepare specific valerenic acid derivatives. The derivatives can be obtained without imparting the stereoselectivity of the inventive reaction scheme. The skilled person will understand that the synthesis route or method described above provides general guidance and an easy way for preparing a multitude of different valerenic acid derivatives, wherein the different substituents or modifications are introduced at different stages of the preparation process.

In order to synthesize the inventive valerenic acid derivatives, one may, in a first step, prepare the intermediate compound (9) as defined above. By following the corresponding reaction scheme described herein, one or more of substituents $R_1$, $R_2$, $R_3$, $R_7$, $R_8$ and $R_9$, or any combination of said residues may be introduced. Dependent on the valerenic acid derivative according to compound (I) to be synthesized (i.e. particularly dependent on ring D chosen), one may use the intermediate compound (9) and follow the alternative synthesis routes defined herein for providing compounds (IA2), (IB), (IC) and (ID). This will be outlined in detail below.

Firstly, a general reaction scheme in order to arrive at compound (9) is given in the following paragraphs.

(S)-Hex-5-yne-1,2-diol (1)

Compound (1) according to the present invention can be obtained by nucleophilic addition of a propargyl-fragment to (R)-Glycidol. A suitable agent for carrying out the nucleophilic reaction e.g. as a Grignard reaction is e.g. propargylmagnesium bromide.

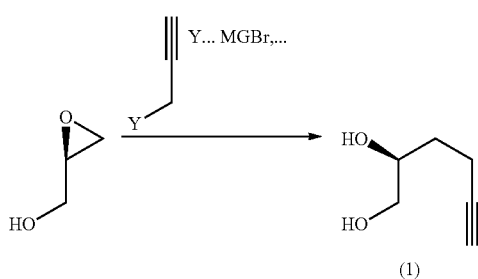

Compound (3)

Compound (3) may be obtained by oxidation of the primary alcohol and olefination of the resulting aldehyde. Using a common procedure this can e.g. be done by selective protection of the secondary alcohol, oxidation of the remaining unprotected primary alcohol (e.g.: Swern oxidation, IBX, and the like) and a final olefination (e.g. a Wittig olefination) of the resulting aldehyde. A suitable protecting group for the secondary alcohol may be e.g. the p-methoxybenzyl group (PMB, wherein X is PMBO) which can easily be introduced in a two step reaction.

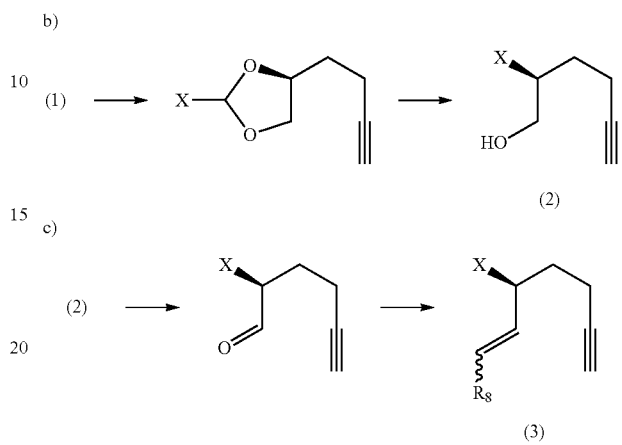

If $R_8$=H in compound (3), said compound may also be obtained in a three step reaction starting with diol (1). After converting the primary alcohol into a suitable leaving group (e.g. TsO or MsO) and subsequent reaction with a sulfurylide (e.g. with trimethylsulfurylide $Me_2S=CH_2$), the final protection of the allylic alcohol using e.g. TBSOTf or the like in the presence of a base such as $NEt_3$ may result in compound (3) wherein $R_8$=H. This is shown in the following reactions b") to d"):

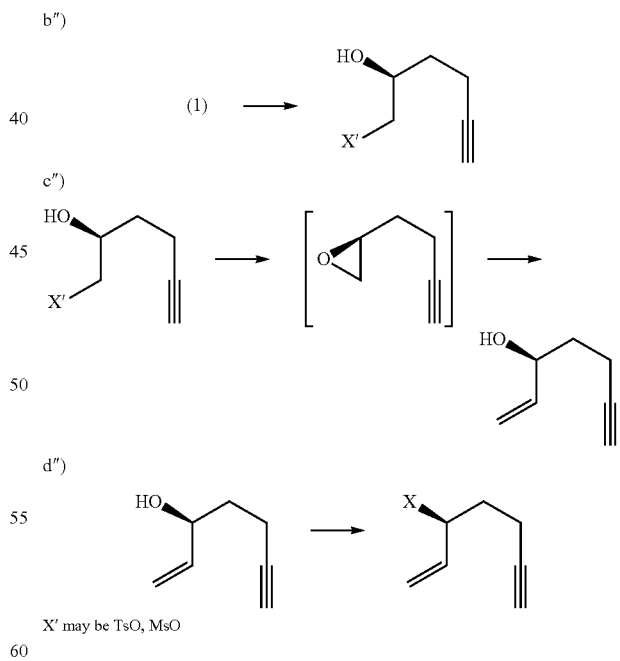

X' may be TsO, MsO

Compound (4)

By carrying out an electrophilic addition reaction starting from compound (3) and using e.g. alkylbromid reactants, the substituent $R_7$ may be modified or introduced into the inventive compounds according to the following scheme in order to obtain compound (4):

d)

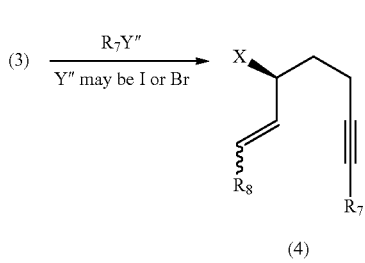

f)

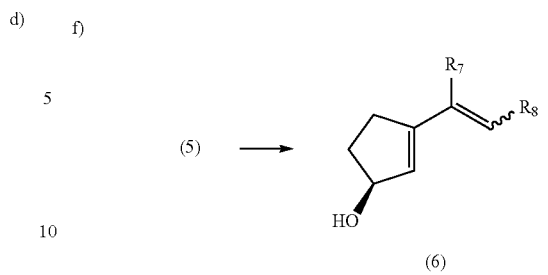

Compound (5)

In order to obtain compound (5), compound (4) may be rearranged in an ene-yne-metathesis reaction. This can be done by using e.g. Grubbs I catalyst in an ethylene atmosphere.

e)

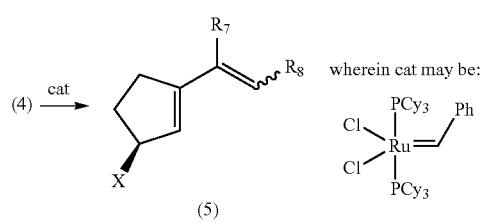

Compound (1*)

Compound (1*) can be obtained by a nucleophilic addition and a rearrangement reaction. Suitable agents for carrying out the addition reaction e.g. as a organometallic reaction are e.g. organolithium compounds. A suitable agent for carrying out the rearrangement reaction e.g. as an acid catalyzed rearrangement reaction is an acid such as trifluoro acetic acid (TfOH).

(a*)

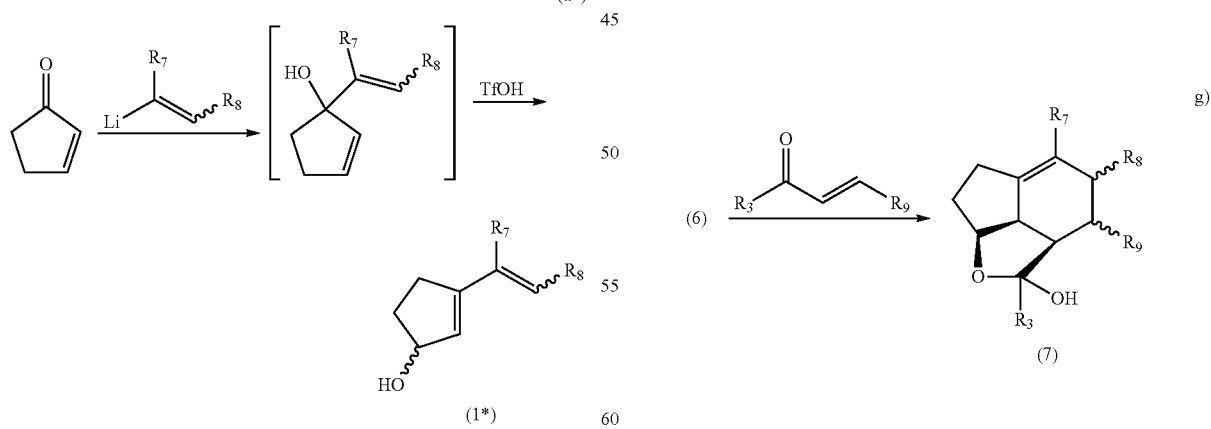

Compound (6)

In order to obtain compound (6), the protecting group X (e.g. TBSO or PMBO) may be cleaved. Depending on the protecting group various reagents such as TBAF (tetra-n-butylammonium fluoride) may be used.

Furthermore, compound (6) may be obtained starting from the isomer mixture (1*). This mixture may be separated e.g. by a catalytic selective reaction of one stereoisomer of (1*) followed by the separation of the reaction product from the non-reacted stereoisomer using e.g. chromatography. A suitable agent or system for a selective reaction of one stereoisomer is lipase PS used together with vinyl acetate which can be used for a selective acylation.

(b*)

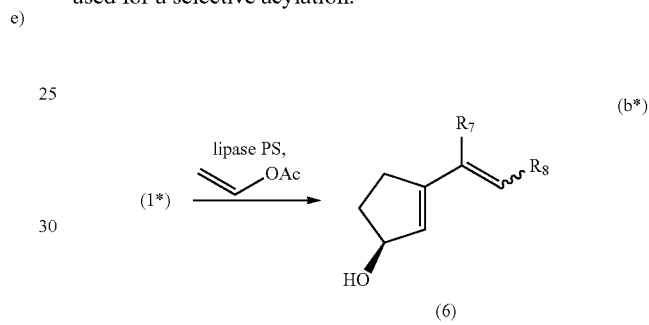

Compound (7)

In order to obtain compound (7), a Diels Alder reaction can be carried out. This can be done by deprotonation of the alcohol with a base, such as diisopropylethylamine, and a metal salt, such as e.g. $MgBr_2 \cdot Et_2O$, and subsequent treatment with a suitable dienophile like an unsaturated ketone, such as e.g. $MeCO=CH_2$, in order to implement substituents $R_3$ and $R_9$.

g)

Obviously, starting from compound (6) one can also use unsaturated esters such as methyl acrylate in a first reaction step resulting in lactone (7') followed by a reduction of the lactone (7') to the corresponding lactol (7") using e.g. diisobutylaluminiumhydride (DIBALH) as reducing agent. This may result in a compound (7") wherein $R_3$ is H, as shown in $g_{alt}$:

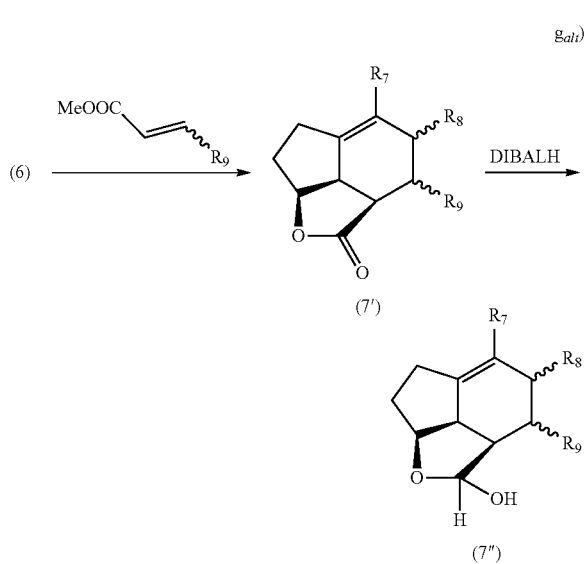

Compound (8)

In order to obtain compound (8), an olefination of lactol (7) may be carried out, e.g. with various phosphoros ylides (such as $Ph_3P=CHR_1R_2$) as shown below:

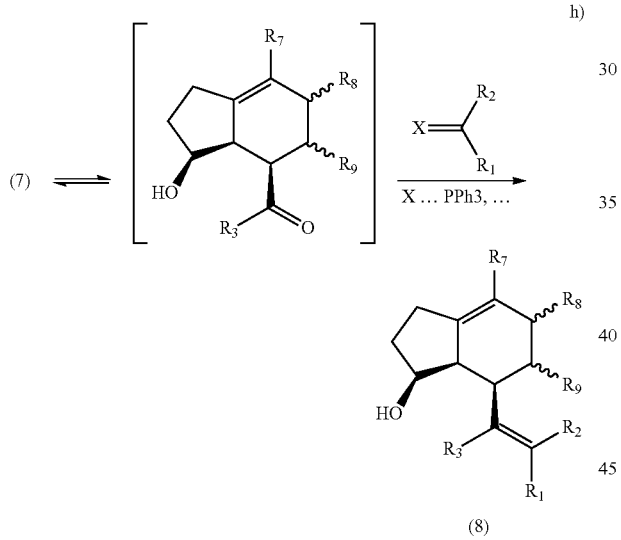

Compound (9)

Compound (9) can be obtained by hydroxyl directed hydrogenation of compound (8). A suitable catalyst for carrying out the hydrogenation is e.g. $[Ir(cod)py(PCy_3)]PF_6$ (mentioned as "cat" in the scheme below).

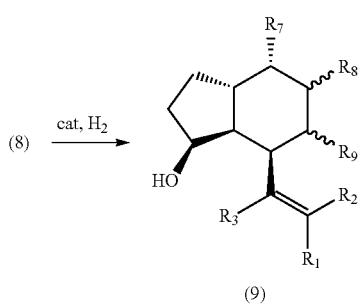

In all reaction steps outlined above, X may be selected from TBSO and PMBO and X' from TsO and MsO.

Starting from key precursor compound (9), different rings D as defined in general formula (I) may be introduced according to the following reaction schemes. It should be noted, however, that most of the reaction steps in the following four schemes differ only slightly.

The first step j) may be identical in all four reaction schemes and result in compound (10). Said step may comprise oxidation of the alcohol to the corresponding ketone. A suitable oxidizing agent for carrying out this reaction is e.g. IBX (2-iodoxybenzoic acid) or PDC (pyridinium dichromate).

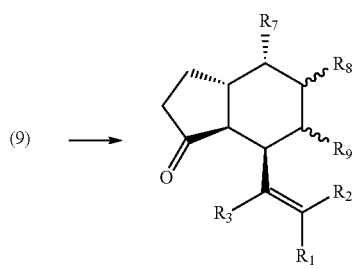

In the following, the reaction steps in order to arrive at compounds of formula (IA2) are described:

Introduction of $R_4$ Via a Two Step Reaction [k1) and l1)]

In order to introduce $R_4$ in a compound of formula (IA2), the keto-moiety of compound (10) may be converted into the thermodynamically more stable enolate. This may be done by using a pyridine as base and triflic anhydride as electrophile to form the corresponding enoltriflate, followed by cross coupling of the resulting enoltriflate with a suitable metalorganyl (such as dialkyl-zinc, aryl-zinc, aryl-zinchalogenides, aryl-stannane or alkyl-zinc, alkyl-zinchalogenides or alkyl-stannane). The reaction may be carried out according to the following scheme:

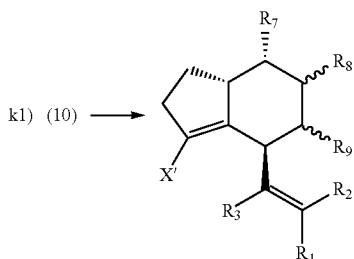

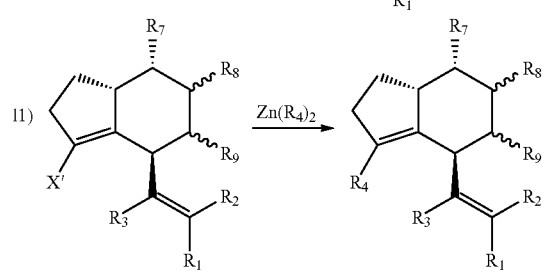

Introduction of a Single Bond Between $C_{10}$ and $C_{11}$ Via Reaction m1)

In order to introduce a single bond between $C_{10}$ and $C_{11}$ in compound (IA2), the corresponding double bond may be hydrogenated. Suitable hydrogenation methods may be chosen dependent on the nature of substituents $R_1$, $R_2$, $R_3$ and/or $R_4$.

m1)

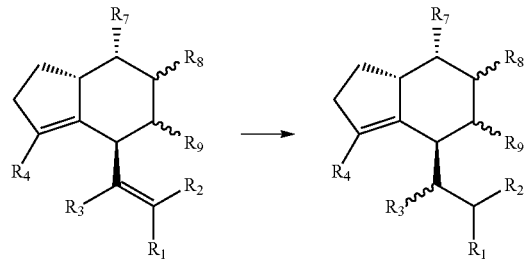

It is clear to the skilled person that the hydrogenation reaction needs to be selective for removing the double bond between $C_{10}$ and $C_{11}$. Thus, as mentioned above, the reaction may inter alia be dependent on the substituents $R_1$, $R_2$, $R_3$ and/or $R_4$ as well as on the degree of substitution on $C_{10}$ and $C_{11}$. In some cases (e.g. if substituents $R_1$, $R_2$ and/or $R_3$ are electron-withdrawing groups with $R_1$ being e.g. COOX") a reduction of the COOX"-group to the corresponding alcohol $CH_2OH$, followed by a hydroxyl-directed hydrogenation may be carried out. Said hydroxyl-directed hydrogenation is thus specific for the double bond between $C_{10}$ and $C_{11}$. In the next step, the alcohol may be oxidized to the carboxylic acid COOH, which may then be converted into COOX" by an esterification reaction. However, further reaction schemes for introduction of a single bond between $C_{10}$ and $C_{11}$ are possible and obvious to the skilled person and one exemplary reaction scheme is shown below in the section "modification of substituent $R_3$".

In all reaction steps shown above for compound (IA2), X' may be selected from TfO, AcO and X" may e.g. be a C1-C10alkyl.

In the following, the reaction steps in order to arrive at compounds of formula (IC) are described:

Introduction of $R_4$ Via a Two Step Reaction [k3) and l3)]

In order to introduce $R_4$ in a compound of formula (IC), the keto-moiety of compound (10) has to be converted into the kinetically favoured enolate. This may be done by using KHMDS (potassium hexamethyldisilizane) as base at low temperature and triflic anhydride as electrophile to form the corresponding enoltriflate, followed by cross coupling of the resulting enoltriflate with a suitable metalorganyl (such as dialkyl-zinc, aryl-zinc, aryl-zinchalogenides, aryl-stannane or alkyl-zinc, alkyl-zinchalogenides, or alkyl-stannane). The reaction may be carried out according to the following scheme:

k3) (10) →

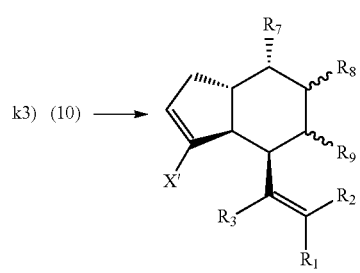

l3)

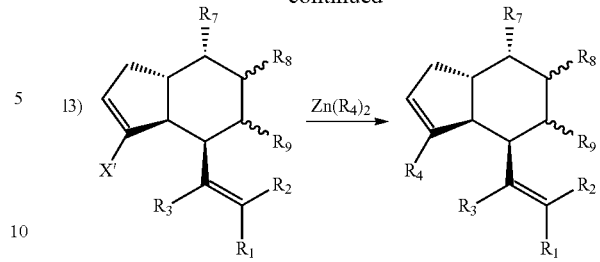

Introduction of a Single Bond Between $C_{10}$ and $C_{11}$ Via Reaction m3)

In order to introduce a single bond between $C_{10}$ and $C_{11}$ in compound (IC), the corresponding double bond may be hydrogenated. Suitable hydrogenation methods may be chosen dependent on the nature of substituents $R_1$, $R_2$ and/or $R_3$ and the explanations and comments for this hydrogenation reaction given above for compound (IA2) also apply for compound (IC).

m3)

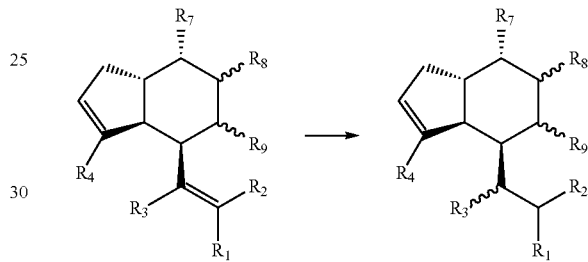

In all reaction steps shown above for compound (IC), X' may be selected from TfO, AcO.

In the following, the reaction steps in order to arrive at compounds of formula (IB) are described:

Introduction of $R_4$

In order to introduce $R_4$ in compound (IB), the first two reactions k3) and l3) as outlined above may be carried out. They are again shown in the following, but referred to as reactions k2) and l2). Thus, k2) corresponds to k3), whereas l2) corresponds to l3):

k2)

(10) →

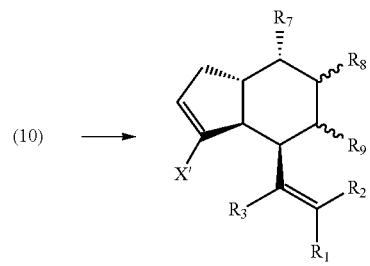

l2)

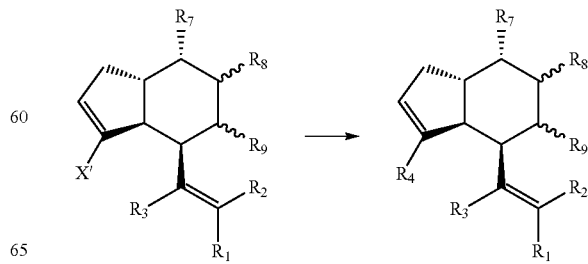

In the next reaction step, a catalytic hydrogenation (using e.g. Pd/C and the like) may be carried out according to the following scheme:

m2)

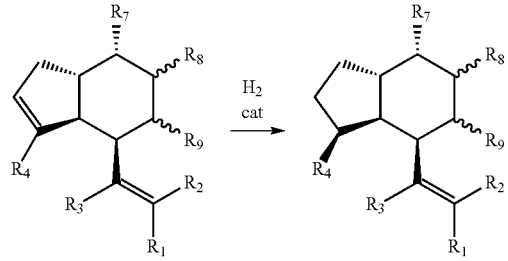

In order to introduce a single bond between $C_{10}$ and $C_{11}$ in compound (IB), a catalytic hydrogenation (using e.g. Pd/C and the like) may be carried out according to the following scheme:

n2)

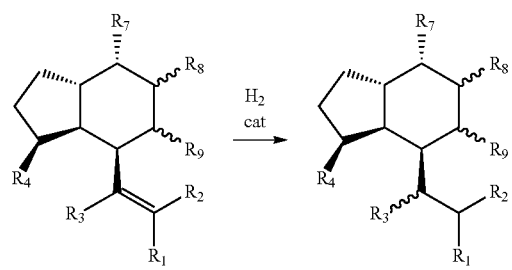

In all reaction steps shown above for compound (IB), X' may be selected from TfO, AcO.

In the following, the reaction steps in order to arrive at compounds of formula (ID) are given:

Introduction of $R_4$ Via Reaction 14)

In order to introduce $R_5$ in compound (ID), olefination (e.g. a Wittig olefination) of the ketone moiety of compound (10) may be carried out according to the following scheme:

k4)

(10) →

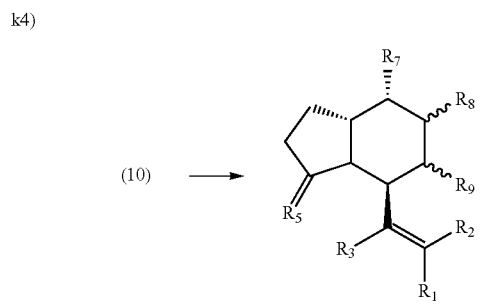

Introduction of a Single Bond Between $C_{10}$ and $C_{11}$ Via Reaction 14)

In order to introduce a single bond between $C_{10}$ and $C_{11}$ in compound (ID), a catalytic hydrogenation (using e.g. Pd/C and the like) may be carried out according to the following scheme:

l4)

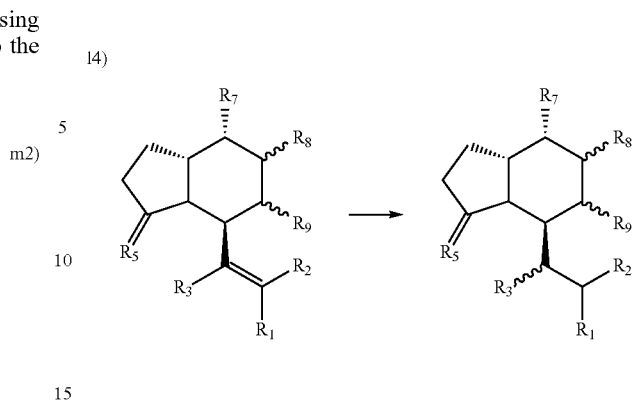

In the following, some additional reaction schemes are shown in order to provide additional ways and information relating to the synthesis of valerenic acid derivatives. More precisely, the following section refers to the single introduction or modification of substituents $R_1$, $R_2$, $R_3$, $R_4$, $R_6$, $R_7$ and $R_9$ and refers to compounds of the general reaction scheme 1. Obviously, also valerenic acid derivatives with several substituents can be obtained and further modified. The skilled person knows how to combine the corresponding modified reactants and/or modified reaction steps in order to arrive at a compound displaying substituents within the scope of a compound of claim 1 since a general scheme is given above.

Modification of Substituent $R_1$

At the COOH-group of the valerenic acid or any derivative of valerenic acid, a substituent $R_1$ can be introduced by known methods for modifying carboxyl-groups. The substituent $R_1$ may be introduced or modified according to the following reaction scheme:

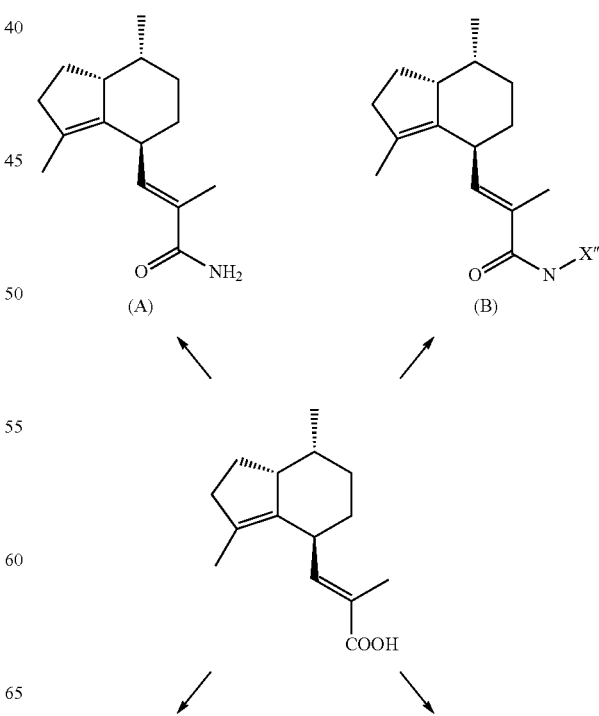

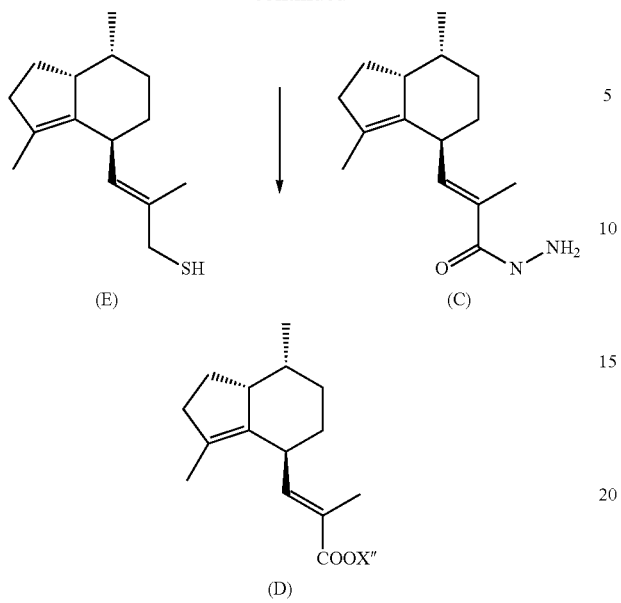

wherein X" may e.g. be a C1-C10alkyl.

The compounds (A) bearing an amide group as substituent $R_1$ can be obtained by amidation of the carboxylic acid group of the valerenic acid or any derivative of valerenic acid. The compounds (B) bearing a secondary amide group as substituent $R_1$ can be obtained by alkylation, acylation reactions and the like of the amides (A). The compounds (C) bearing an hydrazide group as substituent $R_1$ can be obtained by conversion of the carboxylic acid group of the valerenic acid or any derivative of valerenic acid into the acid chloride and subsequent treatment with hydrazine. The compounds (D) bearing an alkyl group as substituent $R_1$ can be obtained by esterification of the carboxylic acid group of the valerenic acid or any derivative of valerenic acid. The compounds (E) bearing an thiole group as substituent $R_1$ can be obtained by reduction of the carboxylic acid group of the valerenic acid or any derivative of valerenic acid to the corresponding alcohol and subsequent treatment with Lawesson's reagent.

Modification of Substituent $R_2$

In the above shown reaction scheme 1, compound (8a) is converted into compound (10a) in a 2-step procedure. If after the reduction step of compound (8a) [(using e.g. diisobutyla- luminiumhydride [DIBAL])] resulting in compound (9a) a reactant bearing a substituent $R_2$ is used for the reaction with the carbonyl-group, compound (10a) with a substituent $R_2$ instead of a methyl group can be obtained. The corresponding conversion is shown in the following scheme:

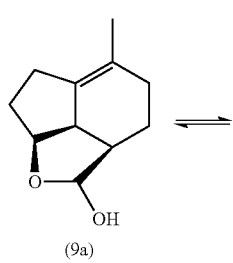

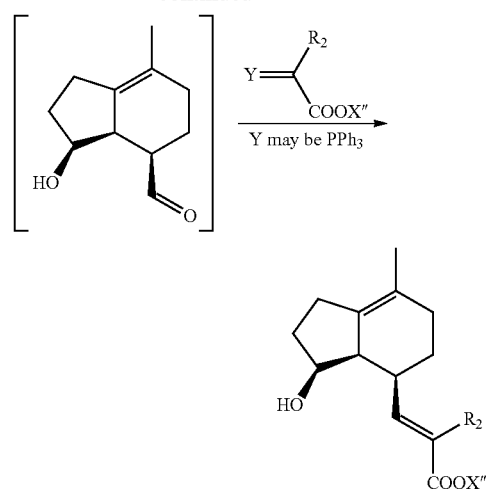

Modification of Substituent $R_3$

Starting from compound (7a) it is possible to introduce substituent $R_3$ by e.g. a cycloaddition (Diels Alder reaction) according to the following scheme:

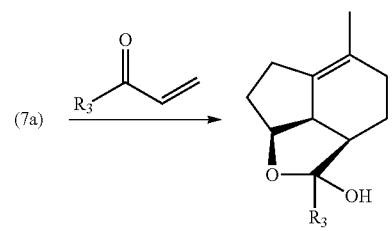

Furthermore, starting from compound (14a) it is possible to introduce $R_3$ according to a 1,4-addition (Michael reaction) resulting not only in the introduction of $R_3$ but also in a single bond between $C_{10}$ and $C_{11}$ as shown in the following reaction scheme:

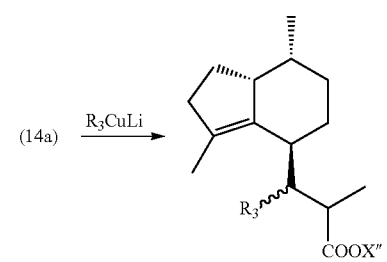

Modification of Substituent $R_4$

By carrying out a nucleophilic addition reaction starting from compound (13a) and using e.g. aryl-zinc or alkyl-zinc reactants, the substituent $R_4$ may be modified or introduced into the inventive compounds according to the following scheme:

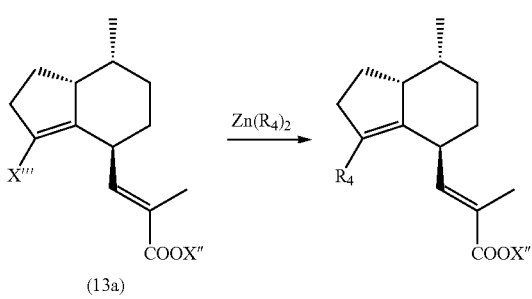

(13a)

Modification of Substituent $R_7$

By carrying out a nucleophilic substitution reaction starting from compound (4a) and using e.g. alkylbromid reactants, the substituent $R_7$ may be modified or introduced into the inventive compounds according to the following scheme:

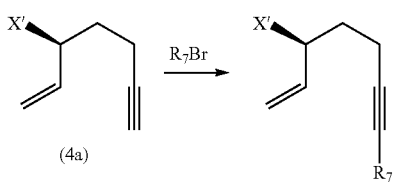

(4a)

Modification of Substituent $R_9$

The substituent $R_9$ can be modified or introduced in the inventive valerenic acid derivatives starting from compound (7a) according to the following scheme:

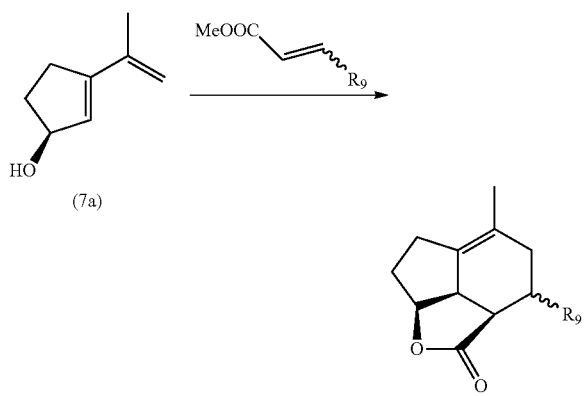

(7a)

Introduction of a Double Bond Between $C_2$ and $C_3$ of the 5-Membered Ring D

By slightly modifying the reaction scheme above starting from compound (12a), a double bond may be introduced between $C_2$ and $C_3$ of the 5-membered ring D according to the following scheme:

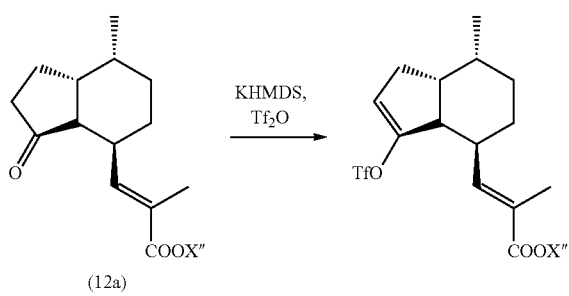

(12a)

Introduction of $R_6$

By starting from the natural compound hydroxy-valerenic acid, it is easily possible to carry out e.g. an alkylation or acylation of the alcohol. Moreover, the alcohol could easily be converted into a leaving group (e.g. by tosylation). In a subsequent nucleophilic substitution, various other derivatives may easily be prepared (with $R_6$ being e.g. CN, Br). Also, other substitutents as defined above for $R_6$ such as e.g. a substituted or unsubstituted $C_1$-C10alkyl, a substituted or unsubstituted aryl may easily be prepared according to standard synthesis methods known to the skilled person. Furthermore, it is obvious to the skilled person that a substitutent $R_1$ may be introduced at the COOH— (or the COOX"—) group and/or modified, e.g. according to the scheme already provided above ("modification of substituent $R_1$"). The reactions to introduce $R_6$ may be carried out according to the following general scheme:

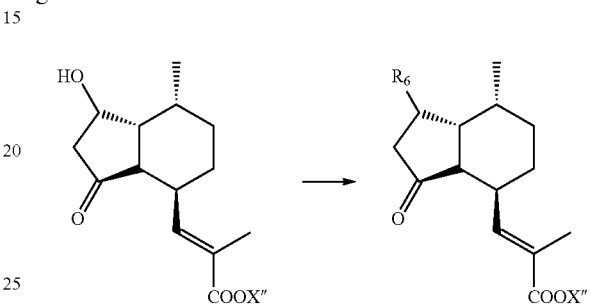

wherein X" may be a C1-C10alkyl.

3. Pharmaceutical Compositions

If at least one valerenic acid derivative and/or at least one pharmaceutically acceptable salt and/or solvate thereof is/are comprised within a medicament, such a medicament may be formulated for oral, bucal, nasal, rectal, topical or parenteral application. Parenteral application may include intravenous, intramuscular or subcutaneous administration. The at least one valerenic acid derivative and/or at least one pharmaceutically acceptable salt and/or solvate thereof may be applied in pharmaceutically effective amounts, for example in the amounts set out herein below.

Pharmaceutical dosage forms may be solid or liquid dosage forms or may have an intermediate, e.g. gel-like character depending inter alia on the route of administration.

In general, the inventive solid dosage forms will comprise various pharmaceutically acceptable excipients which will be selected depending on which functionality is to be achieved for the dosage form.

A "pharmaceutically acceptable excipient" in the meaning of the present invention can be any substance used for the preparation of pharmaceutical dosage forms, including but not limited to coating materials, film-forming materials, fillers, disintegrating agents, release-modifying materials, carrier materials, diluents, binding agents and other adjuvants.

Typical pharmaceutically acceptable excipients include substances like sucrose, manitol, sorbitol, starch and starch derivatives, lactose, and lubricating agents such as magnesium stearate, disintegrants and buffering agents.

In case that liquid dosage forms are considered for the present invention, these can include pharmaceutically acceptable emulsions, solutions, suspensions and syrups containing inert diluents commonly used in the art such as water. These dosage forms may contain e.g. microcrystalline cellulose for imparting bulk, alginic acid or sodium alginate as a suspending agent, methylcellulose as a viscosity enhancer and sweeteners/flavouring agents. When administered by nasal aerosol or inhalation, the compositions according to the present invention may be prepared as solutions in a saline, employing benzyl alcohol or other suitable preservatives, absorption promoters to enhance bioavailability fluorocarbons and/or other solubilising or dispersing agents.

Further conventional excipients, which can be used in the aforementioned dosage forms depending on the functionality that is to be achieved for the dosage form, include pharmaceutically acceptable organic or inorganic carrier substances which do not react with the active compound. Suitable pharmaceutically acceptable carriers include, for instance, water, salt solutions, alcohols, oils, preferably vegetable oils, polyethylene glycols, gelatin, lactose, amylose, magnesium stearate, surfactants, perfume oil, fatty acid monoglycerides and diglycerides, petroethral fatty acid esters, hydroxymethylcellulose, polyvinylpyrrolidone and the like. The pharmaceutical preparations can be sterilized and if desired, mixed with auxiliary agents, like lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants.

The person skilled in the art is aware that bioavailability of the at least one valerenic acid derivative and/or its pharmaceutically acceptable salt and/or solvate can be enhanced by micronisation of the formulations and the actives using conventional techniques such as grinding, milling and spray-drying in the presence of suitable excipients or agents such as phospholipids or surfactants.

Injectable preparations of at least one valerenic acid derivative and/or pharmaceutically acceptable salt and/or solvent thereof, for example sterile injectable aqueous or oleaginous suspensions, can be formulated according to the known art using suitable dispersing agents, wetting agents and/or suspending agents. A sterile injectable preparation can also be a sterile injectable solution or suspension in a non-toxic parenterally acceptable diluant or solvent. Among the acceptable vehicles and solvents that can be used are water and isotonic sodium chloride solution. Sterile oils are also conventionally used as solvent or suspending medium.

Suppositories for rectal administration of at least one valerenic acid derivative and/or pharmaceutically acceptable salt and/or solvent thereof can be prepared by e.g. mixing the compounds or compositions with a suitable non-irritating excipient such as cocoa butter and polyethylene glycols which are solid at room temperature but liquid at rectal temperature such that they will melt in the rectum and release the at least one valerenic acid derivative and/or pharmaceutically acceptable salt and/or solvent thereof from said suppositories.

Oral dosage forms may be a particularly preferred embodiment in view of patients' overall acceptance of this type of dosage forms. Oral dosage forms may be liquid or solid. Solid oral dosage forms can include e.g. tablets, troches, pills, capsules, powders, effervescent formulations, dragees and granules.

According to another aspect of the present invention, the solid dosage form comprises a film coating. For example, the inventive dosage form may be in the form of a so-called film tablet. According to some aspects, the inventive dosage may comprise two or more film coating layers. The corresponding dosage form may be a bilayer or multilayer tablet.

As outlined above, suitable dosage forms according the present invention may be in the form of a tablet, a dragee or a capsule. The capsule may be a two-piece hard gelatin capsule, a two-piece hydroxypropylmethylcellulose capsule, a two-piece capsule made of vegetable or plant-based cellulose or a two-piece capsule made of polysaccharide. The tablet may be a compressed tablet and/or a film coated tablet.

In one embodiment, the oral dosage forms may be formulated to ensure an immediate release of the at least one valerenic acid derivative and/or its pharmaceutically acceptable salt and/or solvate.

In another embodiment, the oral dosage forms may be formulated to ensure a controlled release of the at least one valerenic acid derivative and/or its pharmaceutically acceptable salt and/or solvate. Such dosage forms may therefore be designated as controlled release (CR) pharmaceutical dosage forms.

The term "controlled release dosage form" in the context of the present invention is used to highlight that a pharmaceutical dosage form is not an immediate release (IR) pharmaceutical dosage form. An oral immediate release pharmaceutical dosage form will typically release substantially all of the at least one valerenic acid and/or its pharmaceutically acceptable salt and/or solvate within a short time after administration. Typically, an IR dosage form will have released 70% by weight of the pharmaceutically active agents within thirty minutes of administration. The release rates may be determined using the European Pharmacopoeia Paddle Method.

A controlled release dosage form may designate a pharmaceutical dosage form that releases the active agent only after the dosage form has reached a certain site of the body, i.e. the stomach or the gastro-intestinal tract. Additionally or alternatively it may designate a dosage form, which releases the active agent over a prolonged period of time. In the latter case, a controlled release dosage form may be designated as a sustained release dosage form.

A site-specific controlled release of the pharmaceutically active agent, being in the present case at least one valerenic acid derivative and/or a pharmaceutically acceptable salt and/or solvate thereof, may e.g. be achieved in that the release is made dependent on the pH value of the liquids that the dosage form encounters when passing through the human body. Such a pH-dependent release may allow that a dosage form releases the active agent not in the stomach, but only in the gastro-intestinal tract. Another embodiment would be that such a controlled release dosage form releases the active agent once it enters the body. A typical example of controlled release dosage form which pH-independently releases the active agent are dosage forms that comprise an enteric coating.

The term "sustained release" instead refers to the release of the pharmaceutically active compounds from the dosage form over an extended period of time but not necessarily to the release at a defined place. In general, sustained release in the context of the present invention means that a pharmaceutically active agent such as at least one valerenic acid derivative and/or its pharmaceutically acceptable salt and/or solvate are released from the pharmaceutical dosage form over a time period of at least 2 hours. Of course, the release of the pharmaceutically active agent from the dosage form may also take place over time periods of at least 4 hours, at least 6 hours, at least 10 hours, at least 12 hours or at least 14 hours.

The sustained release characteristics of a dosage form may be adapted such that a therapeutic effect is achieved for at least 8 hours, for at least 12 hours or for at least 24 hours. Such pharmaceutical dosage forms have the advantage that they can be administered on a 3-times, 2-times or once-a-day basis to the patient.

Of course, the above principles can be combined. For example, a pharmaceutical dosage form may comprise an enteric coating in order to ensure that the active agent is released only in the gastro-intestinal tract. The release during the gastro-intestinal passage may, however, display the characteristics of sustained release.

Additionally and/or alternatively the principles of immediate release and sustained release may be combined. Thus, a dosage form may comprise an immediate release phase that ensures a quick onset of therapeutic action that is then prolonged by a second phase of the pharmaceutical dosage form ensuring sustained release characteristics.

Sustained release characteristics can be achieved by different formulation approaches. For example, a pharmaceutical dosage form may comprise a sustained release matrix in which the pharmaceutically active agent such as the at least one valerenic acid derivative and/or its pharmaceutically acceptable salt and/or solvate is embedded in order to achieve the sustained release properties of the dosage form.

In another embodiment, a sustained release coating may be used to ensure the sustained release characteristics of the dosage form. In such a case, the pharmaceutically active agent such as the at least one valerenic acid derivative and/or its pharmaceutically acceptable salt and/or solvate may be applied on/or within e.g. a carrier, which has no substantial influence on the release of the active agent. This drug-loaded carrier may then be overcoated with a corresponding sustained release coating.

These approaches for achieving sustained release of a pharmaceutically active agent, i.e. use of a matrix or a coating may of course, also be combined. The person skilled in the art is further aware of other technical approaches for achieving a sustained release of the dosage form which include e.g. osmotically driven sustained dosage forms.

Typically, if a sustained release matrix system is used, the pharmaceutically active agent such as the at least one valerenic acid derivative and/or its pharmaceutically acceptable salt and/or solvate will be dispersed throughout a matrix-forming material. The matrix-forming materials may be chosen to achieve an erosive matrix, a diffusion matrix or a matrix system, which combines the characteristics of an erosive and a diffusion matrix. Suitable materials for inclusion in a sustained release matrix include hydrophilic or hydrophobic polymers including cellulose ether and preferably alkyl celluloses and hydroxyl alkyl celluloses as well as acrylic resins. Other materials that may be used in a sustained release matrix may be fatty alcohols, fatty acids or polyethylene glycols. The person skilled in the art will be aware of how to build such pharmaceutical dosage forms.

According to another aspect of the present invention, the dosage form contains the at least one valerenic acid derivative and/or its pharmaceutically acceptable salt and/or solvate compressed together with an excipient. It may be especially preferred to prepare the inventive dosage from the at least one valerenic acid derivative and/or its pharmaceutically acceptable salt and/or solvate with a polymer. In this context, suitable polymers according to the present invention may be selected form the group comprising alginic acid, carboxymethylcellulose calcium, carboxymethylcellulose sodium, colloidal silicon dioxide, guar gum, magnesium aluminum silicate, methylcellulose, microcrystalline cellulose, cellulose, pregelatinized starch, sodium alginate, starch, ethylcellulose, gelatin, hydroxyethyl cellulose, hydroxypropyl cellulose, hydroxypropylmethyl cellulose, polymethacrylate, povidone, shellac and zein.

In one preferred embodiment of the present invention the pharmaceutically active agent is administered together with an auxiliary agent improving or influencing the availability or solubility of the pharmaceutically active agent. Suitable additional agents that may be used in this context are emulsifying agents and solubilizer, such as e.g. Tween 80, Soy oil or Lecithin.

As set out above, the medicament may be formulated for topical application. Suitable pharmaceutical application forms for such an application may be a topical nasal spray, sublingual administration forms and controlled and/or sustained release skin patches.

The pharmaceutical compositions in accordance with the present invention may not only comprise the at least one valerenic acid derivative and/or its pharmaceutically acceptable salt and/or solvate but also another pharmaceutically active agents and preferably one or more pharmaceutically active agents which are known to have a positive effect on the treatment and/or prevention of e.g. insomnia and anxiety when administered to a patient in need of treatment thereof.

As regards human patients, the at least one valerenic acid derivative and/or pharmaceutically acceptable salt and/or solvate thereof may be administered to a patient in an amount of about 25 mg to 5,000 mg, preferably of about 100 mg to about 2,500 mg per day. A human patient may in particular be treated with about 500 mg to about 1,500 mg and more specifically with about 1,000 mg per day of the at least one valerenic acid derivative and/or pharmaceutically acceptable salt and/or solvent thereof.

Another suitable criterion for selecting an appropriate amount of the at least one valerenic acid derivative and/or of a pharmaceutically acceptable salt and/or solvate thereof is that the at least one valerenic acid derivative and/or pharmaceutically acceptable salt and/or solvate thereof may be administered to an individual in an amount of about 1 to about 100 mg/kg/d, preferably in an amount of about 5 to about 50 mg/kg/d, more preferably in an amount of about 10 to about 25 mg/kg/d and in particular in an amount of about 12 to about 15 mg/kg/d.

Particularly preferred is the formulation of a medicament for the oral application. In an embodiment where at least one valerenic acid derivative is used for the oral application, one will consider to use about 1 to about 10,000 mg, about 25 to about 5,000 mg, about 50 to about 1,500 mg or about 250 to about 500 mg of the at least one valerenic acid derivative or at least one pharmaceutically acceptable salt and/or solvate thereof for the pharmaceutical compositions, uses and methods for treating inter alia insomnia and anxiety as mentioned above.

These amounts can be administered at once or as multiple doses (at least 2, 3, 4, 5 or 10 doses) per day.

A pharmaceutical composition comprising at least one compound of the present invention may be used for the treatment of a disorder selected from the group of disorders comprising insomnia, anxiety, pain, mood and panic disorders, epilepsy, schizophrenia and disorders/symptoms connected to alcohol and/or substance withdrawal/abuse. A pharmaceutical composition comprising at least one compound of the present invention may thus inter alia be used as analgesic, anesthetic, sedative, hypnotic, anxiolytic, antiepileptic.

Furthermore, compounds of the present invention may be used for the diagnosis and/or treatment of anxiety, Down Syndrome, sleep, cognitive and seizure disorders, depression, overdose with benzodiazepine drugs, enhancement of memory and alertness, Huntington's Chorea, muscular spasms and rigidity, sleep and seizure disorders, and withdrawal symptoms. Also, compounds of the present invention may inter alia be used to diagnose and treat Alzheimer's disease, Parkinson's disease and for enhancing cognition and reversing sedation after application of general anesthesia during surgery, wherein said compounds act preferably as antagonists. Compounds of the present invention may also inter alia be useful as modulators in the prevention of anxiety disorders, such as panic disorder with or without agoraphobia, agoraphobia without history of panic disorder, phobias including social phobias, obsessive-compulsive disorder, stress disorders including post-traumatic and acute stress disorder, and generalized or substance-induced anxiety disorder, depression or bipolar disorders such as single-episode or recurrent major depressive disorder, dysthymic disorder, bipolar I and bipolar II manic disorders, neuroses, schizophrenia, attention deficit hyperactivity disorder and disorders of circadian rhythm, e.g. in subjects suffering from the effects of jet lag or shift work, convulsive or seizure disorders such as epilepsy and pain. Furthermore, the compounds of the present invention may be used as general anaesthetics.

4. Examples

In the following, examples of embodiments of the present invention are outlined. However, said examples should not be construed as limiting the scope of the present invention.

4.1. Synthesis of Valerenic Acid and Valerenic Acid Derivatives

General Procedures

All reactions were carried out in oven-dried glassware under an argon atmosphere unless stated otherwise Anhydrous $CH_2Cl_2$ was distilled under Argon from $P_2O_5$, diethylether and benzene from sodium, DMSO, triethylamin, and diisopropylethylamin from $CaH_2$ and anhydrous THF and MTBE were purchased from Acros (99.85%, water <50 ppm). All other solvents were HPLC grade. Commercially available reagents were used without further purification besides stated otherwise. Reactions were magnetically stirred and monitored by thin layer chromatography with E. Merck silica gel 60 $F_{254}$ plates. Flash column chromatography was performed with Merck silica gel (0.04-0.063 mm, 240-400 mesh) under pressure besides stated otherwise. Yields refer to chromatographically and spectroscopically pure compounds unless stated otherwise.

$^1$H NMR (400 MHz or 600 MHz) and $^{13}$C NMR (100 MHz or 150 MHz) spectra were either recorded on Bruker Avance Avance 400, DRX 400, or Avance 600 spectrometers. Besides stated otherwise all NMR spectra were measured in $CDCl_3$ solutions. The chemical shifts δ are reported relative to the residual solvent peaks.

All $^1$H and $^{13}$C shifts are given in ppm (s=singulet; d=doublet; t=triplet; q=quadruplet; m=multiplet; b=broad signal). If possible, assignments of proton resonances were confirmed by correlated spectroscopy. Optical rotations were measured at 20° C. on a P 341 Perkin-Elmer polarimeter. IR spectra were recorded of samples prepared as films on silicium plates on a Perkin-Elmer Spectrum 1600 Series FTIR spectrometer. MS spectra were measured on a Finnigan MAT 8230 apparatus with a resolution of 10000. Compound names were generated using AutoNom.

4.1.1. Synthesis of Valerenic Acid

This example follows the general reaction scheme as depicted in scheme 1 above.

(S)-Hex-5-yne-1,2-diol (1)

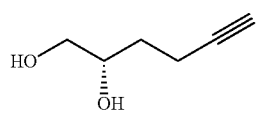

A mixture of magnesium turnings (4.745 g, 195.2 mmol), mercury-(II)-chloride (269.1 mg, 0.991 mmol) and a single crystal of iodide in freshly distilled ether (100 mL) was carefully treated with propargyl bromide (80% in toluene, 10.5 mL, 11.59 mg, 97.4 mmol) dissolved in freshly distilled ether (40 mL). After the reaction had started the mixture was cooled to 0° C. and the rest of the propargyl bromide solution was added within 1 hour. After being cooled at 0° C. for an additional hour the reaction mixture was warmed to room temperature and stirred for another hour.

(R)-Glycidol (97%, 1.0 mL, 1.077 g, 14.53 mmol) was dissolved in freshly distilled ether and cooled to −78° C. Under vigorous stirring this solution was treated with freshly prepared propargylmagnesium bromide (112.5 mL, 72.788 mmol) very slowly within 1 hour. During the night the mixture was slowly warmed to room temperature. After 14 hours the reaction was quenched with saturated aqueous $NH_4Cl$. For a better phase separation potassium sodium tartrate was added and the solution was extracted with ether (4×) and ethyl acetate (4×). The combined extracts were dried ($Na_2SO_4$) and concentrated in vacuo. Purification by chromatography (hexane/EtOAc 10/1 to pure EtOAc) provided 1.560 g of compound (I) as clear yellow oil with 94% yield.

$^1$H-NMR (400 MHz, $CDCl_3$, ppm): 3.89 (ddd, 1H, J=3.2 Hz, J=7.0 Hz, J=13.1 Hz), 3.68 (dd, 1H, J=3.2 Hz, J=11.1 Hz), 3.49 (dd, 1H, J=7.3 Hz, J=11.1 Hz), 2.47 (b, 1H), 2.36 (dt, 2H, J=2.7 Hz, J=7.0 Hz), 2.16 (b, 1H), 1.99 (t, 1H, J=2.7 Hz), 1.66 (dd, 2H, J=6.8 Hz, J=13.6 Hz)

$^{13}$C-NMR (100 MHz, $CDCl_3$, ppm): 83.9, 71.2, 69.2, 66.7, 31.7, 15.0

IR (film, $cm^{-1}$): 3296, 2924, 2853, 1654, 1437, 1099, 1044, 944, 890, 636

HRMS (ESI, m/z): $[M]^+$ calc.: 114.0681; found: 114.0680.

$[α]_D^{20}$=−19.9 (c=0.72 g/100 mL, DCM)

Toluene-4-sulfonic acid (S)-2-hydroxy-hex-5-ynyl ester (2a)

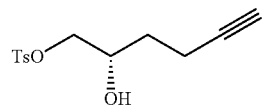 [SMILES: C#CCC[C@H](O)COS(=O)(=O)c1ccc(C)cc1]

Diol (1) (1.560 g, 13.667 mmol) was dissolved in DCM (140 mL) cooled to 0° C. and dibutyltin oxide (67.9 mg, 0.2728 mmol), triethylamine (2.08 mL, 1.518 g, 15.005 mmol) and toluenesulfonyl chloride (2.864 g, 15.022 mmol) were added. After 10 minutes the icebath was removed and the reaction mixture was stirred for 22 hours. Then it was filtrated and the filtrate concentrated in vacuo. Purification by chromatography (hexane/EtOAc 4/1) provided 2.950 g of compound (2a) as clear colourless oil with 80% yield.

$^1$H-NMR (400 MHz $CDCl_3$, ppm): 7.81 (d, 2H, J=8.3 Hz) 7.36 (d, 2H, J=8.0 Hz) 4.10-3.99 (m, 2H), 3.94 (dd, 1H, J=6.4 Hz, J=9.6 Hz), 2.46 (s, 3H), 2.38-2.28 (m, 2H), 2.18 (d, 1H, J=4.6 Hz), 1.95 (t, 1H, J=2.7 Hz), 1.64 (dd, 2H, J=6.8 Hz, J=13.6 Hz)

$^{13}$C-NMR (100 MHz, $CDCl_3$, ppm): 145.3, 132.8, 130.1, 128.1, 83.3, 73.7, 69.4, 68.4, 31.3, 21.8, 14.7 m IR (film, $cm^{-1}$): 3360, 2922, 2852, 1654, 1458, 1355, 1174, 965, 668, 554, 421, 416

HRMS (ESI, m/z): $[M]^+$ calc.: 268.0769; found: 268.0764.

$[α]_D^{20}$=−0.4 (c=1.24 g/100 mL, DCM)

tert-Butyl-dimethyl-((S)-1-vinyl-pent-4-ynyloxy)-silane (4a)

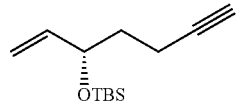

A suspension of trimethylsulfonium iodide (4.032 g, 19.758 mmol) in THF (60 mL) was treated with 1.6 M n-BuLi (11.75 mL, 18.8 mmol) at −15° C. After stirring for 30 minutes Tosylate (2a) (1.002 g, 3.733 mmol) dissolved in THF (30 mL) was added dropwise within 45 minutes. The resulting reaction mixture was stirred at the same temperature for 1 hour, slowly warmed to room temperature during the night, before it was quenched by the addition of water. The solution was extracted with ether (4×), the combined organic phases were washed with brine, dried ($Na_2SO_4$) and due to the volatility of (S)-hept-1-en-6-yne-3-ol carefully concentrated in reduced vacuo.

The crude (S)-hept-1-en-6-yne-3-ol (3a) was dissolved in DCM and cooled to 0° C. Triethylamin (1.55 mL, 1.132 g, 11.182 mmol) and tert-Butyldimethylsilyl triflate (2.15 mL, 2.475 g, 9.362 mmol) were added and the solution was stirred for 1 hour at 0° C. before it was warmed to room temperature. After stirring for another hour water was added and the solution was extracted with DCM (3×). The combined organic phases were washed with brine, dried ($Na_2SO_4$) and concentrated in vacuo. Chromatography (pentane/ether 200/1) furnished 489 mg of compound (4a) as clear colourless oil with 58% yield.

$^1$H-NMR (400 MHz $CDCl_3$, ppm): 5.78 (ddd, 1H, J=6.1 Hz, J=10.4 Hz, J=17.1 Hz), 5.21-5.03 (m, 2H), 4.23 (dd, 1H, J=6.2 Hz, J=12.2 Hz), 2.32-2.16 (m, 2H), 1.94 (t, 1H, J=2.7 Hz), 1.76-1.62 (m, 2H), 0.90 (s, 9H), 0.07 (s, 3H), 0.04 (s, 3H)

$^{13}$C-NMR (100 MHz, $CDCl_3$, ppm): 141.1, 114.5, 84.6, 72.4, 68.5, 36.8, 26.0, 18.4, 14.5, −4.2, −4.7

IR (film, $cm^{-1}$): 3314, 2929, 2857, 1939, 1645, 1472, 1362, 1251, 1091, 1027, 987, 923, 837, 776, 633

HRMS (ESI, m/z): $[M-C_4H_9]^+$ calc.: 167.0892; found: 167.0894.

$[\alpha]_D^{20}$=−4.9 (c=0.815 g/100 mL, DCM)

tert-Butyl-dimethyl-((S)-1-vinyl-hex-4-ynyloxy)-silane (5a)

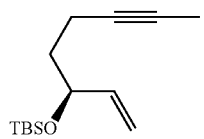 [SMILES: C=C[C@H](CCC#CC)O[Si](C)(C)C(C)(C)C]

Compound (4a) (481.6 mg, 2.146 mmol) was dissolved in THF (21.5 mL) and cooled to −78° C. before treated with 1.6 M n-BuLi (2.7 mL, 4.32 mmol) dropwise. The resulting solution was stirred 15 minutes at the same temperature and then methyl iodide (0.67 mL, 1.528 g, 10.765 mmol) was added. During the night the mixture was slowly warmed to room temperature. After 13 hours the reaction was quenched with water. The solution was extracted with ether (3×), the combined extracts were washed with brine, dried ($Na_2SO_4$) and concentrated in vacuo. Purification by chromatography (pentane/ether 200/1) provided 395.5 mg of compound (5a) as clear colourless oil with 77% yield.

$^1$H-NMR (400 MHz $CDCl_3$, ppm): 5.78 (ddd, 1H, J=17.1 Hz, J=10.4 Hz, J=6.0 Hz), 5.20-5.01 (m, 2H), 4.21 (td, 1H, J=6.8 Hz, J=5.8 Hz), 2.25-2.09 (m, 2H), 1.78 (t, 3H, J=2.6 Hz), 1.69-1.58 (m, 2H), 0.90 (s, 9H), 0.07 (s, 3H), 0.04 (s, 3H)

$^{13}$C-NMR (100 MHz, $CDCl_3$, ppm): 141.4, 114.1, 79.1, 75.8, 72.6, 37.4, 26.0, 18.4, 14.8, 3.6, −4.2, −4.8

IR (film, $cm^{-1}$): 2929, 2857, 1472, 1361, 1251, 1089, 989, 922, 837, 776

HRMS (ESI, m/z): $[M-C_4H_9]^+$ calc.: 181.1049; found: 181.1052.

$[\alpha]_D^{20}$=−4.8 (c=1.665 g/100 mL, DCM)

tert-Butyl-((S)-3-isopropenyl-cyclopent-2-enyloxy)-dimethyl-silane (6a)

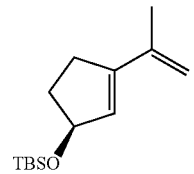 [SMILES: C=C(C)C1=C[C@@H](O[Si](C)(C)C(C)(C)C)CC1]

A solution of compound (5a) (263.8 mg, 1.106 mmol) and degassed DCM (37) was cooled to −78° C. The flask was flushed with ethylene gas over a period of 10 minutes before ethylene gas was bubbled through the solution itself for 3 additional minutes. Grubbs I catalyst (136.4 mg, 0.1657 mmol) was added and once again ethylene gas was bubbled through the resulting mixture for one minute. The icebath was removed and the mixture stirred for 24 hours. The flask was flushed with argon and the solvent was evaporated. Chromatography of the residue (pentane/ether 200/1) furnished 226.6 mg of compound of (6a) as clear colourless oil with 86% yield.

$^1$H-NMR (400 MHz $CDCl_3$, ppm): 5.68 (d, 1H, J=1.4 Hz), 5.00-4.94 (m, 3H), 2.69-2.59 (m, 1H), 2.39-2.25 (m, 2H), 1.93 (s, 3H), 1.80-1.69 (m, 1H), 0.91 (s, 9H), 0.09 (s, 6H)

$^{13}$C-NMR (100 MHz, $CDCl_3$, ppm): 146.0, 140.0, 129.9, 114.2, 78.5, 34.3, 30.7, 26.2, 20.7, 18.5, −4.3, −4.4

IR (film, $cm^{-1}$): 3360, 2927, 2855, 1661, 1634, 1600, 1464, 1361, 1251, 1108, 1051, 1005, 910, 835, 775

HRMS (ESI, m/z): $[M]^+$ calc.: 238.1753; found: 238.1750.

$[\alpha]_D^{20}$=−98.6 (c=1.96 g/100 mL, DCM)

(S)-3-Isopropenyl-cyclopent-2-enol (7a)

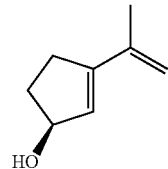

A solution of compound (6a) (402.8 mg; 1.689 mmol) in THF (34 mL) was cooled to 0° C. and treated with 1.0 M tert-Butylammonium floride (2.55 mL, 2.55 mmol). The next 3½ hours the reaction mixture was stirred at room temperature and then quenched with saturated aqueous $NH_4Cl$. The resulting solution was extracted with DCM (3×) and AcOEt (1×), dried ($Na_2SO_4$) and concentrated in vacuo. Purification by chromatography (pentane/ether 3/1 to 2/1) provided 190.4 mg of compound (7a) as clear yellow oil with 95% yield.

$^1$H-NMR (400 MHz $CDCl_3$, ppm): 5.80 (d, 1H, J=1.7 Hz, 5.02 (s, 2H), 4.96-4.89 (m, 1H), 2.73-2.63 (m, 1H), 2.45-2.31 (m, 2H), 1.94 (s, 3H), 1.80-1.73 (m, 1H), 1.44 (d, 1H, J=7.4 Hz)

$^{13}$C-NMR (100 MHz, $CDCl_3$, ppm): 147.7, 139.8, 129.0, 114.9, 78.1, 34.1, 30.6, 20.7

IR (film, $cm^{-1}$): 3324, 2924, 2854, 1599, 1458, 1032, 970, 888

HRMS (ESI, m/z): $[M]^+$ calc.: 124.0888; found: 124.0884.

$[\alpha]_D^{20}$=−119.3 (c=0.825 g/100 mL, DCM)

(2aR,7aS,7bR)-5-Methyl-3,4,6,7,7a,7b-hexahydro-2aH-indeno [1,7-bc]furan-2-one (8a)

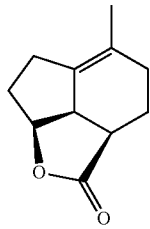

Anhydrous MgBr$_2$.Et$_2$O (759.2 mg, 2.940 mmol) was suspended in DCM (3.5 mL), treated with Diisopropylethylamin (1.0, 760 mg, 5.880 mmol) and stirred for 15 minutes until the suspension turns magenta. Then compound (7a) (182.4 mg, 1.469 mmol) dissolved in DCM (11.5) was added slowly within 15 minutes. After stirring for 1 hour Methylacrylate (0.27 mL, 257.9 mg, 2.995 mmol) was added dropwise. The resulting mixture was stirred for 5½ hours before it was quenched with saturated aqueous NH$_4$Cl. For a better phase separation potassium sodium tartrate was added and the solution extracted with DCM (4×). The combined extracts were dried (Na$_2$SO$_4$) and concentrated in vacuo. Purification by chromatography (hexane/EtOAc 6/1) furnished 194.3 mg of compound (8a) as white solid with 74% yield.

$^1$H-NMR (400 MHz CDCl$_3$, ppm): 4.84 (dt, 1H, J=1.0 Hz, J=5.5 Hz), 3.02 (ddd, 1H, J=3.2 Hz, J=6.0 Hz, J=6.5 Hz), 2.88-2.80 (m, 1H), 2.63-2.51 (m, 1H), 2.32-2.18 (m, 1H), 2.15-1.87 (m, 6H), 1.65 (s, 3H)

$^{13}$C-NMR (100 MHz, CDCl$_3$, ppm): 178.7, 130.4, 129.3, 83.4, 43.8, 39.7, 29.1, 27.5, 27.2, 20.2, 20.0

IR (film, cm$^{-1}$): 2925, 1763, 1449, 1335, 1142, 1020, 985, 932, 877

HRMS (ESI, m/z): [M]$^+$ calc.: 178.0994; found: 178.0997.

$[\alpha]_D^{20}$=−94.4 (c=0.71 g/100 mL, DCM)

(E)-3-((3S,3aR,4S)-3-Hydroxy-7-methyl-2,3,3a,4,5,6-hexahydro-1H-inden-4-yl)-2-methyl-acrylic acid ethyl ester (10a)

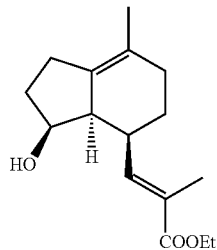 [SMILES: CCOC(=O)/C(C)=C/[C@@H]1CCC(C)=C2CC[C@H](O)[C@@H]21]

A solution of compound (8a) (183.5 mg, 1.030 mmol) in DCM (10) was cooled to −78° C. and 1.0 M diisobutylammoniumhydride (1.5 mL, 1.5 mmol) was added dropwise. After stirring the mixture for 2¼ hours the reaction was quenched by the addition of AcOEt (1 mL) and stirred for another 15 minutes. Saturated aqueous Potassium sodium tartrate was added and the mixture warmed to room temperature. The aqueous layer was separated and extracted with DCM (5×). The combined organic phases were dried (Na$_2$SO$_4$) and concentrated in vacuo. Filtration through a short pad of silica gel afforded a crude mixture of the two isomers of lactol (9a) as clear slightly yellow oil.

Lactol (9a) was dissolved in benzene (10 mL), (1-ethoxy-carbonylethyliden)triphenyl-phosphorane (94%, 794.2 mg, 2.060 mmol) was added and heated under reflux for 24 hours. Saturated aqueous NH$_4$Cl was added and the solution extracted with DCM (4×). The combined extracts were dried (Na$_2$SO$_4$) and concentrated in vacuo. Purification by chromatography (hexane/EtOAc 10/1 to 5/1) furnished 226.9 mg of compound (10a) as clear colourless oil with 83% yield.

$^1$H-NMR (400 MHz CDCl$_3$, ppm): 7.06 (dd, 1H, J=1.4 Hz, J=10.5 Hz), 4.29 (dd, 1H, J=3.4 Hz, J=6.0 Hz), 4.24-4.11 (m, 2H), 3.12 (ddd, 1H, J=5.0 Hz, J=8.8 Hz, J=10.2 Hz), 2.58-2.22 (m, 3H), 2.09-1.59 (m, 12H), 1.31 (d, 1H, J=3.4 Hz), 1.27 (t, 3H, J=7.1 Hz)

$^{13}$C-NMR (100 MHz, CDCl$_3$, ppm): 168.2, 143.5, 132.0, 127.6, 125.5, 75.3, 60.7, 50.2, 34.0, 33.1 29.3, 27.7, 26.0, 19.5, 14.4, 12.7

IR (film, cm$^{-1}$): 3480, 2926, 1704, 1645, 1447, 1367, 1246, 1110, 1033, 753

HRMS (ESI, m/z): [M-H$_2$O]$^+$ calc.: 246.1620; found: 246.1614.

$[\alpha]_D^{20}$=−5.4 (c=0.895 g/100 mL, DCM)

(E)-3-((3S,3aS,4S,7R,7aR)-3-Hydroxy-7-methyl-octahydro-inden-4-yl)-2-methyl-acrylic acid ethyl ester (11a)

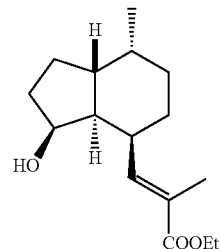 [SMILES: CCOC(=O)/C(C)=C/[C@@H]1CC[C@@H](C)[C@H]2CC[C@H](O)[C@@H]21]

A solution of compound (10a) (223.8 mg, 0.8466 mmol) and degassed DCM (34) was cooled to 0° C. The flask was flushed with hydrogen over a period of 2 minutes before hydrogen was bubbled through the solution itself for one additional minute. After adding Crabtree catalyst (68.0 mg, 0.0845 mmol) the flask was once again flashed with hydrogen for 3 minutes before hydrogen was bubbled through the solution for 2 minutes until it became colorless. The icebath was removed and the mixture stirred for 2¼ hours. Argon was bubbled through the reaction mixture and the solvent was evaporated. Chromatography (hexane/EtOAc 7/1 to 3/1) of the residue furnished 162.7 mg of compound of (11a) as white solid with 72% yield.

$^1$H-NMR (400 MHz CDCl$_3$, ppm): 7.38 (dd, 1H, J=1.4 Hz, J=10.7 Hz), 4.26-4.12 (m, 3H), 3.13-3.04 (m, 1H), 2.45-2.34 (m, 1H), 2.26-2.16 (m, 1H), 1.94-1.46 (m, 9H), 1.41-1.24 (m, 7H), 0.90 (d, 3H, J=7.2 Hz)

$^{13}$C-NMR (100 MHz, CDCl$_3$, ppm): 168.2, 144.0, 127.0, 75.5, 60.7, 46.7, 37.2, 35.3, 33.2, 29.8, 28.7, 27.0, 24.8, 14.5, 12.6, 12.1

IR (film, cm$^{-1}$): 3483, 2926, 1701, 1636, 1459, 1367, 1247, 1171, 1106, 1042, 750

HRMS (ESI, m/z): [M]$^+$ calc.: 266.1882; found: 266.1890.

$[\alpha]_D^{20}$=−118.7 (c=0.715 g/100 mL, DCM)

(E)-2-Methyl-3-((3aS,4S,7R,7aR)-7-methyl-3-oxo-octahydro-inden-4-yl)-acrylic acid ethyl ester (12a)

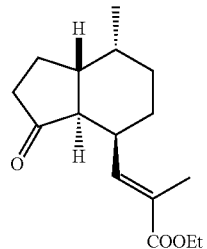 [SMILES: CCOC(=O)/C(C)=C/[C@@H]1CC[C@@H](C)[C@H]2CCC(=O)[C@@H]21]

Compound (11a) (157.9 mg, 0.5928 mmol) was dissolved in DMSO (2.4 mL) and treated with a solution of IBX (335.6 mg, 1.199 mmol) in DMSO (4.8). After stirring for 2½ hours water was added and the white precipitate removed by filtration. The precipitate was washed with DMSO/water and a small amount of AcOEt. The filtrate was extracted with DCM (4×), the combined organic phases were dried (Na$_2$SO$_4$) and concentrated in vacuo. Purification by chromatography (hexane/EtOAc 7/1) provided 146.5 mg of compound of (12a) as clear pale yellow oil with 93% yield.

$^1$H-NMR (400 MHz CDCl$_3$, ppm): 6.83 (ddd, 1H, J=1.4 Hz, J=2.8 Hz, J=10.2 Hz), 4.16 (dq, 2H, J=1.4 Hz, J=7.1 Hz), 3.24-3.16 (m, 1H), 2.32-2.21 (m, 3H), 2.14-1.86 (m, 6H), 1.79-1.68 (m, 2H), 1.63-1.39 (m, 3H), 1.27 (t, 3H, J=7.1 Hz), 0.97 (d, 3H, J=6.9 Hz)

$^{13}$C-NMR (100 MHz, CDCl$_3$, ppm): 217.4, 168.4, 139.9, 129.5, 60.6, 51.4, 40.1, 37.8, 32.6, 30.4, 28.4, 25.6, 24.5, 14.4, 13.0, 11.6

IR (film, cm$^{-1}$): 2925, 2855, 1743, 1713, 1465, 1366, 1312, 1246, 1210, 1157, 1111, 1043, 752

HRMS (ESI, m/z): [M]$^+$ calc.: 264.1725; found: 264.1727.
[α]$_D^{20}$=−160.9 (c=0.86 g/100 mL, DCM)
Valerenic Acid Ethyl Ester (14a)

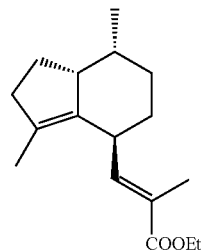 [SMILES: CCOC(=O)/C(C)=C/[C@@H]1CC[C@@H](C)[C@H]2CCC(C)=C12]

A solution of compound (12a) (16.1 mg, 0.0609 mmol) and DCM (2.4 mL) was cooled to 0° C. and treated with freshly distilled triflic anhydride (101 μL, 171.7 mg, 0.609 mmol) and pyridine (49 μL, 48.1 mg, 0.608 mmol) under vigorous stirring. The icebath was removed after 15 minutes and the mixture stirred for 24 hours. The reaction mixture was cooled to 0° C. and washed consecutively with saturated aqueous CuSO$_4$ and saturated aqueous NaHCO$_3$. Both aqueous layers were extracted with DCM (1×). The combined organic phases were washed with brine, dried (Na$_2$SO$_4$) and concentrated in vacuo. Filtration through a short pad of silica gel afforded a crude mixture of the two isomers as clear colorless oil.

The mixture of isomers was dissolved in THF (1.2 mL) and cooled to 0° C. before tetrakis(triphenylphosphine)palladium (6.9 mg, 0.00597 mmol) was added. After stirring for 15 minutes the resulting brown solution was treated with 1.0 M dimethylzinc (0.24 mL, 0.24 mmol). The mixture was allowed to warm to room temperature after another 15 minutes and was stirred for 15½ hours. After cooling to 0° C. water and saturated aqueous NH$_4$Cl were added and the solution was extracted with ether (3×). The combined extracts were washed with brine, dried (Na$_2$SO$_4$) and concentrated in vacuo. Purification by chromatography (hexane/AcOEt 50/1) with silica gel treated with 10% AgNO$_3$ furnished 12.4 mg of compound (14a) as clear colourless oil with 78% yield.

$^1$H-NMR (600 MHz CDCl$_3$, ppm): 7.01 (ddd, 1H, J=9.81 Hz, J=2.78 Hz, J=1.34 Hz), 4.18 (dq, 2H, J=7.10 Hz, J=1.08 Hz), 3.53 (dd, 1H, J=9.62 Hz, J=5.17 Hz), 2.96 (ddd, 1H, J=8.99 Hz, J=4.42 Hz, J=2.29 Hz), 2.19 (t, 2H, J=7.60 Hz), 2.02-1.96 (m, 1H), 1.90-1.71 (m, 6H), 1.63 (td, 3H, J=2.08 Hz, J=1.13 Hz), 1.57-1.51 (m, 1H), 1.45-1.36 (m, 2H), 1.29 (t, 3H, J=7.12 Hz), 0.78 (d, 3H, J=7.01 Hz)

$^{13}$C-NMR (150 MHz, CDCl$_3$, ppm): 168.8, 143.4, 133.6, 131.0, 126.1, 60.6, 47.5, 37.6, 34.5, 33.2, 28.9, 25.6, 24.7, 14.5, 13.7, 12.5, 12.2

IR (film, cm$^{-1}$): 2926, 1712, 1645, 1455, 1379, 1238, 1131, 1104, 1061, 753

HRMS (ESI, m/z): [M]$^+$ calc.: 262.1933; found: 262.1935.
[α]$_D^{20}$=−106.1 (c=0.70 g/100 mL, DCM)
Valerenic Acid

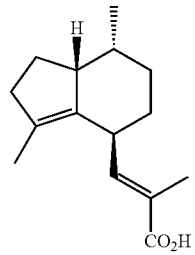 [SMILES: CC1=C2[C@H](/C=C(\C)C(=O)O)CC[C@@H](C)[C@H]2CC1]

A solution of valerenic ethyl ester (14a) (12.4 mg, 0.0473 mmol), methanol (0.5 mL) and THF (0.5 mL) was treated with 1.0 molar aqueous LiOH (0.36 mL, 0.36 mmol). After stirring 24 hours the resulting mixture was cooled to 0° C., acidified with 10% citric acid and extracted with EtOAc (4×). The combined organic phases were washed with a small amount of brine, dried (Na$_2$SO$_4$) and concentrated in vacuo. Purification by chromatography (hexane/EtOAc 5/1 to pure EtOAc) afforded 11.0 mg of valerenic acid with 99% yield.

$^1$H-NMR (600 MHz CDCl$_3$, ppm): 7.15 (ddd, 1H, J=9.96 Hz, J=2.66 Hz, J=1.26 Hz), 3.54 (dd, 1H, J=9.66 Hz, J=5.02 Hz), 2.95 (ddd, 1H, J=8.27 Hz, J=3.98 Hz, J=1.93 Hz), 2.20 (t, 2H, J=7.59 Hz), 1.99 (dt, 1H, J=7.19 Hz, J=3.66 Hz), 1.93-1.71 (m, 6H), 1.63 (td, 3H, J=1.96 Hz, J=1.02 Hz), 1.59-1.51 (m, 1H), 1.48-1.36 (m, 2H), 0.78 (d, 3H, J=7.00 Hz)

$^{13}$C-NMR (150 MHz, CDCl$_3$, ppm): 173.2, 146.6, 133.5, 131.7, 125.4, 47.8, 37.9, 35.0, 33.5, 29.2, 25.8, 25.0, 13.9, 12.5 (2×C)

IR (film, cm$^{-1}$): 2931, 1683, 1652, 1558, 1423, 1299, 1256, 904, 671, 575

HRMS (ESI, m/z): [M]$^+$ calc.: 234.1620; found: 234.1623.
[α]$_D^{20}$=−159.9 (c=0.76 g/100 mL, DCM), authentic sample: [α]$_D^{20}$=−161.2 (c=0.85 g/100 mL, DCM).

m.p.: 139-141° C., authentic sample: m.p.: 140-142° C.

4.1.2. Synthesis of valerenic acid amide (VA-A)

Valerenic acid (18.9 mg, 0.0807 mmol) was dissolved in THF (3 mL) and cooled to 0° C. Triethylamin (12.0 μL, 8.76 mg, 0.0866 mmol) and methyl chloroformate (97%, 8.5 μL, 9.36 mg, 0.0862 mmol) were added. After stirring for 1 hour the resulting solution was treated with aqueous ammonia (25% 25 μL, 5.5 mg, 0.3230 mmol). After 30 minutes the reaction mixture was warmed to room temperature and stirred for an additional hour. Then the mixture was filtered and the filtrate concentrated in vacuo. Purification by chromatography (pure diethylether to diethylether/EtOAc 1/1) provided 6.6 mg Valerenic acid and 11.2 mg of Valerenic acid amide as white solid with 92% yield based on recovered starting material.

4.1.3. Synthesis of Valerenic Hydrazide (VA-HY)

Valerenic acid (21.1 mg, 0.0900 mmol) was dissolved in THF (3 mL) and cooled to 0° C. Triethylamin (13.0 µL, 9.49 mg, 0.0938 mmol) and methyl chloroformate (97%, 5.5 µL, 10.46 mg, 0.0964 mmol) were added. After stirring for 1½ hour the resulting solution was treated with 1.0 M hydrazine in THF (0.54 mL, 0.54 mmol). After 30 minutes the reaction mixture was warmed to room temperature and stirred for an additional hour. Then the mixture was filtered and the filtrate concentrated in vacuo. Purification by chromatography (CHCl$_3$/MeOH 25/1) provided 19.4 mg of Valerenic hydrazide as clear colourless oil with 87% yield.

4.1.4. Synthesis of (S)-3-Isopropenyl-cyclopent-2-enol (7a)

(+/−)-3-Isopropenyl-cyclopent-2-enol (1a*)

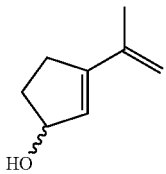

2-Bromopropene (67 µL, 0.7543 mmol) was dissolved in diethylether (0.52 mL) and then cooled to −78° C. After treatment with tert-butyllithium (1.6 M, 0.92 mL, 1.472 mmol) the resulting yellow solution was stirred for 1 hour at the same temperature. In the meantime a solution of cyclopentenone (25 µL, 0.2984 mmol) in anhydrous diethylether (1.8 mL) was cooled to −78° C. The freshly prepared 2-Lithium propenyl (~0.5 M, 1.2 mL, 0.6 mmol) was slowly added and the resulting solution was stirred for 45 minutes before warmed to 0° C. Water (1.8 mL) and tetrahydrofuran (1.8 mL) were added and the biphasic mixture was vigorously stirred for 15 minutes at room temperature. After recooling to 0° C. trifluoroacetic acid (58 µL, 0.7529 mmol) was added and the colourless biphasic solution was vigorously stirred for another 45 minutes before it was quenched with saturated aqueous NaHCO$_3$. The aqueous phase was extracted with dichloromethane (4×) and the combined organic extracts dried (Na$_2$SO$_4$) and concentrated in vacuo. Purification by chromatography (hexane/EtOAc 5/1 to 3/1) provided 31.4 mg of compound 11 as clear colorless oil with 85% yield. The analytical data (NMR, IR, HRMS) was in exact agreement with the data of the single enantiomer (7a) as stated under 4.1.1.

(S)-3-Isopropenyl-cyclopent-2-enol (7a)

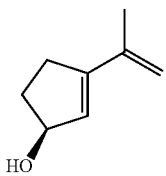

Compound (1a*) (63.9 mg, 0.5146 mmol) was dissolved in anhydrous MTBE (1.7 mL) and lipase PS (20 w %, 12.9 mg) and vinyl acetate (31 µL, 0.3363 mmol) were added before the resulting mixture was heated to 40° C. for 18 hours. Solids were removed by filtration and the filtrate concentrated in vacuo. Purification by chromatography (hexane/EtOAc 10/1 to 5/1 to 3/1 to 1/1) using Merck aluminium oxide 90 (0.063-0.200 mm, 70-230 mesh) furnished 25.7 mg of compound 7a as white solid with 40% yield and 43.4 mg of the enantioenriched acetic acid (R)-3-isopropenyl-cyclopent-2-enyl ester as slightly yellow oil with 51% yield.

The analytical data (NMR, IR, HRMS, optical rotation) was in exact agreement with the aforementioned data as stated under 4.1.1.

4.2. Modulation of GABA Receptors by Valerenic Acid Derivatives 4.2.1. Expression and Functional Characterization of GABA$_A$ Receptors In the next paragraphs, reference is made to the following publications:

Baburin I, Beyl S and Hering S (2006) Automated fast perfusion of *Xenopus oocytes* for drug screening. *Pflugers Arch* 453:117-23; Khom S, Baburin I, Timin EN, Hohaus A, Sieghart W and Hering S (2006) Pharmacological properties of GABAA receptors containing gammal subunits. *Mol Pharmacol* 69:640-9; Khom S, Baburin I, Timin E, Hohaus A, Trauner G, Kopp B and Hering S (2007) Valerenic acid potentiates and inhibits GABA(A) receptors: molecular mechanism and subunit specificity. *Neuropharmacology* 53:178-87; Methfessel C, Witzemann V, Takahashi T, Mishina M, Numa S and Sakmann B (1986) Patch clamp measurements on *Xenopus laevis* oocytes: currents through endogenous channels and implanted acetylcholine receptor and sodium channels. *Pflugers Arch* 407:577-88; and Wittmann W, Schunk E, Rosskothen I, Gaburro S, Singewald N, Herzog H and Schwarzer C (2008) Prodynorphin-Derived Peptides Are Critical Modulators of Anxiety and Regulate Neurochemistry and Corticosterone. *Neuropsychopharmacology*.

The following paragraphs describe the preparation of oocytes expressing specific subtypes ($\alpha_1\beta_3$) of the GABA$_A$ receptor and the analysis of the concentration-response curves.

Preparation of stage V-VI oocytes from *Xenopus laevis* and synthesis of capped off run-off poly(A$^+$) cRNA transcripts from linearized cDNA templates (pCMV vector) were performed as described (Khom et al. 2006). Briefly, female *Xenopus laevis* (NASCO, USA) were anaesthetised by exposing them for 15 minutes to a 0.2% solution of MS-222 (methane sulfonate salt of 3-aminobenzoic acid ethyl ester; Sandoz) before surgically removing parts of the ovaries. Follicle membranes from isolated oocytes were enzymatically digested with 2 mg/ml collagenase (Type 1A, Sigma). One day after isolation, the oocytes were injected with about 10-50 nl of DEPC-treated water (diethyl pyrocarbonate, Sigma, Germany) containing the different cRNAs at a concentration of approximately 300-3000 pg/nl/subunit. The amount of cRNA was determined by means of a Nanoprop ND-1000 (Kisker-biotech, Steinfurt, Germany).

cRNAs were mixed in a ratio of 1:1 for the expression of $\alpha_1\beta_3$ receptors. Oocytes were stored at 18° C. in ND96 solution (Methfessel et al., 1986). Electrophysiological experiments were done using the two-microelectrode voltage-clamp method at a holding potential of −70 mV making use of a TURBO TEC 01C amplifier (npi electronic, Tamm, Germany) and an Axon Digidata 1322A interface (Molecular Devices, Sunnyvale, Calif.). Data acquisition was carried out using pCLAMP v.9.2. The bath solution contained 90 mM NaCl, 1 mM KCl, 1 mM MgCl$_2$.6H$_2$O, 1 mM CaCl$_2$ and 5 mM HEPES (pH 7.4). Microelectrodes were filled with 2M KCl and had resistances between 1 and 3 MΩ (Khom et al., 2007).

GABA and valerenic acid derivatives, respectively, were applied by means of fast perfusion system (see Baburin et al. 2006 for details; Khom et al. 2006). Drug or control solutions were applied by means of a TECAN Miniprep 60 permitting automation of the experiments. To elicit I$_{GABA}$ the chamber was perfused with 120 μl of GABA-containing solution at a rate of between 300 and 1000 μl/s. The $I_{GABA}$ rise time was in the range of between 100 and 250 ms (see Khom et al. 2006). Care was taken to account for possible slow recovery from increasing levels of desensitization in the presence of high GABA, valerenic acid and derivatives concentrations. Oocytes with maximal current amplitudes >3 μA were discarded to exclude voltage-clamp errors (Khom et al., 2006; Baburin et al., 2006; Khom et al., 2007).

Stimulation of chloride currents by modulators of the $GABA_A$ receptor was measured at a GABA concentration eliciting between 3% and 5% of the maximal current amplitude ($EC_{3-5}$). The $EC_{3-5}$ was determined at the beginning of each experiment. Enhancement of the chloride current was defined as $(I_{(GABA+Comp)}/I_{GABA})-1$, where $I_{(GABA+Comp)}$ is the current response in the presence of a given compound (valerenic acid or derivative) and $I_{GABA}$ is the control GABA current. To measure the sensitivity of the $GABA_A$ receptor for a given compound, the compound was applied for an equilibration period of 1 minute before applying GABA ($EC_{3-5}$). Concentration-response curves were generated and the data were fitted by non-linear regression analysis using Origin software (OriginLab Corporation, USA). Data were fitted to the equation:

$$\frac{1}{1+\left(\frac{EC_{50}}{[Comp]}\right)^{n_H}},$$

where $n_H$ is the Hill coefficient. Each data point represents the mean±S.E. from at least 4 oocytes and 2 oocyte batches. Statistical significance was calculated using the paired Student t-test with a confidence interval of p<0.05 (Khom et al., 2007).

4.2.2. Modulation of $I_{GABA}$ by VA Derivatives

Furthermore, the modulation of $I_{GABA}$ by VA derivatives was investigated at a GABA $EC_{3-5}$ concentration in a system as outlined under 4.2.1, i.e. on recombinant $GABA_A$ receptors expressed in Xenopus laevis oocytes. Thus, modulation of $I_{GABA}$ by VA derivatives was studied on $GABA_A$ channels composed of $\alpha_1\beta_3$ subunits. The VA derivatives were diluted in DMSO; however, the maximum DMSO concentration in the bath (0.3%) did not affect $I_{GABA}$ (Khom et al., 2005; Khom et al., 2007).

Figure 2:
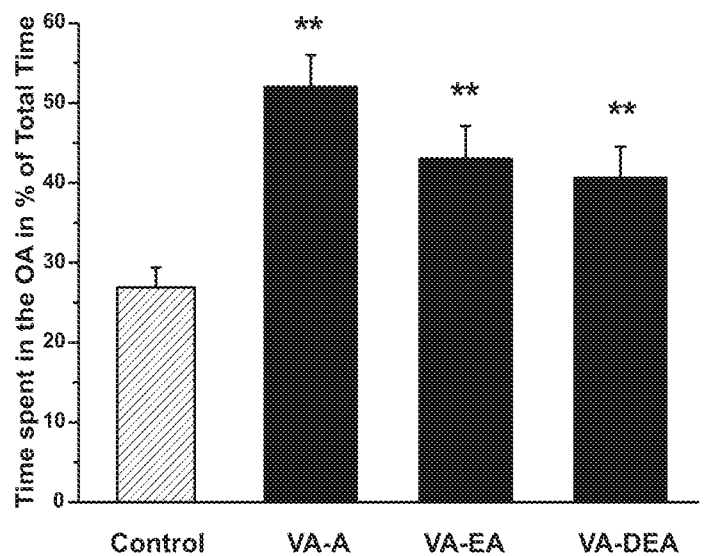
FIG. 2: Behaviour in the Elevated Plus Maze Test (assessed over 5 minutes) for control and VA-derivative-treated mice (concentrations represent mg/kg body weight). Bars indicate the time spent on the open arm in % of the total time. (**) indicates statistical significance (p<0.01).

As shown in FIG. 1, VA derivatives exhibited a positive allosteric modulatory effect at concentrations ≥1 μM by enhancing $I_{GABA}$. Each data point in FIG. 2 represents the mean±S.E. from at least 4 oocytes from 2 batches. The effect was dose-dependent, wherein VA-A revealed a more efficient potentiation, enhancing $I_{GABA}$ by 2247±252% (n=7) compared to VA-IPA (506±76%, with n=5).

The corresponding and additional data referring to efficiencies, potencies and Hill-coefficients ($n_H$) of the aforementioned and further compounds are summarized in Table 1.

TABLE 1

Efficiencies, potencies, $n_H$ and number of experiments for tested VA-derivatives.

|  | $EC_{50}$ (μM) | Maximum stimulation of $I_{GABA}$ ($EC_{3-5}$) (%) | Hill-Coefficient ($n_H$) | Number of experiments (n) |
| --- | --- | --- | --- | --- |
| VA-A | 13.7 ± 2.3 | 2247 ± 252 | 1.6 ± 0.2 | 7 |
| VA-MA | 26.3 ± 6.6 | 2298 ± 312 | 1.4 ± 0.1 | 6 |
| VA-DMA | 28.4 ± 7.1 | 1383 ± 211 | 2.1 ± 0.5 | 5 |
| VA-EA | 23.4 ± 6.9 | 1678 ± 258 | 1.3 ± 0.3 | 5 |
| VA-DEA | 23.7 ± 6.3 | 901 ± 120 | 1.4 ± 0.1 | 6 |
| VA-BA | 18.8 ± 6.9 | 569 ± 57 | 1.1 ± 0.2 | 5 |
| VA-IPA | 22.5 ± 6.0 | 506 ± 76 | 1.5 ± 0.3 | 4 |
| VA-PIP | 54.6 ± 17.0 | 1698 ± 266 | 1.6 ± 0.3 | 6 |
| VA-MO | 64.2 ± 13.8 | 1064 ± 132 | 1.6 ± 0.2 | 7 |

4.3. In Vivo Effects of Valerenic Acid Derivatives Using EPM 4.3.1. Setup of the In Vivo Mouse Model System Male mice (C57B1/6N) were obtained from Charles River Laboratories (Germany). For breeding and maintenance mice were housed in groups with free access to food and water.

Temperature was fixed to 23±1C and 60% humidity with a 12 h light-dark cycle (lights on 0700-1900 hours). Age and testing experience matched male mice at 3-8 months for all experiments. All procedures involving animals were approved by the Austrian Animal Experimentation Ethics Board in compliance with the European convention for the protection of vertebrate animals used for experimental and other scientific purposes ETS no.: 123.

Figure 3:
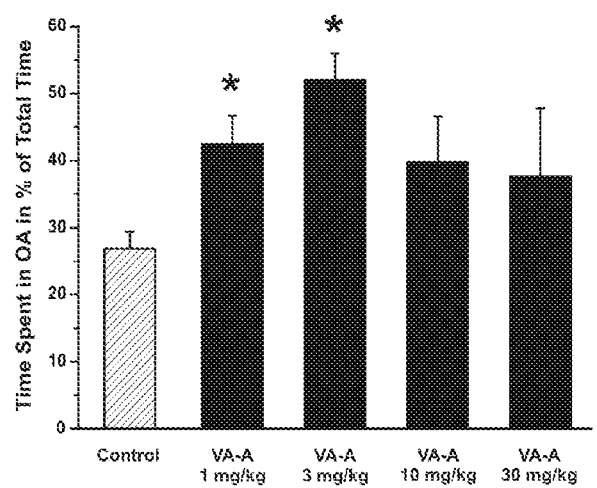
FIG. 3: Behaviour in the Elevated Plus Maze Test (assessed over 5 minutes) for control and VA-A-treated mice (concentrations represent mg/kg body weight). Bars indicate the time spent on the open arm in % of the total time. (*) indicates statistical significance (p<0.05).
Figure 4:
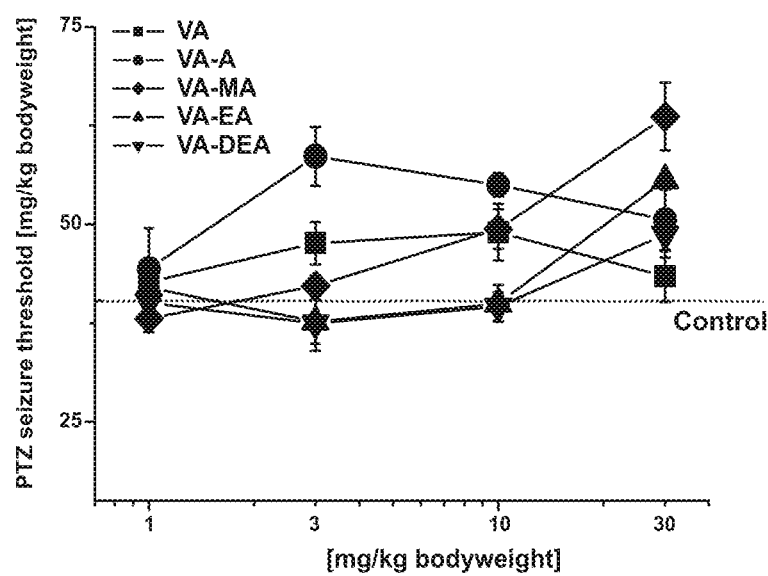
FIG. 4: Concentration-dependent modulation of the seizure threshold of mice by VA and VA-derivatives. The data points represent the mean required dose of pentylentetrazol (PTZ) in mg/kg body weight for mice that were administered a dose of 1, 3, 10 or 30 mg/kg body weight VA or VA-derivative.

Mice were transferred to the testing facility 24 h before commencement of experiments. Tests were performed between 0900 and 1300 hours. All tests were video monitored and evaluated by an experimenter blinded to the administered compound. 30 min prior to testing animals were injected either with control saline (0,9% NaCl-solution, also referred to as "vehicle") or valerenic acid derivative containing solution at the indicated concentrations (3 mg/kg bodyweight (BW) for the tests indicated in FIG. 2 and 1, 3, 10 and 30 mg/kg BW for the tests indicated in FIG. 3, see 4.3.2. for solution used).

Behaviour was tested over 5 minutes on an elevated plus maze (1 meter above ground) consisting of two closed and two open arms, each 50 cm×5 cm in size. The test instrument was build from gray PVC, the height of closed arm walls was 20 cm. Illumination was set to 180 Lux. Animals were placed in the center, facing an open arm. Analysis of open and closed arm entries and time on open arm was automatically recorded using Video-Mot 2 equipment and software (Wittmann et al., 2008).

4.3.2. Effects of Valerenic Acid Derivatives in the Mouse Elevated Plus Maze (EPM) Test Stock solutions of valerenic acid derivatives (VA-A, VA-EA, VA-DEA) were prepared in DMSO (100 mM) and the stock solutions were diluted in 0.9% sodium chloride solution up to the final desired concentrations. Finally, DMSO and Tween 80 were added to reach a maximum DMSO concentration of 10% and a Tween 80 concentration of 3%.

To compare the effect of VA-derivatives on the explorative and anxiety-related behaviour of mice, vehicle- or VA-derivative treated mice were tested in the elevated plus maze (EPM) test. As illustrated in FIG. 2, administration of VA-derivatives (3 mg/kg BW) significantly increased the time spent in the open arms of the EPM (control: 26.9±2.5% (n=25) vs. VA-A 3 mg/kg BW: 52.1±3.9% (n=21) of total time in the test). The behaviour was assessed over 5 minutes for vehicle and VA-derivative treated mice at the indicated concentrations (concentrations represent mg/kg BW). The bars the time spent on the open arm in % of the total time.

4.4. In Vivo Effects of Valerenic Acid Derivatives Using Seizure Threshold Measurements 4.4.1. Setup of the In Vivo Mouse Model System Seizure threshold was determined by pentylenetetrazole (PTZ) tail-vein infusion at a rate of 100 μl/min (100 μg/ml PTZ in saline, pH 7.4) on freely moving animals. 30 min prior to test c57B1/6N mice were intraperitoneally injected with either saline (=control group), VA or VA derivatives at the indicated concentrations. Infusion was stopped when animals displayed generalized clonic seizures. Animals were immediately anaesthetized using increasing carbon dioxide concentrations and killed by cervical displacement. The seizure threshold dose was calculated from the infused volume in relation to body weight. Results from tail-vein infusion were verified by intraperitoneal injection of a fixed dose of 30 mg PTZ/kg body weight. Animals were observed and video-tracked for 20 min after treatment.

4.4.2. Effects of Valerenic Acid Derivatives in the Seizure Threshold Measurements Wild-type mice injected with the saline solution showed clonic seizures at 40.4±3.5 mg PTZ/kg (n=6) body weight. Mice treated with either VA or derivatives of VA at concentrations ≥3 mg/kg bodyweight displayed a significantly increased seizure threshold. At 3 mg/kg bodyweight, the anticonvulsant effect was most pronounced for VA-A raising the seizure threshold to 58.6±3.7 mg PTZ/kg (VA-A, n=5) compared to 47.7±2.7 mg PTZ/kg (VA, n=8) and 40.4±3.5 mg PTZ/kg (Saline) (see also FIG. 5). At 30 mg/kg bodyweight the anticonvulsant effects of VA-MA, VA-EA and VA-DEA have significantly increased, wherein VA-MA displayed the strongest anticonvulsant effect.

The invention claimed is:

1. A compound of formula (IA2):

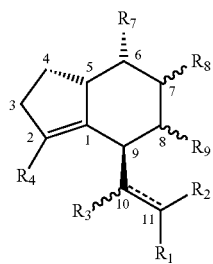

(IA2)

wherein
the dotted line between $C_{10}$ and $C_{11}$ represents an optional double bond;
$R_1$ is selected from the group consisting of substituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl, substituted or unsubstituted heteroaryl, —(C0-C10)C(O)$R_{10}$, —(C0-C10)C(O)O$R_{10}$, —(C0-C10)OC(O)$R_{10}$, —(C1-C10)S$R_{10}$, —(C0-C10)C(O)N$R_{11}R_{12}$, —(C0-C10)C(O)NHN$R_{11}R_{12}$ and —(C1-C10)O$R_{10}$;
wherein $R_{10}$, $R_{11}$ and $R_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;

$R_2$, $R_3$, $R_4$, $R_7$, $R_8$ and $R_9$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl, substituted or unsubstituted heteroaryl, —CN, —(C1-C10)OH, —N$R_{11}R_{12}$, —(C0-C10)C(O)$R_{10}$, —(C0-C10)C(O)O$R_{10}$, —(C0-C10)OC(O)$R_{10}$, —(C1-C10)S$R_{10}$, —(C0-C10)C(O)N$R_{11}R_{12}$, —C(O)NHN$R_{11}R_{12}$ and —(C0-C10)O$R_{10}$;

wherein $R_{10}$, $R_{11}$ and $R_{12}$ independently from each other are selected from the group consisting of H, substituted or unsubstituted C1-C10alkyl, substituted or unsubstituted C3-C8cycloalkyl, substituted or unsubstituted C2-C10alkenyl, substituted or unsubstituted C4-C8cycloalkenyl, substituted or unsubstituted aryl and substituted or unsubstituted heteroaryl;

or a pharmaceutically salt thereof or solvate thereof or a prodrug thereof;

excluding the following compounds and Z- or E-isomers thereof:

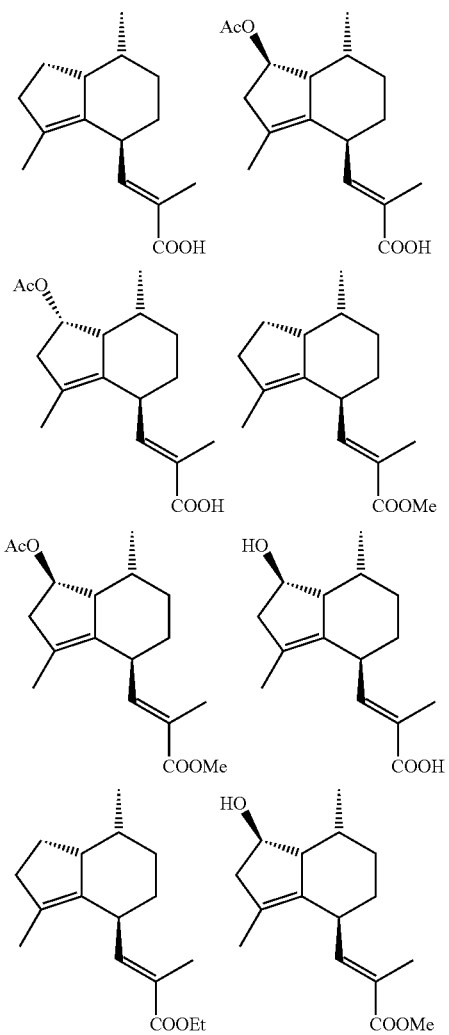

-continued

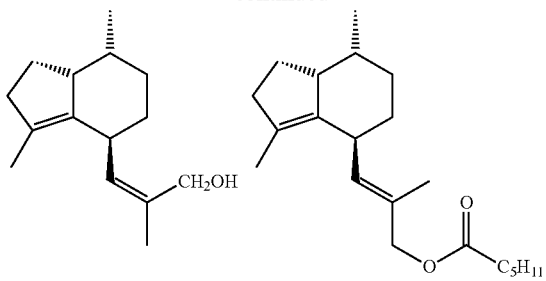

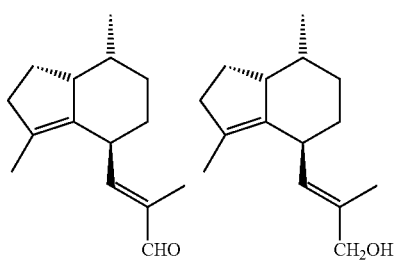

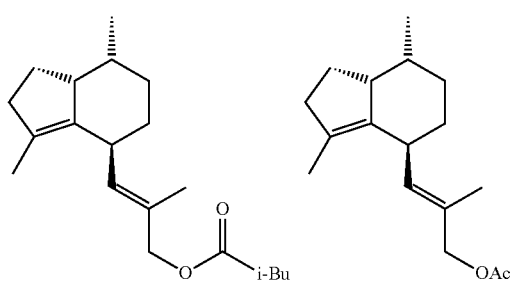

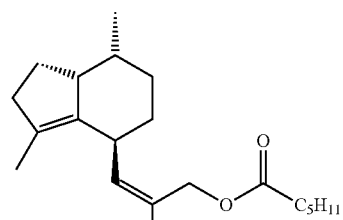

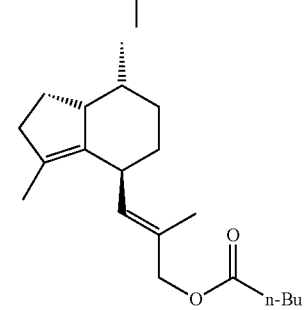

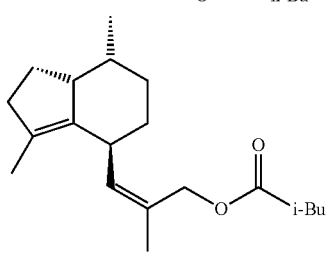

-continued

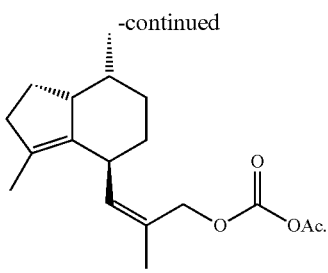

2. A compound according to claim 1 wherein the bond between $C_{10}$ and $C_{11}$ is a double bond.

3. A compound according to claim 1 wherein $R_3$ is H.

4. A compound according to claim 1 wherein $R_8$ is H.

5. A compound according to claim 1 wherein $R_7$ is selected from the group consisting of substituted or unsubstituted C6-C10alkyl, substituted or unsubstituted C5-C8cycloalkyl, substituted or unsubstituted C6-C10alkenyl, substituted or unsubstituted C4-C8cycloalkenyl, substituted or unsubstituted aryl, substituted or unsubstituted heteroaryl, —(C6-C10)OH, —$NR_{11}R_{12}$, —(C6-C10)C(O)$R_{10}$, —(C6-C10)C(O)O$R_{10}$, —(C0-C10)OC(O)$R_{10}$, —(C6-C10)S$R_{10}$, —(C6-C10)C(O)N$R_{11}R_{12}$, —C(O)NHN$R_{11}R_{12}$ and —(C6-C10)O$R_{10}$;

wherein $R_{10}$, $R_{11}$ and $R_{12}$ independently from each other are selected from the group consisting of substituted or unsubstituted C6-C10alkyl, substituted or unsubstituted C5-C8cycloalkyl, substituted or unsubstituted C6-C10alkenyl, substituted or unsubstituted C4-C8cycloalkenyl, substituted or unsubstituted aryl and substituted or unsubstituted heteroaryl.

6. A compound according to claim 1 wherein the bond between $C_{10}$ and $C_{11}$ is a double bond, $R_2$ is unsubstituted C1-C3alkyl, $R_3$ is H, $R_4$ is unsubstituted C1-C3alkyl, $R_7$ is unsubstituted C1-C3alkyl, $R_8$ is H and $R_9$ is unsubstituted C1-C3alkyl.

7. A compound according to claim 1, wherein $R_4$ and/or $R_7$ is methyl.

8. A compound according to claim 1 wherein the bond between $C_{10}$ and $C_{11}$ is a double bond, $R_2$ is unsubstituted C1-C3alkyl, $R_3$ is H, $R_7$ is unsubstituted C1-C3alkyl, $R_8$ is H and $R_9$ is unsubstituted C1-C3alkyl.

9. A compound according to claim 1 selected from the group consisting of (E)-3-((4S,7R,7aR)-3,7-dimethyl-2,4,5,6,7,7a-hexahydro-1H-inden-4-yl)-2-methylacrylamide, (E)-3-((4S,7R,7aR)-3,7-dimethyl-2,4,5,6,7,7a-hexahydro-1H-inden-4-yl)-2-methylacrylohydrazide, (E)-3-((4S,7R,7aR)-3,7-dimethyl-2,4,5,6,7,7a-hexahydro-1H-inden-4-yl)-N,2-dimethylacrylamide, (E)-3-((4S,7R,7aR)-3,7-dimethyl-2,4,5,6,7,7a-hexahydro-1H-inden-4-yl)-N,N-diethyl-2-methylacrylamide, (E)-3-((4S,7R,7aR)-3,7-dimethyl-2,4,5,6,7,7a-hexahydro-1H-inden-4-yl)-N,N,2-trimethylacrylamide, (E)-3-((4S,7R,7aR)-3,7-dimethyl-2,4,5,6,7,7a-hexahydro-1H-inden-4-yl)-N-isopropyl-2-methylacrylamide, (E)-N-butyl-3-((4S,7R,7aR)-3,7-dimethyl-2,4,5,6,7,7a-hexahydro-1H-inden-4-yl)-2-methylacrylamide, (E)-3-((4S,7R,7aR)-3,7-dimethyl-2,4,5,6,7,7a-hexahydro-1H-inden-4-yl)-2-methyl-1-morpholinoprop-2-en-1-one, (E)-3-((4S,7R,7aR)-3,7-dimethyl-2,4,5,6,7,7a-hexahydro-1H-inden-4-yl)-2-methyl-1-(piperidin-1-yl)prop-2-en-1-one, (E)-3-[(4S,7R,7aR)-3,7-dimethyl-2,4,5,6,7,7a-hexahydro-1H-inden-4-yl]-2-methylprop-2-enamide and (E)-3-[(4S,7R,7aR)-3,7-dimethyl-2,4,5,6,7,7a-hexahydro-1H-inden-4-yl]-2-methylprop-2-en hydrazide.

10. A pharmaceutical composition comprising a pharmaceutically effective amount of a compound according to claim 1, optionally in the form of an ester prodrug.
11. A compound of formula (10a):
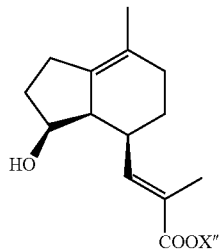
(10a)
wherein X" is selected from C1-C10alkyl, C2-C10alkenyl, substituted or unsubstituted aryl.
* * * * *